United States Patent
Spradling et al.

(10) Patent No.: US 7,402,665 B2
(45) Date of Patent: Jul. 22, 2008

(54) NUCLEIC ACID ENCODING A POLY-(ADP) RIBOSE POLYMERASE ENZYME AND USES THEREOF

(75) Inventors: Allan C. Spradling, Baltimore, MD (US); Dianne Stewart Williams, Baltimore, MD (US); Alexei V. Tulin, Baltimore, MD (US)

(73) Assignee: Carnegie Institution of Washington, Washington, DC (US)

( * ) Notice: Subject to any disclaimer, the term of this patent is extended or adjusted under 35 U.S.C. 154(b) by 537 days.

(21) Appl. No.: 10/630,660

(22) Filed: Jul. 31, 2003

(65) Prior Publication Data

US 2004/0127444 A1 Jul. 1, 2004

Related U.S. Application Data

(60) Provisional application No. 60/399,460, filed on Jul. 31, 2002.

(51) Int. Cl.
*C07H 21/04* (2006.01)
*C12N 9/12* (2006.01)

(52) U.S. Cl. ............... 536/23.4; 435/194; 536/23.5; 536/23.1

(58) Field of Classification Search ............ 435/194
See application file for complete search history.

(56) References Cited

OTHER PUBLICATIONS

Ngo et al. in The Protein Folding Problem and Tertiary Structure Prediction, 1994, Merz et al. (ed.), Birkhauser, Boston, MA, pp. 433 and 492-495, Ref: U, Form-892.*

Uchida et al., Proc. Natl. Acad. Sci. USA, vol. 90, pp. 3481-3485, May 1993.*
Zhang, P., and Spralding, A.C., "Insertional mutagenesis of *Drosophila* heterochromatin with single *P* elements," *Proc. Natl. Acad. Sci. USA* 91:3539-3543 (Apr. 1994) National Academy of Sciences).
Tulin, A., and Spralding, A., "Chromatin Loosening by Poly(ADP)-Ribose Polymerase (PARP) at *Drosophila* Puff Loci, "*Science* 299:560-562 (Jan. 2003) American Association for the Advancement of Science.
NCBI Entrez, Accession No. NM_079971, Uchida et al., 5 pages (1993) National Center for Biotechnology Information.
NCBI Entrez, Accession No. NM_145619, Urbanek, P., 3 pages (2001) National Center for Biotechnology Information.
NCBI Entrez, Accession No. AY118947, Stapleton et al., 3 pages (2002) National Center for Biotechnology Information.
NCBI Entrez, Accession No. AF533701, Tulin et al., 2 pages (2002) National Center for Biotechnology Information.
NCBI Entrez, Accession No. AA803347, Harvey et al., 2 pages (2001) National Center for Biotechnology Information.
NCBI Entrez, Accession No. AAM93435, Tulin et al., 2 pages (2002) National Center for Biotechnology Information.
NCBI Entrez, Accession No. AF533702, Tulin et al., 16 pages (2002) National Center for Biotechnology Information.

* cited by examiner

*Primary Examiner*—Richard G Hutson
(74) *Attorney, Agent, or Firm*—Morgan Lewis & Bockius LLP

(57) ABSTRACT

Poly(ADP)-ribose polymerase (PARP) becomes activated at sites of DNA damage and is thought to promote repair by modifying local chromatin proteins and transcription factors. Disclosed is an isoform of PARP, PARP-e, which lacks enzymatic function and which is encoded by a gene having a novel structure. Also disclosed are methods of modulating chromatin structure resulting in modulation of gene activation, gene repression and chromatin condensation and decondensation.

4 Claims, 28 Drawing Sheets

Figure 12

PARP-e cDNA sequence: SEQ ID NO: 1

```
   1  cctcatcatg ntgtgtagac gttatagctt ctttttctat tttggtcacc gggctgagta
  61  gcgctactct taatacgttt aattgttaat tttaatttta attttcatt. gcccacattt
 121  ttgaaagtct atcgaaatat tttcaaagtt attttcccac ggtgccattt taactgtctt
 181  gattttgtgt ataccggcct ggttttcaag cctttggaaa aactgatcta aatcgagatt
 241  tccaatagga attttgtcta cattgatatc tggtatgtaa tatggatatt gaattacctt
 301  atcttgctga gtatgcaaga actggacgag ccacttgcaa aggatgtaaa agtactatat
 361  ctaaagatac tcttcggatt gctgtcatgg ttcaatctgc atttcatgat gccaaagttc
 421  cgaattggtt tcataaaacc tgcttttta aaaccagcg tcccagctca gtaggagaca
 481  tacaaaacat tggaaatctc cgatttgccg atcaaaagga attaacggat cttgtggaaa
 541  atatacaaga agttataagc gcacaattag gaaaaagcg atcgaaggct tttaacttag
 601  cattaaaaga ctttgggatt gaatatgcaa atctagtcg atcgacgtgt cgtggatgtg
 661  aacaaaaaat aaacaaggat ctagttcgct tacgtaaaac tgtttatgat actgaagttg
 721  gtatgaagta cggaggccaa cctttgtggc atcatttgga atgcttcgcc caattgcgct
 781  ctgagcttgg ctggtttgcg tcaggtgaag atatgccagg atttcagagc ttagcagatg
 841  atgatcaagc gaaagttaaa aacgccatac caccaataaa atctgaagaa ctaccagata
 901  caaaaagagc taagatggaa ttatcagata caaatgaaga aggagaaaag aaacaacgct
 961  taaaagatca aaatgatgcc tacttcaggt ttcgcgatga cattaaaaat aaaatgaaga
1021  agaaagacat tgatatactt cttaagttta ataatcaaca acctgtaact ggtgacacag
1081  aaaagttatt tgatcaaact gccgatttac tgacattcgg agctattgaa tcatgttctg
1141  aatgcaacag ctgtcagttt attgttaata aatctggata tatatgtaat ggaaatcatt
1201  ctgagtggac caaatgtaac aagctgctaa aagagccaac aagatcggca tgcatagtgc
1261  caaaagaact taagcattta tataattttt tgaataccgt gaaagaaatt ccatctacac
1321  ggatctttaa taactttcct cccaataaaa gtaccttttc tagaagtctt ttgaaaacga
1381  ataaaaacaa tgatgttttg gttaggccaa caatacctcg tataagtccg ccattataca
1441  atttaaagtt ttcaattata ggcttaaaga accagcataa agagctaaga aagcgaatag
1501  aaaatttggg cggtaaattt gaagttaaaa tatcggaaaa cacgatagca ataatatcaa
1561  cagaattaga aatacaaaaa aaatccaccc gtatgaagtt tgcagaagag ctcggaattc
1621  atattgtgcc cattgaattt ttagattttg ttgaagccga tacagaagga gctattaaat
1681  atataaatag cacatgtatt tgtagttggg gaacagatcc aaaatccaga attccaaagg
1741  aaacaacaaa aagtttaaat tcgaacagta tatatacaaa atccatgcca gtatcacgga
1801  catttaaagt aaaagatggc ctagctgttg atccggacag tgggctcgag gacatcgccc
1861  atgtttacgt ggacagtaac aataaataca gtgttgttct tggcttaact gacattcaga
1921  gaaataagaa ctcctactac aaagttcagc ttttaaaagc ggataaaaag gagaaatatt
1981  ggattttcg ttcatggggt cgaattggaa caaatattgg aaactcaaaa cttgaagagt
2041  tcgacacgag cgagtctgca aaaagaaatt ttaaagaaat atatgcagat aaaactggaa
2101  tgcacttcag cgaaatacat taataaacta tcaaataata aacatagttg tttcggtcgt
2161  ggtcgcacca tgccagatcc tactaagagc tatataagaa gtgatggggt tgaaattcct
2221  tacggagaaa ccattactga cgaacattta aagtcatcgt tattatataa cgagtatata
2281  gtatatgatg ttgcgcaggt caatattcaa tatttgtttc gtatggaatt caagtattct
2341  tattaaatgc cttaaattat attgagtgat attgatatta ataaattgga attattttaa
2401  aaaattaaaa aaaaaaaaaa aaaaaa
```

Figure 13

Amino acid Sequence of PARP-e: SEQ ID NO:2

```
MDIELPYLAEYARTGRATCKGCKSTISKDTLRIAVMVQSAFHDAKVPNWFHKTCFFKNQRPSSVGDIQNIGNLRFAD
QKELTDLVENIQEVISAQLGKKRSKAFNLALKDFGIEYAKSSRSTCRGCEQKINKDLVRLRKTVYDTEVGMKYGGQP
LWHHLECFAQLRSELGWFASGEDMPGFQSLADDDQAKVKNAIPPIKSEELPDTKRAKMELSDTNEEGEKKQRLKDQN
DAYFRFRDDIKNKMKKKDIDILLKFNNQQPVTGDTEKLFDQTADLLTFGAIESCSECNSCQFIVNKSGYICNGNHSE
WTKCNKLLKEPTRSACIVPKELKALYNFLNTVKEIPSTRIFNNFPPNKSTFSRSLLKTNKNNDVLVRPTIPRISPPL
YNLKFSIIGLKNQHKELRKRIENLGGKFEVKISENTIAIISTELEIQKKSTRMKFAEELGIHIVPIEFLDFVEADTE
GAIKYINSTCICSWGTDPKSRIPKETTKSLNSNSIYTKSMPVSRTFKVKDGLAVDPDSGLEDIAHVYVDSNNKYSVV
LGLTDIQRNKNSYYKVQLLKADKKEKYWIFRSWGRIGTNIGNSKLEEFDTSESAKRNFKEIYADKTGMHFSEIH
```

Figure 14

DNA sequence of PARP: SEQ ID NO: 10

```
   1 tctagaccac ggcaaaaaat cgtgtgccaa aaatnntatg gcgttacgca tcttgttatt
  61 ctagngtctt tggatatggg gtgatcattt tgagaattta ctgcccgaag gtctaaattc
 121 ctgtcatctg tggttacatt tttttcgaaa tcgggaaatt caagaatttg tttgtttatt
 181 attaaagctt taagttttg aatgcgcctc tatgtattca aggttttgtg catctatctt
 241 gcaccttttt tttttaatt tggtcattgg ttttgctata tctgcgttat ttgaataaa
 301 ctcacgataa taaccggtta gtccaaggaa agctctgatt tggaattgg atggctgttg
 361 tttttagagg gtttggtttt ataccgttag cttttttttt aagaattcac atttatcaag
 421 tttcaattat aatttgctt ctgcactaat tgttaaaaaa gttattatat cattcaaata
 481 tactaaacag tgtttgttaa gcaaatgtcg aaggatatta tgcatgcacc tttgaaaagt
 541 cccggtgcat tcctaangcc aaatggcatt cgaaggtact cgtaataccc gttttcgatg
 601 gcaaatgcag ttttggatat ttcttttctg tttgataaaa tgcttttgcc agatcaatag
 661 ttgtaaaata ttgacatttt cctaatgtac caaggatttc gtccatgttt gctattggat
 721 ctctgtcggg aattagttat ttcataatcg ctacgctata cttgattta ccacaagcat
 781 cagtaagcaa ttactattcc taattaatcc gtgatttagc gtttccagta attggttttc
 841 gactttaatt tcgtgcgttt gagcaaaagg gtaaagtggt gcgggtggca aatgttttt
 901 ttgcatatcg atagatattt acaagactga tacaaaaatc aaaaatttt taaaaagtgt
 961 tggtgttacg tgctgcctgg cttcttatat cctatttcct atatcctata tccctatatt
1021 tgtagcttct agatatatcc ttgaccaaaa ccagtgcagt ggcgaggatg acacgaaaaa
1081 cgaagttccg tgtgagtatg tgtgactgcc tccgaaattt ggacagacgt tctactttaa
1141 gttgtgcgtg atccagatga aagtcgataa agcagcgaat gaacgcacgg gtaaggcaaa
1201 cgtacggtgc taacgaaaat gtcgacaata ttttgcccca ttcgaaaaca atttcaaaga
1261 gcatcgttat tatggcatct caagagcact tggtccagt taaagcggag attgtaanag
1321 ttcaagctgt gtcgtatgga cagaccatca tttaagattg tcttatctgt cctttaccat
1381 acattatata agagaaggca tattggtaat gaaaggagaa tcctgcacag gtaattgaat
1441 ttaaatataa atttagtgct tttcaatcac caaaaaatg aataatgcta attattttat
1501 tatttttta gatgtaatta ttcttattaa actaatagat attaaaaaat tttggttgca
1561 accttgataa agaccagcct gtgattgtta cggatagagg ttttaacatg ataacgtcct
1621 tccaaggata cgaccatatt ttttgcacaa cattatagag gcaacggtaa aaaaaaatta
1681 tagaattttc taaaatggtt gatacatgca gtaaaatagt taagtttttt aagaagtcag
1741 ggtaaatttt ttctttaaat acgacattga aaagcttgat actgatttaa ataaattggg
1801 gagttatgtg tttctagacc acggcaaaaa atcgtgtgcc aaaaatnnta tggcgttacg
1861 catcttgtta ttctagngtc tttggatatg gggtgatcat tttgagaatt tactgcccga
1921 aggtctaaat tcctgtcatc tgtggttaca ttttttcga aatcgggaaa ttcaagaatt
1981 tgtttgttta ttattaaagc tttaagtttt gaatgcgcc tctatgtatt caaggttttg
2041 tgcatctatc ttgcaccttt ttttttaa tttggtcatt ggttttgcta tatctgcgtt
2101 atttggaata aactcacgat aataaccggt tagtccaagg aaagctctga ttttggaatt
2161 ggatggctgt tgtttttaga gggtttggtt ttataccgtt agcttttttt ttaagaattc
2221 acatttatca agtttcaatt ataattttgc ttctgcacta attgttaaaa aagttattat
2281 atcattcaaa tatactaaac agtgtttgtt aagcaaatgt cgaaggatat tatgcatgca
2341 cctttgaaaa gtcccggtgc attcctaang ccaaatggca ttcgaaggta ctcgtaatga
2401 cccgttttcg atggcaaatg cagttttgga tatttctttt ctgtttgata aaatgctttt
2461 gccagatcaa tagttgtaaa atattgacat tttcctaatg taccaaggat ttcgtccatg
2521 tttgctattg gatctctgtc gggaattagt tatttcataa tcgctacgct atacttgatt
2581 ttaccacaag catcagtaag caattactat tcctaattaa tccgtgattt agcgtttcca
2641 gtaattggtt ttcgacttta atttcgtgcg tttgagcaaa agggtactga tttaaataaa
2701 ttggggagtt atgtgttgta tttagtacgt atttaatagt atttgtaaat gtttatgtat
2761 tgaagatttt taaatttatt taataaacct ttcacctta aattttcctc ctgatttagg
2821 tgatgaaata gatttgagtt ttctattggt tctggtgtct tttggatata tatatactaa
2881 taagttgaaa ttgtttgaat tcatgcgcgt cttgaagtct catttcgtca atagcatttt
2941 tggttcgttc actgtccgaa ggtcttagcc gtatttttag atgtggccaa ccctccaacc
3001 ctcgttgagg gtacgcattt cctctgaaat gtgctgtttg atgatttga gttttattgg
3061 gatgttgtgg aaaaggattt tttttaataa ttcgttatgt gttcatgtat tggattggtc
3121 tgaaataatt aggtaccggt cacataggtt ggttattagt catctgctgt gtataggtgg
3181 gtctaaatgg tggttattaa ttaggttgga agggttgaga atattgtggg taacttggtc
```

Figure 14 (continued)

```
3241 gatattgagt ttggtcaagt ttattgaata tgtgtgattt agaatgttga ttaagattta
3301 agtttttatc tggatttta tttaatttaa aattaatatg ttcatcatat attgcaatag
3361 aaattaaaga tcttacgtca taatgtgtta aaatagtgaa taattgtatt ggtagttttc
3421 taatcagcat tttaatagac ttaataaata ataaatttat taaataagaa attccaattt
3481 acgtcgcgtt tctgcttctt cgcagaattc tcttcgattt ccttttttag ttgtctccct
3541 gaagttcacc agtagttcgg tgcttgggc ttaaattctg agattatttt ggatttcagg
3601 gttggccaat cttcgatgtt cggaagtccc atagatcgtg ttacttgtcc gtccaagttt
3661 cttttgatgg ctccaagtaa aatcctctgt tgtcgcacat cattcgtttg gtagattgaa
3721 attacgtagt ccaacctgct tatgaaggt tcctggatca cccttaaatg gcattatgtt
3781 ttttagctga cgacggtatt tagcgaggtt gttgtcgctt ggcgcaacta tttggggtgc
3841 ggcaataatt ggatgtgccg ttttattgt agatttttat tttgtattgt tttcgaatac
3901 tttttgtatc ctactaatta ttccagtaaa atgtttgtat attattgagt cgtccagcca
3961 gttgactgag gacaacgtta agaaataaaa aaaattatcg gagagatagt tttgacgtct
4021 ttattctttt gatctcagct taaaaataaa tgttagttac aaaaatcttt cttatactgc
4081 catttttcttt aaattatttc gaaagcgagg tcccccgctt gggatattgg ttgtatacag
4141 ctaccagatg tggattgttt acattgcgtg ggattcgcca ctctgcatat tcttatttct
4201 tccgaaagtg ctgattatgt gaatatgtaa tatgctcact ctttgttcgc atattttaac
4261 gctgcctgtg tgcatacata atttgccctc ccactagcca catgcatctc ctaatcggga
4321 gactggaatt tatcgttctc ttagttttaa ctactactaa ataaaagctt aagtaatttt
4381 gtagtaaaat tcaatatccc ttataaatat atgtcgtgga ttttttttacg gtatatgtag
4441 ttttttaaaaa tcgtcttaca aacattaaaa atctaccttt tttaatctaa ctagatttt
4501 ttaattaaaa ttttctgtc tatttatagg cgttccagct atggcaggta gcgcaataat
4561 cgggggcgta ctcttagctc ttatcgaagg tgttggaata ctgtttacaa gaatttctgc
4621 tgaccagttt aaaaatccga taccacctgc agaagacccc gtagcccttg gagatcctgg
   4681 aagaaatttt tcatttgaat ccgcttctaa ccgaacacaa tatcaataaa ctagtaacca
   4741 tgtgaaaaca aaaaacaata accttagaat aaggtgataa atatgtattg attattctta
   4801 ttcatgatcg ctcagctgta gtcgagttcc ccgactataa gatacattat taagctagtg
   4861 gaagtgatac cgctaaattt catcattgtt ccggcatatt gatacatatt ggataatata
   4921 atcaaaaaga attggaggtt tgtttgtgta agtaaggcaa atcgtttgaa atttacaaga
   4981 ctaataaata tataaaaaag atcaatatat ttttcaaaag tgtgtggtta ggggggcgata
   5041 aagtggtgcg ggtggcaaaa tgttttttg catatcgata gatatttaca agactgatac
   5101 aaaaatcaaa aaatttttaa aaagtgttgg tgttacgtgc tgcctggctt ctaaatatat
   5161 cctatttcct atatcctata tcctatatt tgtagcttct agatatatcc ttgaccaaaa
   5221 ccagtgcagt ggcgaggatg acacgaaaaa cgaagttccg tgtgagtatg tgtgactgcc
   5281 tccgaaattt ggacagacgt tctactttaa gttgtgcgtg atccagatga aagtcgataa
   5341 agcagcgaat gaacgcacgg gtaaggcaaa cgtacggtgc taacgaaaat gtcgacaata
   5401 ttttgcccca ttcgaaaaca atttcaaaga gcatcgttat atggcatctc aagagcactt
   5461 tggtccagtt aaagcggaga ttgtaaagtt caagctgtgt cgtatggaca gaccatcatt
   5521 taagattgtc ttatctgtcc tttaccatac attatataag agaaggcata ttggtaatga
   5581 aaggagaatc ctgcacaggt aattgaattt aaatataaat ttagtgcttt tcaatcacca
   5641 aaaaatgaa taatgctaat tatttttatta tttttttaga tgtaattatt cttattaaac
   5701 taatagatat taaaaaaaat tttggttgca accttgataa agaccagcct gtgattgtta
   5761 cggatagagg ttttaacatg ataacgtcct tccaaggata cgaccatatt ttttgcacaa
   5821 cattatagag gcaacggtaa aaaaaaatta tagaattttc taaaatggtt gatacatgca
   5881 gtaaaatagt taagtttttt aagaagtcag ggtaaatttt ttcttttaaat acgacattga
   5941 aaagctgaa aaccaaagac actagaataa caagatgcgt aaggccatac tatttttggg
   6001 cacacgattt tttcgccgtg gctctagagg tggctccagg ctctctcgaa ttttgttaca
   6061 gagcggagag cgctacagcg aacagctctt ttctacgcat acagtgatgg cagacaactg
   6121 tatgtgtgcc catgtatgct catgcattgt aaatttgaca aaacatgccc ttcaagttct
   6181 tggactttaa atctatatta tttttgatca attggcacca tgcgaaaaat tcttgttttt
   6241 cattgcctta acgttattat aatttgaaaa tagattagaa atagccaaat ctatgtacat
   6301 attatcacaa aataaaattc aaaactgact ttatatatat atacagttgc ggtaacaata
   6361 atagcaccat aagcacattt cgtgtttgtc ccagcgtttc tctattttct gacactttt
   6421 tcatcatttt actcactaaa cttaaatact acaatgattt tcaatcgaaa taaaaaaatt
   6481 agtaacagta acagtaacaa aaaaaactgt taaaaaaaac aaaaaaatag cactgtttct
   6541 cgtagtttgc taagactaac caaagaaata aaaaaataat tcaacaaatg ggattatatc
   6601 ttaagaacta tgtttaaaga atcttaatat ttagtttgcg tggaccttt ggttggcaat
   6661 aacagccgcg catcgtcctg gcatggagtc caccaagtcc cggcacagtt tttgaggaat
   6721 ttaccgttat tattgggttn ggcttcaaaa acctttttt caggncttnc caagggtttc
   6781 gatgggatca gtcggtgatt gagnaggcca gtnttcctgg acaatctgnt ctaacccttt
```

Figure 14 (continued)

```
6841 cactttctgg tcggnggttg ggncgtatcc gtcgaaagtc aaaccacggt ttcatcccgg
6901 atatgggaga tacatttccg gaaattgngc tatcgccttg gcatggagtc caccaagtcc
6961 tgtcaccgtt tttgagaaat tttggtccat gaatccttga caacacccca aagatcctcg
7021 ttattattgg gtttggcttc agaaatcttt ttttcacttc cgcccaaagg ttttcgattg
7081 gattcaagtc gggtgactga gcaggcgatc gcattactcg gatcgatttc tgctcaaacc
7141 actttctagc tttcttgctc gtgtgttttg ggtcgttatc ctgttgaaat gtccaagcca
7201 acggcatatc atcctcggca tatggcagca tcacattttc caggagatct gtgtaaatgt
7261 gctgatccat gatgccttga atctaatgga tcggacctac tccatagtat gaaaatcacg
7321 cccataccat gatgtttgat cccccgtgct ttaccgcctt aaaggtgaag cgaggattat
7381 attcagttcg tggtggacgc cgaacataag accgagagcc tttcccacca acaacacaa
7441 ttttgctctc atctgaccac aaaatgttgc gccacttctc cacaggccag tccttgtgta
7501 tcttggcata ttcgagtcgc tttgccacat gcttaacagt caaaagcggg acttttctgg
7561 gactgcacgc attaaggttg ttttgtctta agcgtttgcg aactgtttcc acgcttgcag
7621 ctatctgaag ctccttcttc agttccgtcg ccggcttaaa aggctccttc ttgctttgcc
7681 gaaccaagcg cttgatctcc acgttggaca ttgagggctt cttccacgt gtttcgtcct
7741 tttcgacaaa cagcattgtg gatcattttg tttgaacacc cgacaattcg accaatttca
7801 gcgtaggttt tacattcaga gatcatgttt taatcaaat ttctttttc gacggtacaa
7861 tgcttttcgc gacccataac tagagaattt ttggtcttcg tttggaacaa attcaattaa
7921 aaccttaat acaactcctt ttttcaaaat ttgtcgaaaa aatcccaaa tcactcctat
7981 taattttatt caacaaatac gtggtcagtg ctattttgt taccgtctca tttcgcgcgc
8041 ttttgcagca agtgcccaaa aacaaaaga accgttacat tgagagta aaatttctt
8101 gctcagagag gcgcgtatgt tttagggatg caagaaaagg gcctatcgat agtgcgggtg
8161 ggggttgatg gcttttggag ctatcggtgc ggtcgtgcgt ggcctatcgt tttatcgatg
8221 taaaaccggt ggctagcgtt agttaatcaa atactattca aatttgaata tgtcggagat
8281 gccaagcgcg acttttcatt tacttcagcg tccatattgt ccagcacatc aagtcgcctg
8341 cgtgttgttt cttctgtcgt tctaagcaga ctaatttact caagcgtcgc cttcgcgatg
8401 cttttcttct attcctcacc ttccatcaat tatttcatcc ttacttcgtt tccagaaact
8461 atacaacaac aacaacagcc acacaaatga tgcccactca ataacggaac gctttccgtg
8521 aatttcattg ctcgctgctc attcttaaca taacggatca ataacaaaat gtcggttaca
8581 ttctactact caatcttgct tgtgaaattt tgctgatcaa acgtgcttaa agcgaattat
8641 taaattaat aaaatgcctg gaaagagata aactttgaag ttacccaatt aataaactat
8701 aaccaccagt tgggaaaatc ttttccagaa taagtataa tgttttctgt atcccgtaag
8761 accgtctact attttttaaa aggctcggaa aaagaggaca ggcttgaacc taagagtggt
8821 ggtgggcgga aaattaaaat taaaaagcgt gtagaccgct ttattatgcg aatagagatt
8881 gcgaacccc ggtcagatca cttgctctgg atatcaggca agagtgtcac ctaactgtgt
8941 cacacgaaac tgtgcgccaa gtcatcctac gccatagata ctcttcaaga gttgcgagga
9001 aaaatccttt gctatcagat gccaatatgg aaaagcgtca ttaattcgct gtgaacaagg
9061 tggatcatcc agaagagtac tgggatgacg tcatatttgg tgacgaaaca aaaattatgc
9121 tcttttataa cgacgggcca agcagagtat ggcgcaaacc gctgagtgcg ctagaaaaac
9181 aaaatatcat tccaacgata aaatttgaaa aaatgtcact gatggtttgt ggctgtatca
9241 ccagccatgg agtgggaaaa ctagccttaa tttagagcac aataaatgcc gtgcaatatc
9301 taggaatctt aaaaaacaaa tttgaaggcc ggtgcagaaa aatttggtct agttagcaac
9361 aacaagccaa attttatatt ttaagaggac atgatcagaa acataaagag tgcaatgtac
9421 gcacctggcg cccttataac tgtggtaaag tgatcgatac gccccccta gagtcctgat
9481 ctgaaccca ttgaaaattt gtggacctac ttaagaaga aggtggcaaa aagggcccta
9541 aaacacgaca acagcttatg actgcaatag tcgaatggtg tgaaaagatc ctgcttgaat
9601 atgacctaca aaaacttatc cattccatga aaaaaaggc ttcaacttgt agcgtaagcc
9661 aacggggaac atactacata ctaaaacttt taaaatttta atgaaataat ttaaaaattt
9721 aggagtaaac ttcgattaag tgttttgtgt aaagagtttc ttgaagtgtg taaacttgga
9781 atttcttgtt tattttcttg tatatttaat atttttaatt tgttttttga tttatactta
9841 aaataaatgt tgtttaatta tattgaataa agaattgcg tttaattaag caaagaaccc
9901 ttcatttta cctttaaaat caaaaattca acttatttca cagtttcttg acaaactgta
9961 attagtttct tagctttgaa gcgtagaagc cagtttgcaa aaggaaggac aggagggcat
10021 ggttatattg acttggctat tcgtacttat taagaatgta gtgtttttat acagccgtaa
10081 atgtcttctt taatgcctcg caactttttt aaagatatta aatattctc tgcgaggtta
10141 taatatgaat ccgtgtttct ctctccatag ttcttaatt gttggcaact tatcgacgtt
10201 atcttgacgc acatcgaaat ttacaaagta ctggtattac ccattggcca gtgcgcgttt
10261 gactactaat aatttttacgt taataatttt ttaagtccctt ttaacgttgt tttggcaata
10321 aaaatgactt ctcgcgataa tattttcgag gaaaaatat gcaatagatt agatcattgc
10381 gtttctgatg tattaattaa aggatgtgag tacgaacatt tacgtaacat tttaaaaccg
```

Figure 14 (continued)

```
10441 tggtatttgc atattgaaat atcaattttt aaaagcaaaa tcaaaacggt attttaaatg
10501 gcatttatta ccatttttaa taacccagca tatgatgtat gaaaaattat aatttggcta
10561 ggctaagttg tataaagttg tatggcatga gtagacaagt gtattgttta aatcttgcaa
10621 actaaaaata attttataat taaaatggtt tgcttaagct aaacattcag aaacgtaatc
10681 atacctcgca gatttccaaa aaacatcaaa atatgccgaa gttcgggata taaaataatt
10741 ttttatttga attgttgata gaattatgca ataacaatt ttaatatttc gttgcaaatc
10801 cttgctgtct atgaaaattt gcaggctatt aggaaacgag ttggcttagt aagaggcaaa
10861 gttgtttgcg attttcactt tctcagcatt ttgttttaaa acggtttggt atccaaattt
10921 gcaactttct tcaatcttac tctactcatt gttcttgagg cttttaaagc taacttttt
10981 gtgaaaatct ttggtatgcg gtgtattaca cgttttcct agttcggcct tgcgaaaaac
11041 ttttaagatc ggaatctttt gaataatttc gtgcacattg gacttcctcc atcccaccaa
11101 ttctgtaatt ttcaaactga tgtttcttca taaatcaatc agctgtggaa tttccaagga
11161 cgattgctac ccttttggag tcattccaaa gcccacaagc cagctcacag aagctgggt
11221 cggaaaaatc gaatttttaga tatttgaaag ctaaatcgt ttgcccacca attagttttt
11281 atgcccacgt ccagatttcg agatctgtat tttcgaaaaa gaaaattcgc gaaaataaaa
11341 acgttgactt tttctatcgt tttttttta tacctaattt attttgtaa ccttaaaaaa
11401 tacctgttta aaaatattta tcgtttgccc aacctttaa agtaactaat tttgttaagc
11461 cacctctcga aatattattt ttttcaatta ataacatttc attaccattt gataaaacgg
11521 ttttttaagaa tcgatatcat cctttaaaat tagatttgcc catactttaa cattagtttt
11581 catcattgt ctatcctta aattttttt tatttgcact tccattttc tatcgtttta
11641 tttaatactt aatttatttt tgtaacatta aaaaatacct gttcaaaaat atttatagtt
11701 tgcccaccct taaaagtaac taatttcgtt agcccacctc tcgaaatatt ttttttttca
11761 attgcaaaaa aaactaatt tgtcggcaac catgggcaaa caattccatt tatcaaattt
11821 cgatttccg accccagctt ctttgggatc caccgaccac ccaatactgc cacaaccaca
11881 attttaaaa atgtgttgaa aatgttgatt ttactatttg tcttgccaaa catatctaaa
11941 aaatcgtac caagctcact ctaatattag ctcaattaaa taatttaact aattaaatta
12001 aattggataa ataaaatacc acttttttc aggtggaggc gtaattattg gatctgctgt
12061 atctttctta attttaaaga gacgagcatg gcctgtatgg ctcggcgctg gatttggaat
12121 gggcatcgct tataggacgt gtgaaaagga tttaaattct ttaaaataaa gattattacc
12181 ttttaattca aataaaatat ttaattgagt aatgaaaata atatacttat ttagtgctta
12241 ttaatactga ggcttaaga gtgttgaatt atgtgatttt ccaaaaatat tccaaaaaag
12301 acaatttaat attataatcc atttgtgatc accattatcc gtcttgaaga gaaatctatt
12361 ttgcatgtta tacaccatgt caggatacga ttattttaag aagctctcgg agagctctag
12421 agaaagcagc tcttttgtac gctaaggctg acgacagagt gtgttcgaga agcgataata
12481 ttgcgcgaaa acgagcgata aaccactgca tgcatttta agtggaatcg ctcgaaagat
12541 gtcagagtga gagcgaagcg gacgactacg atataatgga acaaaacgca agtacaagta
12601 tgcaagccca aatcaacgga acttaaggag atggtggcaa acttggcaac gatggtccaa
12661 acggcatgct tgcaacaaca aagtcaagca caagggactg tggaacaaga aacgacacgc
12721 ttacgtcaga cgctggaatg atcgagacac acacatgcgc caaacgggat gcaaccggaa
12781 aatgtgctct catcgccaca cgctagaagc tcaaggtcaa ggttttacaa gcatcaaaga
12841 aatgatagga attctgccgg attttgatcc aatcaaggga tctatcacat cggagcaatt
12901 catcgcaaag gtagagcaac tacaaagcgt atacatgtgg acaagtgacg ctgtgctgtt
12961 tgcagtgcag cataagatct tgattttcca tgtttagtga gtacggccga tgtgcacagg
13021 gaattgatgc gtcgcaagcg acgcaatagc gagtcattaa ttgaatactt ttatgcgatg
13081 gtagctattg gacggcgtgc gagtgtcgat gaaccatcaa taaattcgta tatcatcaac
13141 gggcttaatt caaaagaact cacggaatca ttattagcga tgaacatacg cacttgttca
13201 gagctgctaa agtcgttgga aaatttgaga ttttcacaag agatacatca acaacaatac
13261 aacgcaatac aacgatgctg atggcaagat gaaagcagtt aaatgttata attgcaataa
13321 tttcgggcac tttgcagcaa aatgcacagt gccacagcga aggaaagat gttccaaatg
13381 ctctaagatt gggcataatg aaaaggattg caagttctca ttggaggcca acagtttgaa
13441 gcattcatcg acacgggcag tgataacacc ctaatgaaag aagcagcagt gccagatgga
13501 gcaatacggc agcccgagaa tcaaacgtct gaaaggcttt ggaggatctg tggtcgaatc
13561 gaaggagtgc attctttcag agtttgcata tggcaaactg agactcctca cgcaaattca
13621 ggtggtacca aacgaagtgc taccatatgt attgtatgta tatatatgtc ctcgtgggca
13681 gagatatcat ctgccacgat caggaaatgc tggttgcccg aaaattcagg atcaaccgtt
13741 gacagcagcg gagcaggtcg ggtttaatgt taacacggac attgaccccg accaccagga
13801 acaggtgagc gatctattaa agagctataa agagtgtttt gccgaagatt tgtcaaatat
13861 tggcaggtgc aaaaccacga gatggatat agaggtatcc tttacgaaag ccatcttggg
13921 gcggcgatat caagtgccgt ttgcccaaag ggagatgatg actaccataa taggtgactt
13981 actgaagtac gggataattg aaaggagcaa gtcaacgcat gcagcatcag caatattggt
```

Figure 14 (continued)

```
14041 gccaaaggca aatggagaac ggaggctttg cgtggactat cgggctctaa acgcagtcac
14101 tataaagaag cgatatccga tgccgattgt agaggagcaa ttggcaaagc tatccggaaa
14161 tgtatacttc acgacgctgg atatgacatc cggttattac caggttccga tggacaagaa
14221 aagcaaaaat ttgacggcat ttatggcacc agatggactg tacgaattta atgtcatgcc
14281 ctttggtctg gtgaatgcac cgatggtctt ccaagaagtc attactgaga tcataatatt
14341 aaaggaattc ctggatgctg ttaagttggc gggcttaacg ctgcgcccat ccaaatgcgc
14401 attttatgaa aacgaaggtg acctttttgg gtcatgtgat cacgggcaac gggattcagc
14461 caggcaatga gaagactaac tgcatcaatg aatatcaaag gccatgtaac gaaacagaag
14521 tacgcagatt cctgggagtt acaggattct tcagaaaatt tgtcaaagag tacagtatga
14581 ttgcgtatcc attgagcaaa ttattgaaaa aggatgtgga cggtatatgg tggaagatct
14641 gccagaccac aatgttactc agcgacgcta ttgtaacgtg atgtcaagcg accatatgag
14701 gccaatgtgt gccttaattc caaacctgga tatagatgag ccgatatatg aatataacga
14761 cgacgcagga atgtcaggag aggccggatg ttaagaggaa gagcatgaga gaggggagt
14821 tgcttgcgag atgccaggga gtgcggacgt gtgctcgctg ggtgaacgat gaaggcagat
14881 gtatactgaa gacttataac tattgtaaca cattaataaa agaaaagaat aaacatgaag
14941 gatcaacctg acacatttttt atggtcacaa ctgtcatata atactttttat atttaattac
15001 taaaaatcta gttttcacag ttgtcgactt cacaaaaatc gtccccatat acgtacaaga
15061 cacgctttga ggaatccata aaacaacctc aattcttgtc aagtgattcc aaaaactgta
15121 actgtgcaat atttcagaaa atatcagtgg agaatgggca caagaagtcg aattaatttg
15181 aaatgctgta tagtcttttct agagtggctc caggctctct cgaattttgt tagagagcga
15241 gagagcgaag agcgctcagc gaacagctct tttcaacgca caaagtgata gcagacaact
15301 gtatgtgtgc acgtatgc tcatgcattg taaatttgac aaaaatcttc aaagttcttt
15361 gactttaaat ctatattatt tttgatcaat tggcaccatg cgaaaaattc ttgttttgca
15421 ttgccttaac gttattatta tttgaaaata aaatagaaat agccaaatct ttgtacatat
15481 tatcacaaaa ataaatttca aaaatgactt tatgtaagaa tatttgtcat tagagtattc
15541 atcttgaggc gtgtgaaaaa ttaataaggc aatgattgtt gagtgcttgt gtccgcactt
15601 cgtgcctgaa gatatgaaca aagcaaagac actagaataa ttctagttat catatttta
15661 tgaaatttat gaaattacag tagttataat aatttctatt gnttttcctt taattaatta
15721 gtatatttat taagtcatttt gacttaaaat gatgtaacat taatattaaa agtgtttcaa
15781 aaaaatattt ctcttttaaa aaattggtca gatgagagac aaattagaat taaacataac
15841 aaatttaaca aacaaattta aaaaacttta aaaatataat agtcaggggc gcgaattttn
15901 aaaatttttt atttatcata ttgntaggaa attggcaaaa ctccctaata tgtcaatgna
15961 aatcgttctt catcagaatg attcggccga aaatcgcttn tagccaccac gcacacatta
16021 cgcgttctcg ctctggttta ctcagacaag caagcaaatc tatttttaga ttttatgctc
16081 tnacgggagc gacggaaanag nccatttggg ccgtccntna aaattgggtg cntngcccat
16141 cccattgtcg gtttgcccng ttcggcttct tggtatttct agtgtctttg gtagccttt
16201 gttccaatgt ggctttccca gtccggtcca agtgcnagcg taacccgagc atccanttna
16261 atccccngca tcncatnatt ggcatagtcc ancgttctca cgctggtcaa agcngctgcc
16321 cgcnatccca tgtgtgccta tagcntatgn atanatngta gcatnatatg cttcncatat
16381 tacggnttnc gcaagcattg ntacatncca ttcttggcac atgcatntcc gccatnnatc
16441 cnatttacct tttttgctta cgcttcagcg catgatttgt tgtgcatccc atnccgttct
16501 tttttcgttc ttttttgtac acatatnctg attagacatt cccgtttctc gcgactcact
16561 tcaagccgat caaatactct gtagtcagtc ttcagctgnc agttttngna tanagacgct
16621 ctctgaaatt attcgtgttt caatttataa ttggcttcag cgttgatctt tgtcttcgtc
16681 ataggcggat cctttattcc gactcgcant agtnnctacg taagtggcgc agtcggtagg
16741 atgatcctag ttgatgcgat attacaccta ttcanttctc tgtgtgtcat ccgctaaagc
16801 tcgtacaact tcaatatctc gcgtcggtaa atcggnaccn ttggttcann accaaaaaac
16861 ccccccctt tttganacca tctacntanc cnaaacccnca gagtgattgt gnaagtnccc
16921 nacttannat tgtatngatg gcnttcccgc atangggctt cgtgaattcg ctgagtagta
16981 aatccacaaa aggttactca aaannaagcg aaatagcaaa gtgtgcaaca catgaaaaca
17041 gctaaactaa gtgaaaacta aataaagta attacgacta agtgaactac aataacaaca
17101 gttaacctaa gcgataaaaa taaataaact taaccagaaa taaacgaaga ataataataa
17161 cagtgtaact aagtgaaaac taaataaagt taattacaac taagtgaacc ataataaaac
17221 agctaaacta agtgaaaatt gaataaaagt aattacaact aagtgaacta caataacaac
17281 agttaaccta agcgaaaaat aaataaactt aaccagaaat aaacgaacaa taataataac
17341 agtgtaacca agtgaaaact aaataaactt aattacaact aattgaacca taatattaac
17401 agctaaatta agtgaaaatt aaataaagt aactacaact aagtgaacta caataacaac
17461 agttaaccta agcgaaaata aataaactta gctagaaata acgaacaat aacaataaca
17521 gtgtaaccaa gtaaaaacta aataaactta attacaacta attgaaccat aataataaca
17581 gctaaattaa gtaaagactt aataaactca actacaacta aatgaatta aatgcaacta
```

Figure 14 (continued)

```
17641 agtgaaacat tataataata ataagtgagc gaacaacaag aaacccatca aacacataaa
17701 cttaaaacga agacacaaac caatagtgag aactcaaacc ctatcccaaa tcgcgaacca
17761 aattaaacca caaaccttat ctaagctacg aacaaacatt atcaaantaa tacgactnnc
17821 tataggggaga ggatctattg ttgtaaagta ttggcatcta cctaatttgn ccaatatctc
17881 acccattcgg ggaatgggaa atttgtcgtt aacagttatc tcatttagat tcctgtaatc
17941 gactaccaac ctgcattttt tttcccagag gcgtctgcct tcttggggac cacccaaata
18001 ggagaacaat aagggggactt cgatttttcga acaatcccctt gttctatcat ttctttaatt
18061 tgtttgttga cttcttggtc aacgctttga gggtacttgt anggtttacg gtatactggg
18121 tcttcgtgtt gagtttggat gacatgttta atagtactgg tgaaggtcaa attttcgccc
18181 tctttgtact gaatgtctct ttattcgtat aggaccttct ttaaacattc aacttcctct
18241 gcatttaagt gttcgagtct atactcgtta cattcgcgta actcattatt aatcgcgaag
18301 ttggctatat cgntgtcaac ggacatggga tcgagatgtg ttacatcatt gtccactgtg
18361 nctttaacaa catttgaaat gaggcatttg ggtaatgcan tctccttctc ttgatgctga
18421 tgctttggnt taaggcactt angtgggnnc ntaaccttttt gcattnnngc tttgattctg
18481 ccactaaagc ggaatcatnc tcttggtttg ngtcaangcg tntggatacg gcnccccttt
18541 ttnttcatan agaaacttaa atctntngac cctagtctta ctgaattcnn nnnnnnnnnn
18601 nnnagacgaa actcnactt attttgatng ccgagtcccg agctcgaatt cacatttatc
18661 aagcttcaat tttaaaattt gcttctgtag ctttgaaaaa actaattgta tgggatgttg
18721 aaaaaattat tatatcattc aaatatacta aacagtgttt gttaggcaaa tgtcaaagga
18781 tattattcat gcacctttga aaagtagcgg gtgcattcct aaggccaaac agcattcgaa
18841 ggtattcgta atgaccgttt tgatggaaa atgcagcttt ggatattgat tctaggtcca
18901 tttctatttg atgaaatcct tttgccaggt caatagttgt aaaatattga catttccta
18961 atgtaccaag gatttcgtcc attgtttgct attggatatc tgtcgggaat agttatttca
19021 ttgagttttc tataatcaat tactacgcta tactttattt taccacaagc atcagttttt
19081 tttttggtac tatccaagta gtactattgt atggtgaatt actatcccta attaatccgt
19141 aatttagccg tttccagtac ttggttttct actttaattt cgtgccgttt gagcaaaagg
19201 ggtactgatt tgaataaatt ggggagttat gtgttgtatt tngtacgtat ttaaatggna
19261 tttggaaatg gtnaatttgg cttcttaat atatatatnn atatattata tattataagg
19321 catttggtat gtgcaacctt tgtatgctat ttctatggat tcgtgttgtc cggggctgtt
19381 gaccgaataa ttttcgcttg gttcagagtt attttgattt tcttggtcat taattttggc
19441 gggttgaacc tgttgttgct cttcattaat gaacccatga ttttggtata gattgtattg
19501 attgtggtta taatactggt gttcataata attaagttaa aattgttcga agttttgaag
19561 tcaaatttcg tcaatagaca ttttggtttg ttcactgtcc gatggtctta gtcgtatttt
19621 tagatgtttg gatgtttaga tgttgttttc gttgagggta ggtatatcct ctgaaatgtg
19681 ctatttgagg attttgggtt ttgttgggat atcgtgggaa aggatttttt ttaataattg
19741 gttatgtgtt catgtattgg acgggtctga ataattagg tgccggtcac ataggttggt
19801 tgttagtcat ctgtcgtgta ttggtgggtc taaatggtgg ttgcatgcat tgtaaaattt
19861 ggttggaagg gttgagaata ttgtggataa cttggtcgat attgagtttg ggtattgcta
19921 ttgaatttgt gtgatttaga attttgatta agattaaagt ttttatatcg attttattt
19981 aatttaaaat taatatgttc gtcataaatt ccctcatttt ttgcaataga aattaaagat
20041 cttacgtcat gataagttaa aatagtgaag aatagtattg gtagtttat atttatttat
20101 ttaataaata ataaatgtaa caaataagaa attncggttt gttacctttc aggtgtaatt
20161 tcgaaatcaa catttgacgt cgatttccgc aaaaagattg ggnnnnnnnn ngaattccag
20221 gaaacnctan ntganttcaa gtccnggccc gaattctcct agatttcctt tgttaggtgt
20281 ctccatgaag ttcacnagta gtttgtagtt cggtgattgg agcttaaatg ctgagataag
20341 tctggatttc agggttggcc aatcttcgat gttcggaagt cccatagatg gtgctacttg
20401 tccgtccaag tttctttcga tggctccaag taaaatcctc tgttgtcgca catcattcgt
20461 ttggtagagc gaaattacgt agtccaatct gctgacgaag gtgtgggagg gtttctggat
20521 cacgcttgaa tggcatgatg ttttttagcta acgacggtct tcagggaggt tgttgtcgct
20581 tagcgcaacg atttgggggtcg cggcaataat tggttgtgcc actgtaattn tttattttt
20641 tattatactt tcttctttgt ttttatttat taaagttttc cgacagttttt caggttataa
20701 tctcttataa ttttaaaact aatatttaaa atttggaaat tgcaaaaatt atatttggga
20761 attttagtt tattttaact tgttttaact tcttgtagtt tttatttcga ataataattc
20821 acttatgttt gtattgttta ttttaacttg tttcacgtat tagtttttat ttcgaataat
20881 aattcacgta tgtttgtatc cttaaaatgt tattggtctt ataggattgt ttaattttct
20941 tctttttttct tctgtgttgg acaaccgaat tggatttata acccaagttg aagttaaata
21001 agagtcagtt gcgtaattaa ctgcgagaat tacggattat acaatttaat ttattttcca
21061 ctcgtggttc tgatacttt tgtatcctt tgcgccagta agatatttgt tatattttg
21121 agtcgaacta atgtcccgtc agttgaactt ccttattcgg atatcagctt aagactaaat
21181 gatagtgaca aaaatctttc ttccccttt ccatttttcct tgctctttta tatgctactt
```

Figure 14 (continued)

```
21241 ccaatgtgaa tttactttcc ttagcatagt caatggtttt ttagcataaa atgattcttt
21301 gttgatggtt gtaagaaaaa atgttggtaa attgttctac caaatactat ttcgtatgga
21361 caatatttat gtgccatagg agggtcaaa gacactataa taacaagatg cgtaacggcc
21421 atacattggt ttggccaaag accctagaat aacaagatgc gtaacgccat acgattttt
21481 ggcacacgat ttttcgccg tgctctaga attatttcat ctaaggaaat tattttgttt
21541 tatnaggant cgaaagctgc aaatcgcagt ttattattgg cggtctgaat ttttaagtt
21601 tcaattagca tgtatgatat cgtaagaaat ttgtttgtgc taatatactt tttttaaaaa
21661 tgttttgaaa gcccgagccg cggttagcgg ccaaaaggtg ccattcagga tgacaactgt
21721 ttgtaatttt tggtaaagaa tggccaaggt agggcgggca ttacacgatc ctccaccaca
21781 cctgaggatc gagcggaagc ttgtagggta aaagaatcgt tctctccgtt gtaagtgtcg
21841 ttgatggcga tttgccgccc ttttcttaat tggaaatctt aattgttcca ggacaaggac
21901 caccaccccc acataacccg acaaggagct gctgaacttt cgccgcgtgc gtactggaat
21961 atctcacaac aattaaataa tttataattg atattgataa tttctctgtg tgctctttca
22021 ataatttcaa aatctaaatc gctatcaaaa taaatgctaa tgnttctatg aataaaatga
22081 tcttgtaaaa tttgtgtggc cttttcaagt ggcattaaat catattgaat tgtggtaatg
22141 gagctccgaa tattattgga atgctctaca ttatttttat tgcttctgca aatgttgagt
22201 atctacactt aagaaggat ttcttcaatt ttactggaat tttcattggt tttgatataa
22261 tcgatttta attgttattc gtttaatcta gttctccatc ctttgtaact tatagcattc
22321 ggttcccttc tccatctttg taacttatag cattcggttc ctttaaagta tgaagtcatc
22381 taagagggtg atggtcacca gcaatgacaa actgtcgttt tagtaaataa agccgaaaag
22441 cttttgttgg cgagtaattc ttttcgata tctgtaattt aattcgtgtt cattaagtgt
22501 tctgctaata aggatatgg gatggccatt tgagaattt actgctcaaa gggttaattt
22561 actatcacct gtggttacgt tttttgaatg cgcctctatg tagtcaaggt tatgtgcatc
22621 tatctttgca ccttttttta aacatttggt cattggtttt ggtatgtctg cggtaatttg
22681 aaataaattc accataataa ccggttaatc caaggcaagg tctgatttgg aattggatgg
22741 ctgtcgttta aaggnagttt agtttatac cgttagggt tacgacggac aaganggtat
22801 gccctaaaag gaaacggagt tnnnnnnnnn nnngaattca catttatcaa gcttcaattt
22861 taaaatttgc ttctgtagct ttgaaaaaac taattgtatg ggatgttgaa aaaattatta
22921 tatcattcaa atatactaaa cagtgtttgt taggcaaatg tcaaaggata ttattcatgc
22981 acctttgaaa agtagcgggt gcattcctaa ggccaaacag cattcgaagg tattcgtaat
23041 gaccgttttt gatggaaaat gcagctttgg atattgattc taggtccatt tctatttgat
23101 gaaatccttt tgccaggtca atagttgtaa aatattgaca ttttcctaat gtaccaagga
23161 tttcgtccat tgtttgctat tggatatctg tcgggaatag ttatttcatt gagttttcta
23221 taatcaatta ctacgctata ctttatttta ccacaagcat cagttttttt tttggtacta
23281 tccaagtagt actattgtat ggtgaattac tatccctaat taatccgtaa tttagccgtt
23341 tccagtactt ggttttctac tttaatttcg tgccgtttga gcaaaagggg tactgatttg
23401 aataaattgg ggagttatgt gttgtatttn gtacgtattt aaatggnatt tggaaatggt
23461 naatttggct ttcttaatat atatatnnat atattatata ttataaggca tttggtatgt
23521 gcaacctttg tatgctattt ctatggattc gtgttgtccg gggctgttga ccgaataatt
23581 ttcgcttggt tcagagttat tttgattttc ttggtcatta attttggcgg gttgaacctg
23641 ttgttgctct tcattaatga acccatgatt ttggtataga ttgtattgat tgtggttata
23701 atactggtgt tcataataat taagttaaaa ttgttcgaag ttttgaagtc aaatttcgtc
23761 aatagacatt ttggtttgtt cactgtccga tggtcttagt cgtatttta gatgtttgga
23821 tgtttagatg ttgttttcgt tgagggtagg tatatcctct gaaatgtgct atttgaggat
23881 tttgggtttt gttgggatat cgtgggaaag gattttttt aataattggt tatgtgttca
23941 tgtattggac gggtctgaaa taattaggtg ccggtcacat aggttggttg ttagtcatct
24001 gtcgtgtatt ggtgggtcta aatggtggtt gcatgcattg taaaatttgg ttggaagggt
24061 tgagaatatt gtggataact tggtcgatat tgagtttggg tattgctatt gaatttgtgt
24121 gatttagaat tttgattaag attaaagttt ttatatcgat ttttatttaa tttaaaatta
24181 atatgttcgt cataaattcc ctcatttttt gcaatagaaa ttaaagatct tacgtcatga
24241 taagttaaaa tagtgaagaa tagtattggt agttttatat ttatttattt aataaataat
24301 aaatgtaaca aataagaaat tncggtttgt taccttcag gtgtaatttc gaaatcaaca
24361 tttgacgtcg atttccgcaa aaagattggg nnnnnnnnng aattctccta gatttccttt
24421 gttaggtgtc tccatgaagt tcacnagtag tttgtagttc ggtgattgga gcttaaatgc
24481 tgagataagt ctggatttca gggttggcca atcttcgatg ttcggaagtc ccatagatgg
24541 tgctacttgt ccgtccaagt ttcttcgat ggctccaagt aaaatcctct gttgtcgcac
24601 atcattcgtt tggtagagcg aaattacgta gtccaatctg ctgacgaagg tgtgggaggg
24661 tttctggatc acgcttgaat ggcatgatgt ttttagctaa cgacggtctt cagggaggtt
24721 gttgtcgctt agcgcaacga tttggggtgc ggcaataatt ggttgtgcca ctgtaattnt
24781 ttatttttt attatacttt cttctttgtt tttatttatt aaagttttcc gacagttttc
```

Figure 14 (continued)

```
24841 aggttataat ctcttataat tttaaaacta atatttaaaa tttggaaatt gcaaaaatta
24901 tattttggaa ttttttagttt attttaactt gttttaactt cttgtagttt ttatttcgaa
24961 taataattca cttatgtttg tattgtttat tttaacttgt ttcacgtatt agttttatt
25021 tcgaataata attcacgtat gtttgtatcc ttaaaatgtt attggtctta taggattgtt
25081 taatttcctt cttttttctt ctgtgttgga caaccgaatt ggatttataa cccaagttga
25141 agttaaataa gagtcagttg cgtaattaac tgcgagaatt acggattata caatttaatt
25201 tattttccac tcgtggttct gatactttt gtatccttt gcgccagtaa gatatttgtt
25261 atattttga gtcgaactaa tgtcccgtca gttgaacttc cttattcgga tatcagctta
25321 agactaaatg atagtgacaa aaatcttct tcccctttc cattttcctt gctctttat
25381 atgctacttc caatgtgaat ttactttcct tagcatagtc aatggtttt tagcataaaa
25441 tgattcttg ttgatggttg taagaaaaaa tgttggtaaa ttgttctacc aaatactatt
25501 tcgtatggac aatatttatg tgccatagga ggggtcaaag acactataat aacaagatgc
25561 gtaacggcca tacattggtt tggccaaaga ccctagaata acaagatgcg taacgccata
25621 cgatttttg gcacacgatt ttttcgccgt ggctctagag gtggctccag gctctctcga
25681 attttgtta gagagcgaga gagcggagag cgctacagcg aacagaccaa aattgctctc
25741 tttccgctcg ctcccgctga gagcataaga aatctaaaaa tagaatttgc ttgcttgggt
25801 gagtnaarwm aasagancga gaacnaaagt catatcaaag acactagaat tattctagtg
25861 ccgcaagatg aatactctaa tgacaaatat tcttatataa agtcattttt gaaatttatt
25921 tttgtgataa tatgtncata gttttggcta tttcaaatct attatcaaat aataatacg
25981 wwnwggcaat gcaaaacaag aattttcgc atggtgccaa ttgatcnaaa ataatataga
26041 tttaaagtcn aagaacttct aaggtgaagg gcatatttg tcaaatttac aatgcatgag
26101 cntacgtctg caccgtctgc acacatacag ttgtctgcta gcactttatg cgttgaaacg
26161 agctgttcgc tgtagcgctc tccgctctct cgctctctac caaaaattcg agagagcctg
26221 gagccacggc gaaaaaatcg tgtgccaaaa aatcgtatgg cgttacgcat cttgttattc
26281 taaggtcttt ggaggggtag tgttgaagca gtattcaaag tattgaagcc aaatgtccca
26341 atcagtttg gatcgtatat atttactaag agttctatgg cttctttcaa ctactccaac
26401 tgtctggtaa tgatntgtta taattttaa tgatatattt tttattttaa agtgttttat
26461 tcacagatca gatattacta aattcttatg tctgttccca tgtccgtaat gaacgttttt
26521 attggaccgt acttcagaat aaaagattca aatatcgctt tggctacggt atttgcattt
26581 ttgtttggta tggtatggct actaagtatt ttgtcatgtc acatatgaga gtgactgcat
26641 atatgtacat taccattc cgattttgt agtgggccaa ttgtatctac aaccctatca
26701 tatgcctgtt ctagtgtttc atttatcgtc attggtgttt tgatatgtgt aattattctt
26761 gttttggaa cgatggaatt tttttgtgta ctctttatg tacttagaca tatttttcca
26821 aaaatacaat aatatcttg caccttgacc aaggttttg aaatgccagt atgtcctcct
26881 catcatgttg tgtagacgtt atagcttctt tttctattt ggtcaccggg ctgagtagcg
26941 ctactcttaa tacgttaat tgttaatttt aatttaatt tttcattgcc cacattttg
27001 aaagtctatc gaaatattt caaagttatt ttcccacggt gccattttaa ctgtcttgat
27061 tttgtgtata ccggcctggt tttcaagcct ttggaaaaac tgatctaaat cgagatttcc
27121 aataggtaca aatcaccaat tttataactt gcaatgtttt tctttccatg tttgaaaaaa
27181 catatcatat ttttcagatt gctaatgaat gtaaatacgt tgggctttga ggtttttatt
27241 gattactttg gcaattctat tttttcattt tcttctcttt cgcaggaatt ttgtctacat
27301 tgatatctgg tagtgagtat aggtatttt cggttttat ttttttctca ttgaaactag
27361 gtatgttaaa ggtctctgtg gtcactttga actaaaaaat gcctaccata tacagtttgt
27421 caagaaactg tttacacact gtgaaataag ttgaattttt gactttaaag ctaaaataa
27481 agggtnttt gcttaattaa acgcaatttt tttataaaat ataattaaac aatatttatt
27541 ntacttataa atnaaacac aaattaaaaa tattaaatat acnagaaaat aaacaacana
27601 ttccaagttt acacactttt gagactgtca agaaactctt tacacaaaac actaaatcga
27661 agtttaatcc taaatttttt aattatytta ttaaaatttt aaaagtttng gtatgtarya
27721 tgtttccccm ttkgctttag ctacaagttg aagcctttt ttcatggatt ggacaagttt
27781 ttgcaggtca tattcaaacg ggatcttttc acactcttcg actattacag tcataagctg
27841 ttgttgtgtt ttaggtccct ttttgccacc ttcttcttta agtaggtcca caaattttca
27901 atggggttca gatcaggact ctgaggggc gtatcgatca ctttaccaca gttattaagg
27961 cgccaggtgc gtacattgca ctctttatgt ttctgatcat gtcctggtaa aacttaagat
28021 ntggcttgtt gttgctaact agaccgaatt tttntgcact ggccttcaca tttgttttt
28081 aacatttcta gatattgcac ggcagttatt gtgctctcaa ttaaggctag ttttcccact
28141 ccacggctgg tgatacagcc ccaaaccatc agtgacattt ttccaaattt tatcgttgga
28201 atgatatttt gttttctag cgcactcaac ggtttgcgcc atactctgct tggcccgtcg
28261 ttataaaaga gcatcatttt tgtttcgtca caaatatga cgtcatccca gtactcttcc
28321 gcatgatcca tcatgctcac agcgaattaa tgaccgcttt tccatattgg catctgatag
28381 caaggggttt ttccttgcaa atcttgaaga gtacctatgg cgtaggatga cttggcgcac
```

Figure 14 (continued)

```
28441 agtttcgtgt gacacagtta ggtggcattc ttgcctgata tccagagcaa gtgatctgac
28501 cgagattggg gggtcgcaat cactattcgc ataataaagc ggtctacacg cttttttaatt
28561 ttaattttcc gcccaccacc actcttaggt tcaagcctgc cctcttttttc cgagcctttt
28621 aaaacattgt agacggtctt acgggataca ggaaacattt atactaattc tggaaaagat
28681 tttcccaact ggtggttata gtttattaat tgggtaactt caaaagttaa tctctttcca
28741 ngcattttat taaattaata attcgcttta agcacgtttg gatcaagcaa aatttcacaa
28801 gcaaagtna caaaatttna atagaagcgt tgtaaaaagc aatgcaaagc caaaataacc
28861 gaaaaatcga gttcgttcta agaaaaagaa cnaacaaagt aggaaaacaa atgtggtaag
28921 agtttcttga cagtctcaaa agtgtgtaaa cttggaattt gttgtttatt ttcttgtata
28981 tttaatatttt ttaatttgtt ttttgattta taagtaaaat aaatattgtt taattatatt
29041 ttataaaaaa attgcgttta attaagcaaa aaacccttta tttttagctt taaagtcaaa
29101 aattcaactt atttcacagt gtgtaaacag tttcttgaca aactgtatat gtgtcggcga
29161 gacagcagtt tcagccattt catttattca cttcgcgatt tgtgcgtca gcgcagcaag
29221 ttccgatcga cgtcagcagt aaaacttcac tgaagggatc ttcttacatg tcccttcttc
29281 atcatattct ctaatgtcta tacacactgg cgtgtgccac attgtcatct cgttctaaca
29341 cactatttat gaccactcga tcggacctca ctcagctgca gaggctgttc gtgcctctgc
29401 cgcagcgctc gacagaattt taccgcaata ttacaattcc atcagaatat gaaatcacag
29461 aaggaatttc tggaatgcga aaagtcgcgc tccgacacgg ccttcctgac ctttcacacg
29521 tcctcgtgtg cctaatccac caatcaagtc caagtcacac aacttcgtca acttaagaac
29581 aattaatgac nacnagtaat aatcagtaat tatttaattg gcaattcatc tcatgactgg
29641 ttttctttttc caaaggacat ttccatttac atatcaaaac tttnaactat ttaccatttc
29701 catgacttta atttctcata ataacattgg cgtggcttct ttnacaccaa tctttttgcc
29761 ccggcataac acttttggcc ctgcgagtta gctggtatag tgcagtcatc atctcttgan
29821 tnccgccata acacttctcg tccnggcgng ggagctgtta tagtgcagnc atcatctctt
29881 gacccccgcc ataacacttc tcgtccctgc gagttagctg ttatagtgcg gtcacacgcc
29941 attctattca tgacgttcgc caaatgttnc ctttcttggg cacgatcact agtgccatct
30001 ttaaactctt ttccctcttg ggacacagat gtacgatcac tagtgccatc cctcaactgt
30061 tntctctgnt gggagtcacc attacattca tgcgaatatt natatgtncg cttgataact
30121 aacgacttca aattgngtcg atgaccatct agtacattaa tcactcgatg atactcctca
30181 cttaacacat gaactcatac cgaactacta catcctttcg cttggcnncc ttgcttgtac
30241 gctcattngn tnncaacctg cccattngct ctgctggcat ctgnagctat tgaaaacaac
30301 tcaatcctgg nnggngaaca aaactcacgg aactngntgc tgacaaagct nctgccttga
30361 tccactatga tgcgactggg agctctaagg aaagacatac tngactcttc tatagaatcc
30421 gctggccatg ttaaaccaaa ngaaaaaaaa tnttttcccnc nccgcaancg ntcntttgat
30481 ccaaaatcca ggaancaatg gaaantgagt cgatatgggg cgcccttgac cactttnatt
30541 tttaattact ttaaacgaat ttccaatgcg cnttatttgg tatcccagtt acgaaactat
30601 cggcatactt ttccaatata tttcttaatt acatttatca ttatcgctta cttctgtatt
30661 gatgtcaaaa agtttttcca aactattctc atgtgcatta ttttgaacgg cattgataac
30721 tttggatttg tacatgctaa atttattaga tttaatcaat aaaacgaaac caagctctaa
30781 tatgtcttgg ccaatcatta tgtcgtactt taaatagttg tccactacaa catgaaacaa
30841 aatatctaaa ttcaattgag acatttggac tgtttatagt atttgcaagt ggctcttaac
30901 tacattgtca ccaattcctc ttaaaacaac taggttatta attctcttgc cagccaattt
30961 gttacttaat ttatccttta ttaaagaaca ttcggcgtcc gaatcgaaaa aaaaatgaaa
31021 agggctcacc caattgaaaa agtggactgt tttttcaatt gggtgagccc tttccatttt
31081 ggaaggaggc aggcaccaca atgtcattaa cgtctgtgaa gttacacta gggcagctga
31141 aatagtgaag cttttacaa acgccctgat actccagaga gtcctcagct aggttcaact
31201 tgactccggc ctgtgttaac aggtctaggc ctataatagt gtcgaacgag ttgagcgaat
31261 tcaataggaa gaatggggag gtgtgcttga ataccttcat aaagcacttt tgcttgattt
31321 cggtggagcc atgtattgag ctcaccgaga acggactggc gaccggcatt atatttttta
31381 gctctttttac ggacttaatg taattatttg ccgcgccggc gtcaattaac atctttaaag
31441 ttctcccagc caaccgtcgt cgcttgaagc gttctcattg tcactgtcga tatcctcgac
31501 tgcagccttt gctgcattct catattcctg cttggggtct tttgcgttag ggtctttagg
31561 cttgggatttt tcttggacaa cattattgat gcgctggcgt ctgggacctg tcgaacggtc
31621 tgaggaattt ctcccttat aagtattggg cccattttgg ttattcctat tgtattcggt
31681 ccgctgtctg aacctggatg acgcgtagac ctccatgggc tgangtgctt gcgcctggtt
31741 gtcattatta ttctgcggaa tggtattacc ttttggtcgc cagacaaagt gcgtgcttct
31801 ctcctggcgt tggtctctcg ntgtctttcc cttgtctacc ctggaaacng ctcttgccgt
31861 tgcgctcgtt cctctatacc ttggcgtana aactcgcgaa catgctcctt tcaatgcttg
31921 cttncgcttn tttggccaaa ccnaggcana tgcaagtccc tgggtttagc cgggaagacc
31981 acagctctaa gggacttttt gaggcccgnt ntggnggcat gcagggcatc ggctcttant
```

Figure 14 (continued)

```
32041 tcagcgttca gtaagtcagc gccctcttgc tcgtgtgtca tcacaatttt gttggtgacg
32101 agcgtcaatt ttttttcgac ttcgtcgtag tattgcatca atggcatgtc cccttgcctg
32161 accatctcta ataccctgcct cagtaggcgt acggatgtct tgtctgagta cgtgcagtct
32221 aacctagcca aaatggcatc gaaattcaac ccagtattgt gagatagtag tagggctcca
32281 gctgcgcctc gaattttgtt tcgtaggatg gctacggctt ggtaatgagc actggtaccg
32341 ttacagggct tgaatagggc gtaagcgtat atggcccgct tgcctncagg cttngccaag
32401 acaattgggc aacagttaaa actcttcatt taaggtccct aattacttat tttattttta
32461 tagtgtttgg taattcctaa gaatatttct ccaccctgtg atgttaagat acaaatatga
32521 tgtacggatt cttcacttaa taaataataa ttttaaaaaa aacttgtttt ttgcttttcg
32581 ttttatttt tttttttagag acacttgatg ggcagccgag taaatagctt gtcaaactta
32641 catgttctgt agcgtaacta ccttgttgac tatttgcggt ccttgatgaa gttgggcgtt
32701 atgtagatat gcatttctct gctgtgtcca gagttatgta agatatgtat ttctcttctg
32761 tgtccagagt tatttctctc ctgtgtccaa gagtcttcct tctcacactc caaatgggac
32821 acgtcggact tctacaatcg aacggtctca gcatagagcg ctgaactcca ttatggcgcg
32881 tcagcattac tttgcgtggc tacttagttg ctaagggaat gtgaacttga tggtttgtta
32941 acttgtatgc aaaattcttt gctaaaatct gggtactgaa gaagtatagg tttcattaat
33001 tcccttttaa tatacttaaa tgcgtggcgt gattttctca taacattttg atttaatctt
33061 ctataatgat tataaaatgc aacgaatcgt ctagcttcgt ctgcatttgc tggtttggga
33121 tagttttga ttacgtcgtg acctaaatat gtaacctttt ttataaggga agtacatttt
33181 tctggatgga gttttagctt atgctgtatg cataatttga atacatcggt taagttcttt
33241 accatatgcg tctcagaaca accgattact acttaatctt ccatttataa aacgcttgca
33301 aaatttgtaa gcatgcgaac gcaagtgtca tcattctttg taaggaattt ggtgctattt
33361 ttaaaccaaa tggcaatcac gtgtagcggt attcacctgt tgaagctgag aatgatgtta
33421 tattacttga cctttcttct aattcgattt aatgatcaag aatatcttct attcttggaa
33481 gatggaattt atctgctagc aatttcttgt ttacttggcg atagtcaact actagtctcc
33541 atcgcttttc cgccgactta ggcattgact tcttgggtac taagagaggt gggcttttat
33601 attctgatac agatggtgct acaataccct cttctatcaa ttggttaact tgcctttgta
33661 ttcctggctt acgactttct ggcttttat agtttttat gtgcttctgc aaagctttgc
33721 cttctttgtc ttgtgtgtcc gtgacaacgg acaacgtgcc ggctcgaatg gaattatgat
33781 gttatcgtcc ccgggttaag acaacgctcg gcctgggacc acctttgccg accactgact
33841 ccactgtccc tttcaaacac tacaggtccg tgtcgtgtcc tccgcaggac cacctgtggg
33901 ctgaaatggg ttcaggatgt tatgtggcag ggtgtgtcgt ctacgggtta aggtaacccg
33961 taccacctca gcctgggacc acctttgctg acactgactc cactgaccct ttcaaccacg
34021 ccaggtcctt gttcttccac tgcaaggatc gatctccacc tcgaattgct cgtccttatg
34081 tgtgctttcc gacactttct gctgtccaac gctttcacag ttcgctcttc actgactcct
34141 cctcgcgttc taactcattt tctccttcgg acggtttagc atccacctt agactgcgtt
34201 ccttttcgtc cggtactctt ctcgactgtc cttctcgctt gttgggactg gctgccccga
34261 gctgcacttg cgtcgtccct ttataggccg cgggatcccg ttatttcccc ttttgcgcaa
34321 gtctcgattc caacgcggta ccggtagttc acgttctctc ctcaatgccg gggttcaagg
34381 tccattaatt accgttcaac ctgaccgacc ttgactcttc ttgcattcca gccgtcttca
34441 ctgctgctag gccgctcccc tgcaccggaa tttgtgggga gttttaagac tctttacaaa
34501 acatcgatct ttcatatgac ttcagatctt gcaggcagaa ttaatttatt ttcaaaagaa
34561 tttatacgtg tatacgtgtt tatgttcctg atgttattgg ccctactgt gaaccaatca
34621 tcctggtctt ggaatttcaa aatacaagtg tacttcttta taagcccaa gccaaatata
34681 ccatcacctg gtgtatttta ttgattattt ctgcactta ggagtaaaat atcaacacct
34741 ttatctatta atgtcaacat gaataatttg tccggggtat tttggctagg gggtttcttt
34801 tatttctgga tgcgtggaat gtctgtcata cttagcagtc ttacacacca aacactgact
34861 cgcgatagct aaaactttt cctcatttta ggaatgtata tctcttcgga caactgagct
34921 ttattttcca cagcatttct gtgtgctctg ttatgtgtcc taagtatttc ttcctcttgt
34981 tcggcttcgt taacaaggtc tttaacttta gtttgacaga atctaatctt gaaacctga
35041 aaatggatgg ggtagagaat ttgtattttc cccattacat cctcagatgt gaaaattcca
35101 ttaatcacgg atgggttaag atattccttc aaatctgaca agagacatc aggtgtgaac
35161 aatttacgat ctactaaata cctatcgaat gtagggaatg gaatgctaaa tgagtaattc
35221 tctgactcgg acttcctgaa gaaaatttga ttttaaatg catttatcgg gatttgaacg
35281 ctacgtatca acccatggct cgaactgtcg gagctgtgca ttggtaaaag ctactgtgtt
35341 aatctgttcg actgtcggtc ctttggacaa aacgtcgggt acagtatttt ctttgcctgg
35401 cttatagaaa atctcgtagt catattcctc aaggtatgct ttccatcttt taatcctcgc
35461 attctcaatc caactactga gagaatggtt cagaggctga tggtctgtaa agattttacc
35521 tttgctttac cggaaaggta agttttagc tttttttagag cccagataag aagaatctga
35581 tgaaacccac ttttcagatc gagcactgag aaaatcttgg tgctccaatt gtgccaacac
```

Figure 14 (continued)

```
35641 ttcattaatg cagggatatg gtatctgtac gctactggta ccatattaag tttccgggag
35701 tcaattacca ccctggaatt tttctctttg ccaaaaggag tcgagttttt tttggggaca
35761 atccacactg gtgaatgatg ggacctgagg tcgaatgatt ccatcgggta aaaggggtcg
35821 aatgatcgca tccgtgtaaa agttcggaaa tttgtttgtg tacctcgtct ttaagagaca
35881 ttgggtactg atagaatttt gagtatattt ggcgtatccg atatagttcg gattgctgcc
35941 cttacacttg ttgtgtaggt tagtttttga ttcgggtctg cgaagagacc tgaatacgat
36001 atcaattatt ttattcaata tcattctctg ttccacctct aagtgtttta ttctcggact
36061 aattgtgcta acagcctcga actgtttttc tttgagaaca actcttttcc cgttttccag
36121 tgtcatggtt aggttcttca aatcaatttg cgctcccatt cccttcattg tgtctttgcc
36181 aagtatggcg tcaaaagtct tcagcgttgg taacaaaaaa aatttttattt cgaaatcgaa
36241 aaaaaactct tttgtaatgc gatattttta catcaccgcc tggagtatca gctatgtaag
36301 gcttgttatt tggtatcgcg ttcgtcacca aattgggctg gatgtaattt ttattagagc
36361 ctgtgtcaat caacacccctt aaaacctttc cactccccac tctacattcg aagtatggta
36421 gtgaggagtc ttctactcta aaaatgcaa cacgtggtct cgttgttcgc tgtccaaatt
36481 gtctatttgt ccatcacagt attcatttag tgtgccgttt atattgttct ggggttcata
36541 atcttgcatc gaccgttgat agcctgtcat gcttgaactg gacccagtta cttcaatact
36601 tggctgtctc atgttcactg tttggatgtt gtagttcttt tgtcgtttgt ttatgtccga
36661 gtgtggtcta ttcatataat taatgtttcg cgtctgtaca ctgccgtcca cgtcccattg
36721 gttctggtct tggttgtggt ttggtcgcaa agggacgggg tggggcattg tattgttgcc
36781 attgctgttg atagttttgt cggggtggaa tgaacggtgc attaccgaag ttagacacgt
36841 gttgccttgg cgccgggaat ggctggccta aatattgtgg aggtctcctc atgggatgtc
36901 gtggagggac cggtggaggc tgtcgatnnc caaaggcatt cgacggctga aaattgcggg
36961 gtgccggaat gggttttttcg tttcctctga aactcgactg ttgaccctta ttcgccgcat
37021 gggttggtga cctgaanagt ttgattttca agtttaaggc aataatgtaa agctgagggg
37081 agatcagctg gctctttttat tgccaaannn cgaggtaaat ctcctcgaag gcctctgata
37141 aaagtatcca gagcttttttc tctgtacatt tttgtaacaa agtgctcgga ttctcggctc
37201 atttgcatgc agccgacttt atttagaata agcgacagat ttttgtagac gtcttggtgg
37261 aagtcttcca ccgactgctg gtggccttga accaaagttg acatttggta ttccaaggta
37321 gttatgtccc gtttatctgc gtaatgcaga gtgagacatc tcgacatggc cttccagtcc
37381 agcggaatgc tgtaggactc gagtgccaca tcagcacttc caacaatttt atttcttatg
37441 gtatgaagta taccataata ttttggagta cccacaaatg gggtataagt ctccatgatt
37501 ctatcaacgc tcttttttcca agaccgaat tctgctggat ttccagagaa ttccctgatc
37561 gatttttacga tatcaggcac cctgtcaaag tccgctaaat tatttctgta ttcgggctcg
37621 ccgacctggt cgcaccttga tgctcacgta cagaaagtca agagtatcgt tantcattgt
37681 tttatcagcc cnggtaaact tggcccncng tttgccaatt aatgctgtct actgtnngac
37741 actcatgtct acgcgatgct gttcagncca ggtcgggtct tttctgaggg taaaggtctt
37801 ctcatttgaa ctgaaagctg agggtcttat tatattatta gggttttccca tgtgggcttt
37861 aaattcgggc ccaaaacntg cataaaacaa gcntaaacct aaacaaattt gaacttaaca
37921 aaagttgtgg gcagaaaata tggaatgcat ttgcttactt ttctttcgtt ttttttttta
37981 attttgcgtg caataataat ttagcttgcc gcggcaattt tgctttcaga gcattgtacg
38041 agaaaagaat tgtttctttc agaagatctc taggaactgg gttgaaaata taataaaata
38101 atattaccaa taataataat ataataataa taatataata ataaaaatat aaaaataata
38161 atagaataat aataatataa tataattata tatatatata tagtgacata tccataagtc
38221 cctaagactt aagcatatgc ctacatacta atacacttac aacatataca ccccaataca
38281 acatacacta ctccggatgt acccaacaga tccagaaaga ataagattgt taaaaaaacc
38341 ccattctaga taagtcaccc tggtagacta aacatccgcc cctaatttaa acaattcctt
38401 gcttaagcct caccccatcg tcacattccc acgttccaatg ctcggacccg aaatcccgaa
38461 aaacaaaagt atcgatttca ataaacaaat tataagaatc taagagcact tgtatccaag
38521 agcaaatgca cttgaatcca agagaaacgc aaagcttttt ctcttcacga tcagaatcct
38581 aaagtctaaa gtccatatta gaaaagctcg ataccgaggc ttgaacgtca atcaaatcag
38641 aataattatc agagttcagt ttgagaccta attgtaaaag gtcggtgttc ttctcaaata
38701 aaaagattgt aatcatttag tgaaataaaa attatatttt tttcacttat aaatattgca
38761 agtatttaat tatatataat atatataata tatataataa tatataatat aatatatata
38821 tataatatat ataataataa tataaaaata ataatataat aataataata ctataataat
38881 aacaatataa taataataat atagtaataa taatataata ataataatat actntatttt
38941 tttgntatac ttattttttta tcatgggtgg atgccagaat attaaattgc tgttgntgnt
39001 gntgatgata atgtcgctgt ggtggttttg gtactattgg nttcttctga ttcggagttg
39061 tcgctagctc acttttgtct cccgacttcg agcgtgttta aatttttaata ttttttcctgn
39121 gtacttttca ggttcntggc ggctctcccc ttcttcttct gntctttctc tggcttctct
39181 tcggtggggt caagcttcag cttctctaca cacagcctac tganctagaa taacannact
```

Figure 14 (continued)

```
39241 ctccgcagat ggaatttaaa gcaatacaag nggtaaatgg ggattaatat cctagaggna
39301 tgctatgaat aaccaaaaaa tcaccncact acaattttgt caaatcgata gttccgcaag
39361 tttccaagcc cagactaaca agttaaaaga agtgctttgg aattatcaat cacaaagaat
39421 ctaaacatcc taggagcaca tccaagaggg ggcgaanntt cacttgaagt tccgagacaa
39481 ctggaagttc cataaagctc aatttacaac ggccttcaaa agctcattag actaaagtnc
39541 caaagttgat attcaaaagc tagagaacga tacttgaacg tcaatcaatc tgatcaataa
39601 gttaagttca gtttgagacc taaataatgg ttttaaaaaa aagtgatatt tttatgaaag
39661 attgcaaatt gcatatatat atatatatat atatatatat ttagatgcaa actcantgca
39721 tttgggaatg caataaaaat aactaagtta atttttaaat ttgtcaatac gaaacacttt
39781 taccagtata tatatatata tatattttac tattaacaaa ttaagcaaac acgatatttt
39841 ctacagtgga ttgcaaatgc atgaaggaag gaacttaacg gttaaacggg aaacaaccga
39901 aattttgccg cgcgtgccaa aagagtgtcc atattttaa gatactaatt taaaaaaaat
39961 tacatggaga tatatatatc aaacgtggac gattcggcgt gatccataac gactttaaa
40021 aaattcttaa ataattggaa atcaatatat atatattctg acgtatttgg tccaaccacc
40081 ggcacttaaa attatttcag gagaccctat aaaaaacagt ataataaagt aatcggagct
40141 gcggcagctc cgtttaaaac tcgtttgaat gtgcagcgcg gcctcagccg ttgttaaaca
40201 tttatccctc ggggactttg ttanctctgt ttcanaagtt cctattcaat ttcggnaatt
40261 cttttaccng ttggnattgt tagatccngn aatcttttc tttgaaatcc tctggtaatt
40321 catttgggtc attattaaga tagtattaga ctatcaaaat tgtaggtccc gatatgtcca
40381 aataanaggg gtttattgtt tattttgtgg taatattggc gtgcttcggg taaacattct
40441 accaatatat gtataggcag gcgtgctnat ttattgtgtc tttatgtaca aacnngtctg
40501 tgtgaaacat ttgtatgacc ttatcgtttt ggtaagatct tttattaata tctgccagtc
40561 caattatatt gcttaataag acataaatca gaggtgcagg gcgggactac taatattcct
40621 cttgtcgata gtgggtattc ttcctttacc agtatatttc gttttttat ttttttttt
40681 ttatttttat attttattca tgatttacaa tttaaacctc ttaatcattc atatcatatt
40741 ttactttttt taggaaaatt ttaattttta caatttctac catagtttat ggtgccttta
40801 tttttccttt taatttccaa acgtagaatg agaccaggat gttttaactt caatctggct
40861 tactgttttt tgcctaaatc gatgagaagc gcttccggct tagcttgcag cgaatcggct
40921 tatacatatg tatagtgaca tatccataag tccctaagac ttaagcatat gcctacatac
40981 taatacactt acaacatata caccccaata caacatacac tactccggat gnacccaaca
41041 gataccagat aagaaaaaga ctgttatacg atcctcgaga atagaaanaa cccccaattct
41101 agataagtca cccactggta gactaaacat ccgtcccta atttaaacaa ttccttgctt
41161 aagcctcacc ccatcgtcac attcccacgt tcaaagctcg gagccgcaat cccgaaaaac
41221 aaagtatcg atttcaataa acaattata agaatctaag agcacttgta tccaagagca
41281 aatgcacttg aatccaagag aaacgcaaag cttttctct ttacgatcag aatcctaaag
41341 tctaaagtcc atattagaaa agctcgatac cgaggcttga acgtcaacca aatcagaata
41401 attatcagag ttcagtttga gacctaattg taaaaggttc ggtgttcttc tcaaataaaa
41461 agattgtaat catttagtga aataaaaatt atatttttt cacttataaa tattgcaagt
41521 atttaattgg cgcagtcggt taggatccaa taaaataaaa gagtcctttt agtacggtac
41581 tgatcaactg aaggatatgc tatacgacta gctatccaag atcagcgaat taaaatagtg
41641 attcaaaaat atttttaat ccgcaaaaga atctacgtga aagtagtatt caaaataaaa
41701 tcccgtgcgg tcggaaacaa aaattaattt aaattttta attccgaaac ttaaaaccaa
41761 gtttaaagaa aacttaaaat caagaaaact taaaccaag tttaaagaaa acttaaaatc
41821 aagaaaactt aaaaccaagt ttaaagaaaa cttaaaatca agaaaactta aaaccaagtt
41881 taaagaaaac tcaaaatcaa gaaaacttaa agccaaaata agctagaaaa ctaaaagaca
41941 tcatggcagt cccacaactc tcagaaacac acctaaacca actgctaaac caaatcaaag
42001 aattaaacta ctacgatggc gcacctggca aattatctgg attcgtcaac caagtggaac
42061 aactgctcag tttataccca acacaggaag caagacaggc acacgtcata tatggagcag
42121 tgaagcggtt attagtggat tcagccttag aagtcgtaac ccaggaaaga gctaacacat
42181 ggctggacat gaagaaagca ctggcaatgg cattcaaaga ccatagacct tatgtaactc
42241 tcatcagaca attagaagac atatcatacc caggaagtat ctgtaagttt atagaaaaat
42301 tagaaacaca atactggatt atgttcgata agttagaatt agaaagtgac catgttgata
42361 aatcgaatta taccgaaatg ttaaacaaaa ctgttaaatc agtaatagat cgaaaactgc
42421 cggatagaat ttatatgtct ttggcacgta agatattga taacatttat aaattaaaac
42481 aagcatcaat ggaattaggc ctttatgatg ctattccaga aaatcaccgt tctaatagaa
42541 cagaaatgaa taaacgtagg aacaggggaa actataatca aaataataat caaaaatatt
42601 acaataatag aaatcacaac tacagtaatt attatcctag catgaatcag aatcataata
42661 cacaaccacc tcagaatccg actcaaccta tgacaaatca aaaccaatat tcaccgcgtt
42721 tcataccgaa taatcaaaga gggaattatt atgcatttag acgagactta acacaagctc
42781 agcagaacaa cccacttaat aacacccta acttccaacc ttcgacatcg aataatatta
```

Figure 14 (continued)

```
42841 acagacaagg gccagtaaaa agacaacgcg agagtcagag tgaccaaagc aggatggatg
42901 taaattttca tcaagctgcc tcggacactc aaatgataga gaaggacata caagtcccta
42961 tgtaaaaata attcatcata ataaaaatta taagggaatg atcgatacag gatcatcaat
43021 taacatcata agagaaaatt ttgagaactt agaagaaaag gaagaaaacc taatagtata
43081 cactattaaa ggaccaataa cactaaagag aagtataata ataaaaccta cttcagtatg
43141 tccgtctgct caaaaattct acattcacaa attttctgat aactatgatt tcttgttagg
43201 tcgaaagtat ttagaagata caaaagctaa aatagattat gctaacgaaa cagtaacact
43261 aggctcaaaa gtatttaagt ttctctatga agaaagaag ggcgagaccg catccaaatg
43321 ccttgaccca caagaaaaga atgattccgc tctagtggac agaaccaaac caaaaatgca
43381 aaaggttaag accgcaccta agtgccttaa accaaagcat caacagcaga agaaagagac
43441 cgcattaccc aaatgcctca tttcaaatgt tgttaaagac acagtggaca atgatgtaac
43501 acatctcgat cccatgtccg ttgacaacga tatagtcaac ttcgcgatta acaatgagtt
43561 acgcgaatgt aacgagtata gactcgaaca cttaaatgca gaggaagttg aatgtttaaa
43621 gaagttccta tacgaatata gagacattca gtacaaagag ggcgaaaatt tgaccttcac
43681 cagtactatt aaacatgtca tccagactca acacgaagac ccagtatacc gtaaaccctta
43741 caagtaccct caaagcgttg accaagaagt taacaaacaa attaaagaaa tgatagaaca
43801 agggattgtt cgcaaatcga agtcccctta ttgttctcct atttgggtgg tccccaagaa
43861 ggcagacgcc tctgggaaac aaaaattcag gttggtagtc gattacagga acctaaatga
43921 gataactgtt aacgacaaat ttcccattcc ccgaatggat gagatattgg acaaactagg
43981 tagatgccaa tactttacca ctatagatct agccaagggt tttcaccaaa tccaaatgga
44041 tgaaaattct attgcaaaaa cagctttttc aactaagcat ggcattatg aatatactcg
44101 tatgcccttt ggtttaaaaa acgctccagc tactttcag agatgcatga ataatcttct
44161 ggaagattta atctacaaag actgtttagt ctatttagac gatattattg tttattccac
44221 tccattggaa gaacacattt tatccctaaa gaaagtcttt gaaaaactga gagacgctaa
44281 tttaagtttg caactagata aatgtgaatt catgaagaaa gaaactgnca aaaactgtca
44341 caaacccgac agttgaccct tatttgccgc atggtttgac ctgaaagttt gattttcaag
44401 tttaaggcaa taatgtaaag ctgaggggag atcagctggc tctttattg ccaaaaggcg
44461 aggtaaatct cctcgaaggc ctctaataaa agtatccaga gcttttcaa cattttccta
44521 acgaagtgct cggattctcc gctcatttgc atgcagccga ccttatttag aattagagaa
44581 agatttttgt agacgtcctg gtggaagtct tccaccgact gctggtggcc ttcaaccaaa
44641 gttgacattt ggtattccaa ggtagctatg tcccgtttat cgacatggcc ttccagtcca
44701 gcggaatgct gtaggactcg atgccacatc agcacttcca acaattttat ttcttatggt
44761 atgacgcata ccataatatc ttggagtacc cacaaatggg gtataagtct ccatgattct
44821 atcancgctc cttttccaag acccaaattc tgctanattt ccagagaatt ccctgataga
44881 ttttacgata tcgggcaccc tgtcaaagtc cactaaatta tttctgtatt cggntcgatn
44941 acctgatcgc tcacgtcagt aaagtcaaga gtatcgttat tcatttgttt tatcagtcca
45001 ggtaaaactt ggaccaccgt ttggccaatt aatgctgtct actgttcgac actcatgtct
45061 acgcgatgct gttcaggcag gtcgggtctt tctgagggta ccggtctctc atttgaacta
45121 aaagctgagg gtcttattat attattaggg tttgccatgt gggctttaaa ttcggacaac
45181 acctgcataa aacaagccta aacctaaaca aatttgaact taacaaaagt tgtgggcaga
45241 aaatatggaa tgcatttgct tacttttctt tcgttntttt ttttaaatt ttgcgttgca
45301 ataataattt aagcttgccg cggcaatttt gctttcagag cattggtacg agaaaagaat
45361 tgnttctttt agaaganctc ttangaactg ggttggaaaa tataataaaa ataatattac
45421 caataataat aatataataa taatnatata aaaataataa tataataatn ataatataat
45481 aataaccatt ttannattat taatttnnna attatnattt attatattat aannttaata
45541 atttggnaac ctaaggntaa tatgggggg tggatgccag aatattaaat tgctgttggt
45601 ggtgnnnntg atgataatgt cgctgtggtg gttttggtac tattggttct tctgattcgg
45661 agttgtcgct agctcacttt tgtctcccga cttcgagcgt gtttaaattt taatattttt
45721 cctggtactt ttcaggttcg tggcggctct ccctcntct tcttctgtct ttctctggct
45781 tctcttcggt ggggtcaagc ttcagcttct ctacacacag cctactgatc tagaataaca
45841 ctactctccg ctgatggaat ttaaagcaat acaaggggta aatggggatt taatatccta
45901 gaggatgcta tgaataacca aaaaatcacc cactacaatt ttgtcaaatc gatagttccg
45961 caagtttcca agcccagact aacaagttaa agaagtgct ttggaattat caatcacaaa
46021 gaatctaaac atcctaggag cacatccaag agggggcgaa attcacttga agttccgaga
46081 caactggaag ttccataaag ctcaatttac aacggccttc aaaagctcat tagactaaag
46141 tnccaaagtt gatattcaaa agctagagaa cgatacttga acgtcaatca atctgatcaa
46201 taagttaagt tcagttgag acctaaataa tggttttnaa aaaagtgata ttttatgaa
46261 agattgcaaa ttgctttta taaaaaatat atatatttag atgcaaactc antgcatttg
46321 ggaatgcaat aaaaataact aagttaattt ttaaatttgt caatacgaaa cacttttacc
46381 agtatatata tatttttta ctgattaaca aattaagcaa acacgatatt ttctacagtg
```

Figure 14 (continued)

```
46441 gattgcaaat gcatgaagga aggaacttaa cggttaaacg ggaaacaacc gaaattttgc
46501 cgcgcgtgcc aaaagagtgt ccatattttt aagatactaa tttaaaaaaa attacatgga
46561 gatatatata tcaaacgtgg acgattcggc gtgatccata acgactttta aaaaattctt
46621 aaataattgg aaatcaaatt atatatattc tgacgtattn ctggtccaac caccggcact
46681 taaaattatt tcaggagacc ctataaaagt ataataaagt aatcggagct gcggcagctc
46741 cgtttaaaac tcgtttgaat gtgcagcgcg gatcctcagc cgttgttaaa catttatccc
46801 tcggggactt tgttanctct gtttcanaag ttcctattca atttcggaat tcttttaccn
46861 gttggnattg ttagatccng naatcttttt ctttgaaatc ctctggtaat tcatttgggt
46921 cattattaag atagtattag actatcaaaa ttgtaggtcc cgatatgtcc aaataanagg
46981 ggtttattgt ttattttgtg gtaatattgg cgtgcttcgg gtaaacattc taccaatata
47041 tgtataggca ggcgtgctna tttattgtgt ctttatgtac aaacnngtct gtgtgaaaca
47101 tttgtatgac cttatcgttt tggtaagatc tggtatcttt tctntgaanc ctccntgtaa
47161 ttcattttgg gttcatttac taagatagtt attggcctat caaaaattgt aggtnccgat
47221 atgtccaaat tatnnggttn antgtttatt ttgtgtagaa ttggcgtgct tcggtaaanc
47281 attctccaat atatgtatag gcaggcgtgc ttattatntg tctgtatgta catacctgtc
47341 tgtgtgaaac atttgtatga cttatcgttt tggtaagatc ttttattaat atctgcccag
47401 tccaattata ttgcttaata agacataaat cagaggtgca ggcggactac taatattcct
47461 cttgtcgata gtgggtattc ttctttacca gtatatttcg gttttttttgt tttttttttt
47521 ttatttttat attttattca tgatttacaa tttaaacctc ttaatcattc atatcatatt
47581 ttactttttt taggaaaatt ttaattttta caatttctac catagtttat ggtgcctttta
47641 tttttccttt taatttccaa acgtagaatg agaccaggat gttttaactt caatctggct
47701 tactgttttt tgcctaaatc gatgagaagc gcttccggct tagcttgcag cgaatcggct
47761 tatacatatg tatagtgaca tatccataag tccctaagac ttaagcatat gcctacatac
47821 taatacactt acaacatata caccccccn accacataca ctactccgga tgtacnnaac
47881 anataccaga taagaaaaag actgttatac gatcctcgag aatagaaana accccaattc
47941 tagatctaga taagtcaccc actggtagac taaacctccg tcccctaatt taaacaattc
48001 cttgcttaac cctcaccccca tcgtcacgtt cccacgctca atgctcggac ccgaaatccc
48061 gaaaaacaaa agtatcgatt tcaataaaca aattataaga atctaagagc acttgtatcc
48121 aagagcaaat gcacttgaat ccaagagcaa atgcacttga atccaagaga aacgcaaagc
48181 ttttctctct cacgatcaga atcctaaagt ctaaagtcca tattggaaaa gctcgatacc
48241 gaggcttaaa cgtcaatcaa atcagaataa ttatcagagt tcagtttgag acctaattgt
48301 aaaaggtcgg tgttcttctc aaataaaaag ttttgtaatc atttagtgaa ataaaaatta
48361 tatttttca cttataaata ttgcaagaat ttaattggcg cagtcggtag gatccaataa
48421 aataaaagag tccttttagt acggtactga tcaactaaat gatatgctat acgtctagct
48481 atccaagatc agcgaattaa aatagtgatt cgaaaatatt ttagagatcc gtaaaagaat
48541 ctacgtgaaa gtagtattca agtaaaatc ccgtgcggtc ggaaacaata atttaaattt
48601 tttaattccg aaacttaaaa ccaagtttaa agaaaactta aaccaagtt taagaaaac
48661 ttaaaccaa gtttaaagaa aacttaaaac cagtttaagg aaacttaaaa ccagtttaaa
48721 gaaaataagt ttaaagaaaa cttaaaatca agaaaactta aaccaagtt taagaaaac
48781 tcaaaatcaa gaaaacttaa agccaaaata agctagaaaa ctaaaagaca tcatggcagt
48841 cccacaactc tcagaaacac acctaaacca actgctaaac caaatcaaag aattaaacta
48901 ctacgatggc gcacctggaa ttatctggat tcgtcaacca agtggaacaa ctgnctcagt
48961 ttatacccaa cacaggaagc aagacaggca cacgtcatat atggagcagt gaagcggtta
49021 ttagtggatt cagccttaga agtcgtaacc caggaaagag ctaacacatg gctggacatg
49081 aagaaagaac acggcaatgg tattcaagaa ccatagacct tatgtaactc tcatcagaca
49141 attagaagac atatcatacc caggaagtat ctgtaagttt atagaaatag aaacacaata
49201 ctggattatg ttcgataagt tagaattaga aagtgaccat gttgataaat cgaattatac
49261 cgaaatgtta aacaaaactg ttaaatcagt aatagatcga aaactgccgg atagaattta
49321 tatgtttttg gcaacgtaaa gatattgata caatttattt aaaacaagca tcaatgnaat
49381 taggccttta tgatgctatt ccagaaaatc accgttctaa tagaacagaa atgaataaac
49441 gtaggaacag gggaaactat aatcaaaata ataatcaaaa atattacaat aaatagaaat
49501 cacaactaca gtaattatta tcctagcatg aatcagaatc ataatacaca accacctcag
49561 aatccgactc aacctatgac aaatcaaaac caatattcac cgcgtttcat accgaataat
49621 caaagaggga attattatgc atttagacga gacttaacac aagctcagca gaacaaccca
49681 cttaataaca cccttaactt ccaaccttcg acatcgaata atattaacag acaagggcca
49741 gtaaaaagac aacgcgagag tcagagtgac caaagcagga tggatgtaaa ttttcatcaa
49801 gctgcctcgg acactcaaat gatagagaag gacatacaag tccctatgta aaaataattc
49861 atcataataa aaattataag ggaatgatcg atacaggatc atcnnttaac atcataagag
49921 aaatttgga gaacttagaa gaaaaggaag aaaacctaat agtatacact attaaaggac
49981 caataacact aaagagaagt ataataataa aacctacttc agtatgtccg tctgctcaaa
```

Figure 14 (continued)

```
50041 aattctacat tcacaaattt tcngananna tnatttcngg tagntngaaa gttntnnaga
50101 nccaaangcc ttattgnttt angcaacggg ccagtagnta ggctcaaaat tntttagttt
50161 ctntatanaa aannaaggnn gagaccgcat ccaaacgcnt tgnccnaacc aagagaatga
50221 tncgntttag tggacanaat caaancanan atgcaaaagg ttaagacccc acctaagtgc
50281 cttaanccaa agcatnaaca tcaagagang gagactgcat tacccaaatg cgntcatttc
50341 gaatgttgtt aaagacacag tggacaatga tgtaacacat ctcgatccca tgtccgttga
50401 cnacgatata gccnacttcg cgattaataa tgagttacgc gaatgtaacg agtatagact
50461 ngaacacttn aatgcanagg aagttgaatg tttaaagaag gtcctatncg aatanagana
50521 cattcagtac aaagagggcg aanatttnnc nttcaccagt nctattaanc atgtcatccg
50581 aantcaacan gaagacccag tataccgtaa accctncang taccctcaga gcgttgacca
50641 anaagtcacc nancaaattn aananatgat aggcnaggga ttgttcnaaa atcgnagtcc
50701 ccttattgtt catcctatgt gggtggtccc caagaaggca gncgcctctg gganaaaaaa
50761 tgcaggttgg tagtcgatta cagnaatcta natganataa ctgttagcga ccaatttccc
50821 attccccgaa tgntntccct angtnagtcg tnntaanggc cgccagagnt tntcatntna
50881 nttcccgtnc cgttagcaa
```

NUCLEIC ACID ENCODING A POLY-(ADP) RIBOSE POLYMERASE ENZYME AND USES THEREOF

CROSS-REFERENCE TO RELATED APPLICATIONS

This application claims benefit under 35 U.S.C. § 119(e) to U.S. Provisional Application No. 60/399,460, filed Jul. 31, 2002, incorporated herein in its entirety.

STATEMENT REGARDING FEDERALLY SPONSORED RESEARCH OR DEVELOPMENT

This invention was made with U.S. government support under grant number GM-27875 awarded by the National Institutes of Health. The U.S. government has certain rights in the invention.

BACKGROUND OF THE INVENTION

1. Field of the Invention

The present invention relates to the identification and cloning of a poly(ADP-ribose) polymerase (PARP) enzyme lacking catalytic activity and methods of modulating chromatin structure.

2. Related Art

Cells within multicellular eucaryotes as they develop build complex tissue-specific chromatin architectures to express certain genes and silence others (reviewed in Farkas et al. 2000. Gene 253:117-36). These intricately acquired chromatin domains must be preserved when chromosomal DNA is accessed for replication and repair, and when reprogramming is required it must be precisely targeted. In diverse eukaryotes, protein ADP-ribosylation plays important but imperfectly understood roles in apoptosis, gene transcription and in preserving chromatin during DNA repair (De Murcia, G., and Shall, S. 2000. From DNA damage and stress signalling to cell death. Poly (ADP-Ribosylation) Reactions. (New York: Oxford University Press; Ziegler et al. 2001. Bioessays. 23: 543-548).

Poly(ADP-ribose) polymerase-1 (PARP1) is the major nuclear source of this activity in mice. The zinc fingers of the PARP1 protein specifically recognize DNA nicks and breaks and PARP activity is strongly increased upon binding to such sites. The bound, activated protein transfers multiple ADP-ribose moieties from NAD onto local chromatin proteins such as histones, topoisomerases, polymerases and transcription factors (Poirier et al. 1982. Proc. Natl. Acad. Sci. USA. 79: 3423-3427; Menissier-de Murcia et al. 1997. Proc. Natl. Acad. Sci. USA. 94: 7303-7307). These modifications facilitate base excision repair by transiently dissociating target proteins from the chromosome to expose the lesioned area, by down regulating transcription of the affected genes, and by modulating the activity of checkpoint and stress regulatory proteins. The newly repaired region returns to a normal state after PARP downregulates its own activity by automodifying a specific domain and the chromatin proteins, freed of ADP-ribose groups by a specific glycosylase, reassemble. In contrast, if damage it too extensive, PARP is specifically inactivated by caspase cleavage as the cell commits to apoptosis (Kim et al. 2000).

A great deal of biochemical and cellular evidence supports the idea that PARP removes chromatin within damaged regions to facilitate DNA repair (de Murica, 1999). Moreover, mice mutant for Parp1, one of at least five murine genes encoding PARP-related proteins, though viable and fertile, are severely compromised in their ability to repair DNA lesions (Dantzer et al. 1998. Nucleic Acids Res. 26: 1891-1898). Mice with defective PARP1 genes develop into fertile adults, hence a developmental role for PARP1 has yet to be established (Wang et al. 1995). However, four other mouse genes encode distinct ADP-ribosyl transferases with related catalytic domains (Amé et al. 1999. J. Biol. Chem. 274: 17860-17868; Kickhoefer et al. 1999. J. Cell Biol. 146: 917-928), including a telomere-associated form known as Tankyrase (Smith et al. 2001. Science. 282: 1484-1487), so functional redundancy may have obscured such a role.

Data suggesting that PARP-mediated chromatin stripping is used in other contexts has been lacking. For example, Parp1 knockout mice in addition to their damage susceptibility display dramatic immune defects, characterized by an inability to induce genes controlled by NF-κB transcription factors (Kameoka et al. 2000. Biochem J: 346:641-649). However, this defective immune response may be explained by the disruption of specific complexes that PARP forms with transcription factors such as YY1 (Oei et al. 1997. Biochem. Biophys. Res. Commun. 240:108-111), p53 (Mendoza-Alvarez et al. 2001), PAX6 (Plaza et al. 1999. Oncogene. 18:1041-1051), and NF-κB itself (Hassa et al. 1999. Biol. Chem. 380, 953-959) rather than by action at the chromatin level. Consequently, roles for PARP beyond its duties as a stress response regulator and transcriptional cofactor remain to be established.

The model eukaryote, Drosophila melanogaster, has the potential to support detailed genetic studies of PARP function in both physiology and development. Its genome contains a single gene, Parp, related to mammalian Parp1 (Uchida et al. 1993. Proc. Natl. Acad. Sci. USA. 90: 3481-3485; Hanai et al. 1998. J. Biol. Chem. 273: 11881-11886), and one homologue of tankyrase (Adams et al. 2000. Science 287: 2185-2195). The protein specified by the major Parp transcript, PARP-I, includes all the conserved domains characteristic of mammalian PARP1 except a canonical caspase cleavage site. Parp-I transcripts are expressed in nearly mature ovarian follicles and throughout embryonic development, but were not detected in larvae (Hanai et al. 1998). Parp-II transcripts lacking the automodification domain are produced via differential splicing of a single exon (Kawamura et al. 1998. Biochem Biophys Res. Commun. 251: 35-40). However, genetic studies have been hindered because Parp is located deep within centromeric heterochromatin, and its exons are scattered among several contigs that remain unlinked to the euchromatic genome sequence (Adams et al. 2000).

Drosophila development has been extensively studied to determine how changes in chromatin structure contribute to specifying programs of tissue-specific and temporally regulated gene expression (reviewed in Farkas et al. 2000; Gerasimova et al. 2001. Annu. Rev. Genet. 35: 193-208). Zygotic transcription begins during the first 14 embryonic nuclear cycles concomitant with the establishment of heterochromatin and of nucleolus formation (Foe et al. B. 1983. J. Cell Sci. 61: 51-70). During subsequent embryonic and larval stages, chromatin domains are refined under the control of multiprotein remodeling complexes (reviewed by Cairns, B. R. 1998. Trends Biochem. Sci. 23: 20-25; Jacobs et al. 1999. Semin. Cell Dev. Biol. 10: 227-235). The role of NAD-requiring enzymes in these processes is poorly known, but in addition, Parp Drosophila contain a gene structurally and functionally related to the NAD-dependent histone deacetylase encoded by the yeast Sir2 locus (Barlow et al. 2001. Exp. Cell. Res. 265: 90-103; Rosenberg et al. 2002. Cell. 109: 447-458).

However, recent genetic studies in Drosophila melanogaster show that PARP plays a much more general role by organizing chromatin at multiple points throughout the life cycle (Tulin et al. 2002). Flies bearing mutations in the single *Drosophila* PARP gene display extensive changes in both the repression and activation of chromosome domains, and die during the transition between the $2^{nd}$ and $3^{rd}$ larval instar. Heterochromatin remains abnormally accessible to nuclease, and the transcription of certain repeated sequences such as the copia retrotransposon fails to be repressed. Nucleoli are defective, and at least some specific genes seem also to misfunction as Parp mutant larvae frequently arrest development during metamorphosis. Tulin et al. (2002) proposed that the genetic requirement for PARP resulted from its involvement in locally stripping and re-assembling chromatin under developmental control. However, it is difficult to rule out that these effects were secondary to disruption of transcriptional co-activation.

*Drosophila* chromatin normally undergoes many highly programmed changes during embryogenesis that could be targets of PARP action (reviewed in Farkas et al. 2000). These events continue during larval development through the action of chromatin remodeling complexes (reviewed in Simon et al. 2002. *Curr Opin Genet Dev.* 12: 210) and histone modifications (reviewed in Wolffe and Guschin, 2000). The larval polytene chromosomes reveal that dramatic programmed chromatin alterations continue within specific euchromatic regions that form puffs at the site of newly activated genes (reviewed by Ashburner and Berendes, 1978). Many developmental puffs are induced by the moulting hormone ecdysone and contain steroid hormone response genes or their targets (reviewed by Thummel. 2000. *Insect Biochem. Mol. Biol.* 32:113-120).

Others puffs are rapidly induced at the sites of stress response genes following heat shock (reviewed by Farkas et al. 2000). Despite their association with induced transcription, puffs are neither necessary nor sufficient for high level gene transcription (Meyerowitz et al. 1985), and their biological significance has remained unclear.

Thus, the effects of proteins on chromatin structure are varied and influence gene transcription and expression. There is a clear need, therefore, for identification and characterization of proteins which moduldate chromatin structure, both normally and in disease states. In particular, there is a need to specifically, and in a controlled manner, manipulate chromatin structure and re-programming so as to effect expression of a gene or genes of interest in order to treat or prevent disease and/or to manipulate biological processes in vivo and in vitro.

SUMMARY OF THE INVENTION

The invention is directed, in one aspect, to a method of modulating chromatin structure, the method comprising altering expression of PARP-e.

The invention is also directed, in another aspect, to an isolated nucleic acid molecule comprising a polynucleotide having a nucleotide sequence at least 95% identical to a sequence selected from the group consisting of the nucleotide sequence of the DNA contained in Genbank Accession No. AF533701 or Genbank Accession No. AF533702. In another embodiment, the invention is directed to an isolated nucleic acid molecule comprising the nucleotide sequence of Genbank Accession No. AF533701 (SEQ ID NO: 1) or Genbank Accession No. AF533702 (SEQ ID NO: 10).

In another aspect, the invention is direct to an isolated PARP-e protein which comprises an amino acid sequence at least 95% identical to the amino acid sequence of SEQ ID NO: 2. In a different aspect, the invention is directed to an isolated protein comprising an amino acid sequence at least 90% identical to amino acids 1 to 613 of SEQ ID NO. 2 wherein said protein has the activity of modulating chromatin structure.

In a yet a different aspect, the invention is directed to an isolated polynucleotide molecule selected from the group consisting of a) a polynucleotide molecule having at least 95% sequence identity to SEQ ID NO: 1; b) a polynucleotide molecule which is a fragment of a); and, c) a polynucleotide molecule which is the complementary nucleotide sequence of (a) or b).

In yet a different embodiment, the invention is directed to an isolated PARP-e protein having an amino acid sequence selected from the group consisting of: a) the amino acid sequence as set forth in SEQ ID NO. 2; and, b) the amino acid sequence encoded by a polynucleotide which hybridizes under stringent conditions to a polynucleotide having a nucleotide sequence as set forth in SEQ ID NO. 1; c) the amino acid sequence encoded by a polynucleotide having a nucleotide sequence at least 95% identical to a sequence selected from the group consisting of the nucleotide sequence of the DNA contained in Genbank Accession No. AF533701 (SEQ ID NO: 1) or Genbank Accession No. AF533702 (SEQ ID NO: 10); and, d) the amino acid sequence encoded by an isolated nucleic acid molecule comprising the nucleotide sequence of Genbank Accession No. AF533701 (SEQ ID NO: 1) or Genbank Accession No. AF533702 (SEQ ID NO: 10).

The invention is also directed to a method of inhibiting the growth of an insect, comprising: a) creating an insertion mutation in the insect PARP-e gene of a first early insect embryo; b) culturing said first embryo to produce an insect of a first mutant strain; c) creating an insertion mutation in the insect PARP-e gene of a second early insect embryo; d) culturing said second embryo to produce an insect of a second mutant strain; e) mating an insect of said first mutant strain with an insect of said second mutant strain; wherein larvae that contain both said first and second mutations show inhibited growth as compared to an insect not comprising both said first and second mutations. In a different aspect, the invention is also directed to a method of inhibiting the growth of an insect, comprising: a) contacting embryonic insect cells with a composition comprising an effective amount of a dsRNA molecule specific for PARP-e, wherein contact with said dsRNA molecule inhibits growth of said insect.

Figure 1:
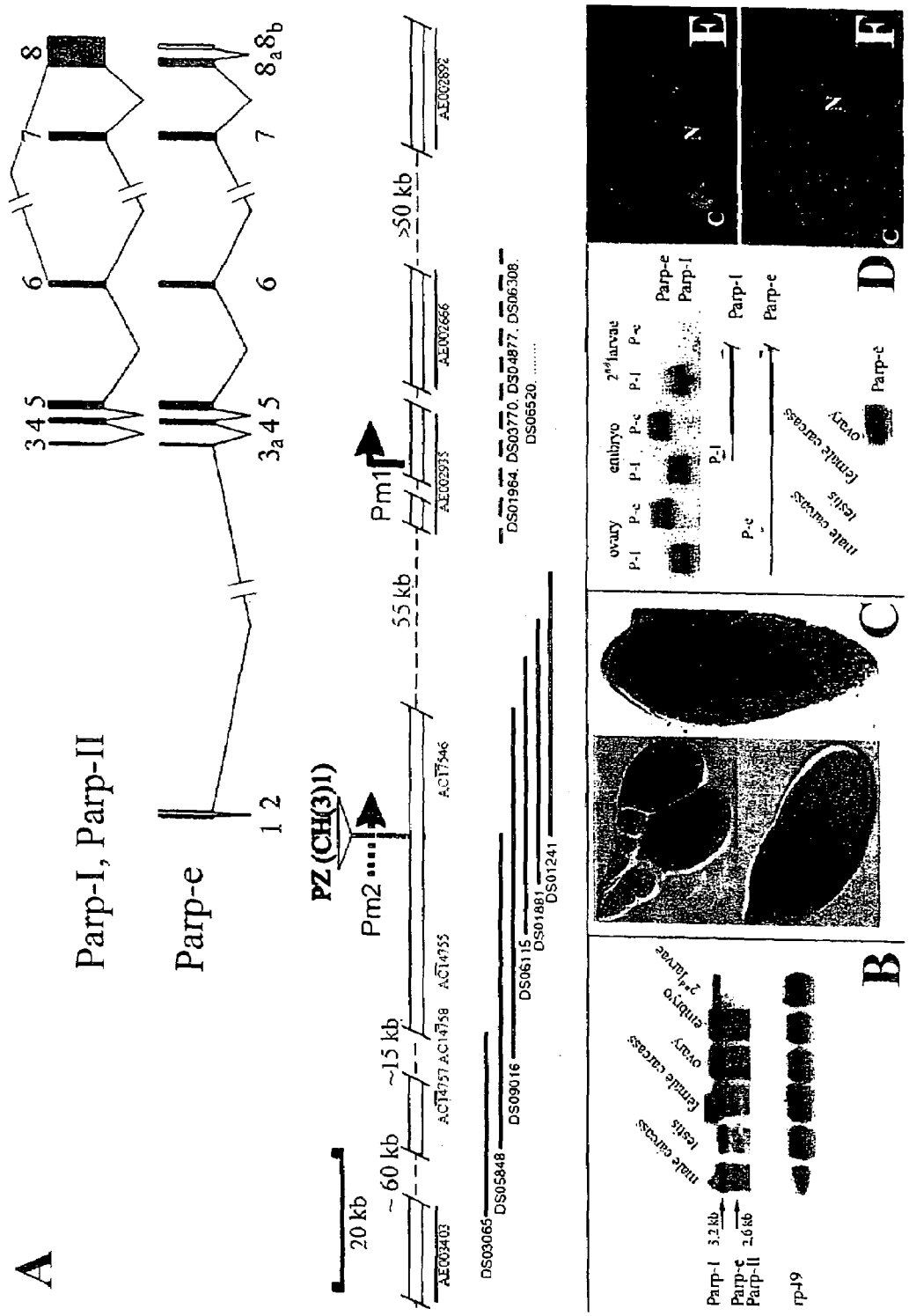
FIGS. 1A-F. Structure and expression of the *Drosophila* Parp locus. (A) Deduced genomic structure of the 300 kb Parp region; open boxes are sequenced. The arrangement of the exons encoding Parp-I is shown above (Uchida et al. 1993; Hanai et al. 1998). Below, the position of three unlinked *Drosophila* genomic contigs (thin black lines: AE002935, AE002666 and AE002892) homologous to Parp-I exons are shown at right (Adams et al. 2000). Pm1 indicates the Parp-I promoter deduced from 5' cDNA sequences (Hanai et al. 1998). A single cDNA isolated from early ovarian stages, GM10715, comprises the 5' and 3' regions of the alternatively spliced Parp-e transcript. The 5'-most 273 bp of GM10715 matches the genomic sequence flanking a P element insertion, CH(3)1 (Zhang et al. 1994. *Proc. Nat. Acad. Sci. USA.* 91: 3539-3543). A map of this region (left portion of figure) was constructed by chromosome walking using a P1 genomic library (Kimmerly et al. 1996. *Genome Research.* 6: 414-430) (below, thick black lines). The two resulting scaffolds were sequenced and found to span four small pre-existing genomic sequence contigs (thin black lines) and to link to a fifth (AE003403). The color code indicates which portion of PARP is encoded: DNA binding (red), automodification (purple), catalytic (blue), non-coding (green and yellow). (B) Multiple Parp transcripts. A Northern blot of poly(A)-containing RNA from the indicated developmental stages reveals both a 3.2 kb RNA, the size predicted for Parp-I, and a 2.6 kb RNA, the approximate size expected for Parp-II and Parp-e. Parp-homologous RNAs are abundant in both ovaries and embryos, and are reduced but still detectable in second instar larvae and adults. (C) Whole mount in situ hybridization using a 1.4 kb cDNA probe from the DNA-binding domain common to all isoforms labels Parp RNA in nurse cells and in oocytes from stage 9-14 follicles. (D) RT-PCR using isoform-specific primers (see diagrams) that distinguish between Parp-I (or Parp-II) and Parp-e demonstrate that Parp-e is produced in ovaries and embryos, but not at detectable levels in $2^{nd}$ instar larvae, or in adults outside the ovary. (E) Nuclei are shown from brains of third instar larvae expressing a Parp-I-DsRed fusion gene (see Examples). Protein is abundant in the chromocenter (C), the nucleolus (N) and at sites within euchromatin. (F) Third instar larval brain nuclei stained with anti-poly(ADP-ribose) antibody 10H show that protein-associated ADP-ribose is found in the same regions as PARP-DsRed.

FIGS. 7A-E. Parp$^{CH1}$ and Sir2$^{05327}$ have opposite dominant effects on the variegated expression of GAL4/UAS constructs. The variegated expression of an Arm-Gal4 driven UAS-Tim17B-DsRed construct (A-B) or a UAS-Sir2-DsRed construct (D-E) is modified by background genotype. In a Parp$^{CH1}$/+background (A and D), expression is strongly reduced compared to expression in a wild type background (B and E). Similar variegated expression of the same constructs driven by 69B-GAL4 is almost completely suppressed in a Sir2$^{05327}$/+background (C and F). Green=DNA.

FIGS. 8A-J. PARP is distributed widely in chromatin while ADP-ribose-modified proteins are enriched in polytene chromosome puffs. (A) In these diploid 13 larval brain cells, PARP-DsRed (red) is abundant in nucleoli (arrow) located near the chromocenter (arrowhead) but is also found throughout the nucleus. (DNA=green). (B) Nucleoli in 13 larval gastric cells labeled with Fibrillarin (red). Compare normal structure (arrow) in wild type (B) with variegated presence of nucleoli (arrow) in Parp$^{CH1}$ (C). (D) PARP-DsRed is abundant in nucleoli and is present a lower levels along the chromosomes of this 13 salivary gland cell. (E) The pattern of incorporated biotinylated-NAD 3 hours after injection of an 13 larvae shows heavy incorporation in the nucleolus (arrow), at certain euchromatic sites, and low labeling generally along the chromosomes (arrowhead). (F) Poly(ADP-ribosyl)ated proteins are enriched in the nucleolus (arrow) and at discrete sites within euchromatin (arrowhead) in this 13 salivary gland nucleus. (G) A nucleus similar to that shown in (F) was squashed, revealing abundant poly(ADP-ribosyl) modified proteins (yellow) within polytene chromosome puffs (arrow indicates the 2B puff; arrowhead indicates 74A, 75B puffs). (DNA=purple). (H,J) and I all show a short section of chromosome 3L containing the region of the major early Edison puffs 74A and 75B. Prior to the induction of puffing late in 13, the level of poly(ADP-ribosyl) modified proteins (red) are normal (H), but elevated levels are always observed after the puff has formed (I) (DNA=blue). The amount of PARP-EGFP (green) in this region is similar to that found all along the chromosome (J). (DNA=red).

FIGS. 9A-H. Parp is required for heat shock puffing and gene expression. The site of the major heat shock puffs containing hsp70 genes at 87A and 87C are shown from larvae that had not been heat shocked (A) and following 30 minutes at 37° C. (B). (C) Poly(ADP-ribosyl) modified proteins are present at general levels prior to heat treatment (0°), but increase greatly within ten minutes following 37° C. treatment of 13 larvae. Twenty minutes after the heat shock the amount of staining is decreasing (D). (E) When heat shocks were given 30 minutes after injecting larvae with the PARP inhibitor 3-aminobenzamide, no increase in poly(ADP-ribosyl) modified proteins occurs. (F) 87A, 87C heat shock puff pairs of various sizes (3 are shown) can be visualized in salivary gland chromosomes from 12 larvae using antibody to RNA polymerase. (G) A histogram comparing the size of the 87A, 87C puff pairs in 12 larvae from wild type (black) or in Parp$^{CH1}$ (red). (H) A Western blot comparing the amount of heat shock-induced Hsp70 protein produced in wild type (wt) or in Parp$^{CH1}$ larvae. Hsp70 production was reduced 5-10 fold when the blot was normalized using Actin.

FIGS. 10A-D. PARP is required to express innate immunity genes. (A) Cells from Parp$^{CH1}$ animals frequently become infected with bacteria as revealed by DAPI staining. (B) Variegated PAR$^{CH1}$ expression is shown by the presence or absence of AJ1-stainined nucleoli (red). (C) Infection with bacteria (arrow) is only found in cells that lack PARP activity as indicated by the absence of nucleoli. (D) A Western blot quantitating the response of wild type (wt) and in Parp$^{CH1}$ larvae to infection with injected *E. coli* bacteria. The levels of the NF-κB-dependent innate immunity genes Diptericine and Drosomycin were quantitated using the fusion genes and antibodies directed at the reported epitopes.

Figure 11:
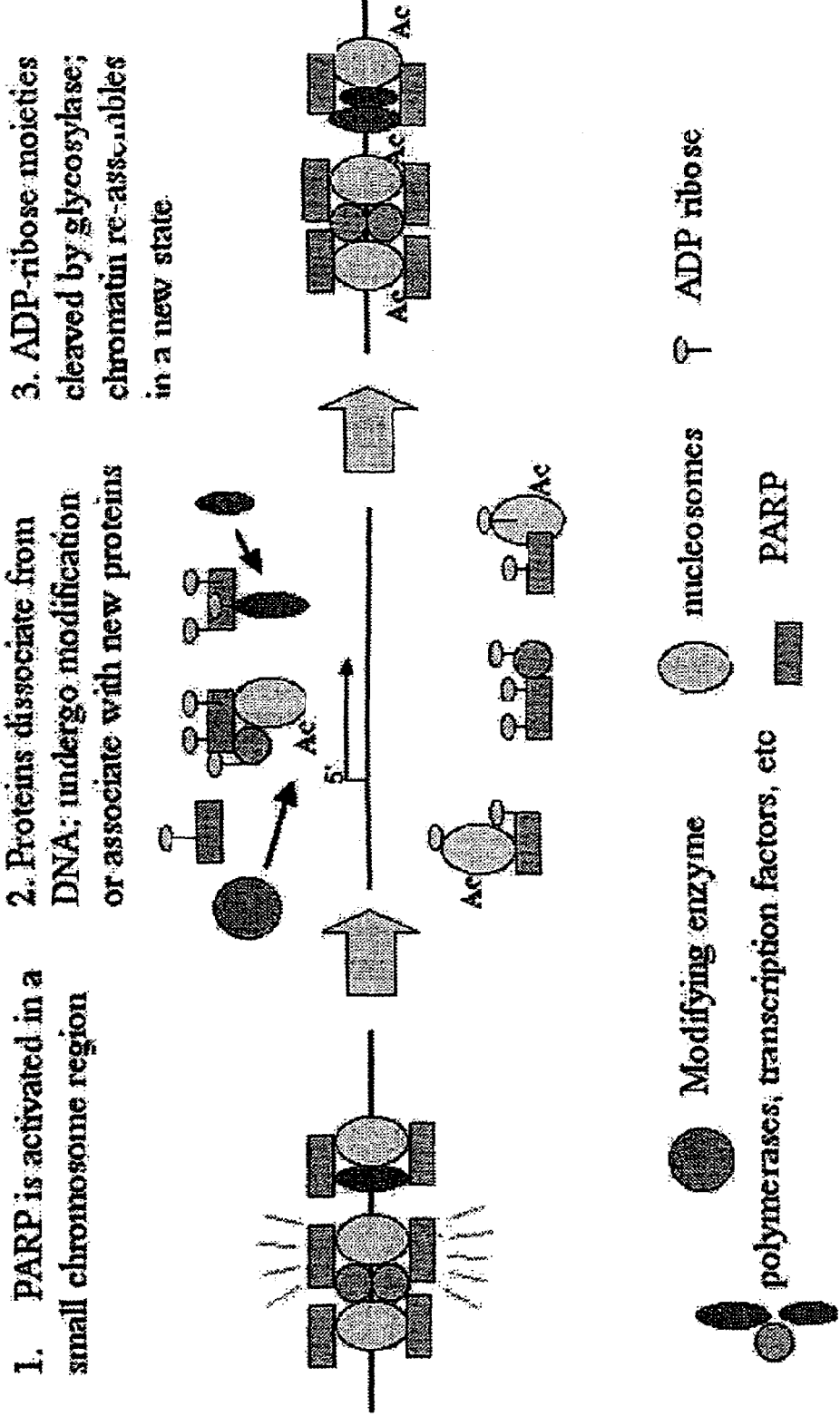

FIG. 11. Model of PARP-mediated chromatin re-modeling. A model of the proposed role of PARP in 1) receiving a local signal activating the enzymatic activity; 2) modifying nearby chromosomal proteins so that they dissociate from the DNA; 3) following cleavage, the original proteins, some of which may have become newly modified and formed new complexes with novel proteins, reassemble to form a specifically modified chromatin state.

FIG. 12. Nucleotide sequence of PARP-e cDNA (SEQ ID NO: 1).

FIG. 13. Amino acid sequence of PARP-e protein (SEQ ID NO: 2). The amino acid sequence was derived from the cDNA sequence.

FIG. 14. Nucleotide sequence of PARP DNA (SEQ ID NO: 10).

DETAILED DESCRIPTION OF THE PREFERRED EMBODIMENTS

Definitions

As is generally the case in biotechnology, the description of the present invention herein has required the use of a substantial number of terms of art. Although it is not practical to do so exhaustively, definitions for some of these terms are provided here for ease of reference. Unless defined otherwise, all technical and scientific terms used herein have the same meaning as commonly understood by one of ordinary skill in the art to which this invention belongs. Definitions for other terms also appear elsewhere herein. However, the definitions provided here and elsewhere herein should always be considered in determining the intended scope and meaning of the defined terms. Although any methods and materials similar or equivalent to those described herein can be used in the practice or testing of the present invention, the preferred methods and materials are described.

Euchromatin. As used herein, "euchromatin" refers to transcriptionally active genes and is loosely packed.

Heterochromatin. As used herein, "heterochromatin" is a form of condensed chromatin and is a complex of histones, DNA, and other proteins. Heterochromatin remains in a condensed form throughout the entire life cycle, and contains transcriptionally inactive DNA.

Isoform. As used herein, an "isoform" refers to a protein produced from a single gene by alternative mRNA splicing.

Positional effect variegation. As used herein, the term "positional effect variegation" refers to the effect obtained when genes that are transposed adjacent to heterochromatic regions undergo transcriptional silencing in only some cells in a population. The effect is inheritable in an epigenetic manner.

Stringent Hybridization Conditions. As used herein, the term "stringent hybridization conditions" means overnight incubation at 42° C. in a solution comprising: 50% formamide, 5×SSC (1×SSC=150 mM NaCl, 15 mM trisodium citrate), 50 mM sodium phosphate (pH 7.6), 5×Denhardt's solution, 10% dextran sulfate, and 20 u/ml denatured, sheared salmon sperm DNA, followed by washing the filters in 0.1× SSC at about 65° C., or equivalent conditions. Equivalent conditions are easily determined by one of ordinary skill in the art using methods and materials publicly known and available.

Variegation. As used herein, the term "variegation" refers to a change in phenotype due to mutation during somatic development.

Wild-type enzyme. As used herein, the term "wild-type enzyme" refers to an enzyme that will be active at a level of activity found in nature and typically comprises an amino acid sequence found in nature.

The invention is directed, in one aspect, to a method of modulating chromatin structure, the method comprising altering expression of PARP-e. In one embodiment of the method, when expression of PARP-e is increased, the expression of PARP-1 is increased. In another embodiment of the method, when expression of PARP-e is decreased, the expression of PARP-1 is decreased. In a different embodiment, the chromatin is present in a eukaryotic cell. In another embodiment, the chromatin is present in a plant cell. In a preferred embodiment, the chromatin is present in an animal cell. In a highly preferred embodiment the cell is an embryonic cell. In another highly preferred embodiment, the cell is a stem cell.

In another embodiment of the method, the chromatin structure is selected from the group consisting of heterochromatin and repetitive sequences. In a preferred embodiment, modulation of chromatin structure results in gene activation. In a different preferred embodiment, modulation of chromatin structure results in gene repression. In a highly preferred embodiment, the increased PARP-e expression effects chromatin decondensation. In another highly preferred embodiment, the decreased PARP-e expression effects chromatin condensation.

The invention is also directed, in another aspect, to an isolated nucleic acid molecule comprising a polynucleotide having a nucleotide sequence at least 95% identical to a sequence selected from the group consisting of the nucleotide sequence of the DNA contained in Genbank Accession No. AF533701 (SEQ ID NO: 1) or Genbank Accession No. AF533702 (SEQ ID NO: 10). In another embodiment, the invention is directed to an isolated nucleic acid molecule comprising the nucleotide sequence of Genbank Accession No. AF533701 (SEQ ID NO: 1) or Genbank Accession No. AF533702 (SEQ ID NO: 10).

In another aspect, the invention is direct to an isolated PARP-e protein which comprises an amino acid sequence at least 95% identical to the amino acid sequence of SEQ ID NO: 2. In a different aspect, the invention is directed to an isolated protein comprising an amino acid sequence at least 90% identical to amino acids 1 to 613 of SEQ ID NO: 2 wherein the protein has the activity of modulating chromatin structure.

In a preferred embodiment, the invention is directed to an isolated polynucleotide molecule selected from the group consisting of a) a polynucleotide molecule having at least 95% sequence identity to SEQ ID NO: 1; b) a polynucleotide molecule which is a fragment of a); and, c) a polynucleotide molecule which is the complementary nucleotide sequence of (a) or b). In one embodiment, the isolated polynucleotide molecule has SEQ ID NO: 1. In another embodiment, the invention is directed to an isolated polynucleotide molecule comprising the polynucleotide having SEQ ID NO: 1.

In yet a different embodiment, the invention is directed to an isolated PARP-e protein having an amino acid sequence selected from the group consisting of: a) the amino acid sequence as set forth in SEQ ID NO. 2; and, b) the amino acid sequence encoded by a polynucleotide which hybridizes under stringent conditions to a polynucleotide having a nucleotide sequence as set forth in SEQ ID NO. 1; c) the amino acid sequence encoded by a polynucleotide having a nucleotide sequence at least 95% identical to a sequence selected from the group consisting of the nucleotide sequence of the DNA contained in Genbank Accession No. AF533701 (SEQ ID NO: 1) or Genbank Accession No. AF533702 (SEQ ID NO: 10); and, d) the amino acid sequence encoded by an isolated nucleic acid molecule comprising the nucleotide sequence of Genbank Accession No. AF533701 (SEQ ID NO: 1) or Genbank Accession No. AF533702 (SEQ ID NO: 10).

The invention is also directed to a method of inhibiting the growth of an insect, comprising: a) creating an insertion mutation in the insect PARP-e gene of a first early insect embryo; b) culturing said first embryo to produce an insect of a first mutant strain; c) creating an insertion mutation in the insect PARP-e gene of a second early insect embryo; d) culturing said second embryo to produce an insect of a second mutant strain; e) mating an insect of said first mutant strain with an insect of said second mutant strain; wherein larvae that contain both said first and second mutations show inhibited growth as compared to an insect not comprising both said first and second mutations. In a different aspect, the invention is also directed to a method of inhibiting the growth of an insect, comprising: a) contacting embryonic insect cells with a composition comprising an effective amount of a dsRNA molecule specific for PARP-e, wherein contact with said dsRNA molecule inhibits growth of said insect. In a preferred embodiment, the insect is a *Drosophila* fly.

The role of PARP on gene expression during the life cycle is studied herein. PARP protein is found throughout chromosomes, but poly(ADP-ribose)-modified proteins are enriched in polytene chromsome puffs, suggesting that PARP is differentially active in these regions. ADP-ribosylated proteins accumulate immediately following heat shock at the 87A and 87C puffs. In Parp mutant larvae, heat shock-induced puffing at these sites and Hsp70 production was strongly reduced. Bacterial infection induces elevated levels of ADP-ribosylation at certain chromosome sites. Parp mutants are abnormally susceptible to bacterial infection, and fail to normally activate Drosopterin and Diptericin, two NF-κB-dependent innate immune response genes. These observations support the idea that PARP plays a critical part in remodeling chromatin at a wide variety of times during *Drosophila* development as well as in response to environmental stresses including DNA damage. Puffs may be a physical manifestation of this type of chromatin-based transcriptional activation.

Mutations in the heterochromatic Parp gene have been characterized. Rather than simply functioning as a repair enzyme, Parp is necessary for viability and to organize the chromatin structure of nucleoli, heterochromatin and other sequences during development. Reduction of Parp function causes hyperexpression of the copia retrotransposon and enhances the variegation of GAL4 transgenes. Studies herein show that Parp plays a fundamental role in organizing chromatin structure during *Drosophila* development, and suggest that ADP-ribosylation of chromosomal proteins plays an important role in chromatin remodeling.

Proteins and Polypeptides

The present invention relates to a PARP-e protein which has the deduced amino acid sequence of SEQ ID NO:2 as well as fragments, analogs and derivatives of such polypeptide.

The terms "fragment," "derivative" and "analog" when referring to the polypeptide of SEQ ID NO:2 means a polypeptide which retains essentially the same biological function or activity as the polypeptide. Thus, an analog includes a proprotein which can be activated by cleavage of the proprotein portion to produce an active mature polypeptide. The polypeptide of the present invention may be a recombinant polypeptide, a natural polypeptide or a synthetic polypeptide, preferably a recombinant polypeptide.

The fragment, derivative or analog of the polypeptide of SEQ ID NO:2 may be (i) one in which one or more of the amino acid residues are substituted with a conserved or non-conserved amino acid residue (preferably a conserved amino acid residue) and the substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide, or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art using the teachings herein.

The polypeptides of the present invention include the polypeptide of SEQ ID NO:2 as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide. Fragments or portions of the polypeptides of the present invention may be employed for producing the corresponding full-length polypeptide by peptide synthesis; therefore, the fragments may be employed as intermediates for producing the full-length polypeptides.

The invention further provides an isolated Parp-e peptide having the amino acid sequence encoded by the cDNA (SEQ ID NO: 1), or the amino acid sequence in SEQ ID NO:2, or a peptide or polypeptide comprising a portion of the above polypeptides. It will be recognized in the art that some amino acid sequences of the peptide can be varied without significant effect of the structure or function of the protein. If such differences in sequence are contemplated, it should be remembered that there will be critical areas on the protein which determine activity.

Thus, the invention further includes variations of the PARP-e protein which show substantial activity or which include regions of partial peptide activity such as the protein portions discussed below. Such mutants include deletions, insertions, inversions, repeats, and type substitutions. As indicated above, guidance concerning which amino acid changes are likely to be phenotypically silent can be found in Bowie et al., Science 247:1306 (1990).

As indicated, changes are preferably of a minor nature, such as conservative amino acid substitutions that do not significantly affect the folding or activity of the protein. Amino acids in the PARP-e protein of the present invention that are essential for function can be identified by methods known in the art, such as site-directed mutagenesis or alanine-scanning mutagenesis (Cunningham et al. 1989. Science 244: 1081-1085). The latter procedure introduces single alanine mutations at every residue in the molecule. The resulting mutant molecules are then tested for biological activity such as receptor binding or in vitro, or in vivo proliferative activity. Sites that are critical for ligand-receptor binding can also be determined by structural analysis such as crystallization, nuclear magnetic resonance or photoaffinity labeling (Smith et al. 1992. *J. Mol. Biol.* 224:899-904 and de Vos et al., 1992. *Science* 255:306-312).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell.

By a polypeptide having an amino acid sequence at least, for example, 95% "identical" to a reference amino acid sequence of a peptide is intended that the amino acid sequence of the polypeptide is identical to the reference sequence except that the polypeptide sequence may include up to five amino acid alterations per each 100 amino acids of the reference amino acid of the peptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The accession numbers, and the nucleotide sequences which they designate, are available through publicly accessible genomic data bases such as GenBank, and the Berkeley *Drosophila* Genome Project. The sequence of the polynucleotides contained in the accession numbers, as well as the amino acid sequence of the polypeptides encoded therefrom, are incorporated herein by reference.

Polynucleotides and Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Isolated nucleic acid molecules of the present invention include, for example, the DNA molecule shown in SEQ ID NO:1; DNA molecules comprising the coding sequence for the Parp-e protein; and DNA molecules which comprise a sequence substantially different from those described above but which, due to the degeneracy of the genetic code, still encode the Parp-e protein. Of course, the genetic code is well known in the art. Thus, it would be routine for one skilled in the art to generate such degenerate variants.

The present invention is further directed to fragments of the isolated nucleic acid molecules described herein. By a fragment of an isolated nucleic acid molecule having the nucleotide sequence of a DNA encoding PARP-e or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, or 323 nt in length are also useful according to the present invention as are fragments corresponding to most, if not all, of the nucleotide sequence of a DNA encoding the PARP-e protein or as shown in SEQ ID NO:1. By a fragment at least 20 nt in length, for example, is intended fragments which include 20 or more contiguous bases from a nucleotide sequence of a DNA encoding PARP-e or the nucleotide sequence as shown in SEQ ID NO:1.

In another aspect, the invention provides an isolated nucleic acid molecule comprising a polynucleotide which hybridizes under stringent hybridization conditions to a portion of the polynucleotide in a nucleic acid molecule described above, for instance, SEQ ID NO: 1 or SEQ ID NO: 10.

Hybridization

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

For preliminary screening for homologous nucleic acids, low stringency hybridization conditions, corresponding to a $T_m$ of 55° can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 ug/ml denatured, sheared salmon sperm DNA, followed by washing the filters in 0.1×.SSC at about 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 12 nucleotides; preferably at least about 16 nucleotides; and more preferably the length is at least about 24 nucleotides; and most preferably 36 nucleotides.

Fragments of the PARP-e gene (SEQ ID NO: 1) may be used as a hybridization probe for a cDNA library to isolate the full length cDNA and to isolate other cDNAs which have a high sequence similarity to the PARP-e gene or encode a protein having similar biological activity. Probes of this type preferably have at least 30 bases and may contain, for example, 50 or more bases. The probe may also be used to identify a cDNA clone corresponding to a full length transcript and a genomic clone or clones that contain the complete PARP-e gene including regulatory and promotor regions, exons, and introns. An example of a screen comprises isolating the coding region of the gene by using the known DNA sequence to synthesize an oligonucleotide probe. Labeled oligonucleotides having a sequence complementary to the PARP-e gene are used to screen a library of cDNA, genomic DNA or mRNA to determine which members of the library the probe hybridizes to. The screen is not limited to use in any particular type of organism, all that is required is that the organism have nucleic acids.

The present invention further relates to polynucleotides which hybridize to the above described sequences if there is at least 70%, preferably at least 90%, and more preferably at least 95% identity between the sequences. The present invention particularly relates to polynucleotides which hybridize under stringent conditions to the polynucleotides described herein. As herein used, the term "stringent conditions" means hybridization will occur only if there is at least 95% and preferably at least 97% identity between the sequences. The polynucleotides which hybridize to the polynucleotides described herein in a preferred embodiment encode polypeptides which retain substantially the same biological function or activity as the polypeptide encoded by the cDNA of SEQ ID NO:1 or the polypeptide having SEQ ID NO:2.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed herein.

By a portion of a polynucleotide of "at least 20 nt in length," for example, is intended 20 or more contiguous nucleotides from the nucleotide sequence of the reference polynucleotide (e.g., the nucleotide sequence as shown in SEQ ID NO:1).

The present invention further relates to variants of the nucleic acid molecules of the present invention, which encode portions, analogs or derivatives of the PARP-e protein. Variants may occur naturally, such as a natural allelic variant. By an "allelic variant" is intended one of several alternate forms of a gene occupying a given locus on a chromosome of an organism. Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Parp-e protein or portions thereof. Also especially preferred in this regard are conservative substitutions.

By a polynucleotide having a nucleotide sequence at least, for example, 95% "identical" to a reference nucleotide sequence encoding a PARP-e protein is intended that the nucleotide sequence of the polynucleotide is identical to the reference sequence except that the polynucleotide sequence may include up to five point mutations per each 100 nucleotides of the reference nucleotide sequence encoding the protein. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or to the nucleotide sequences of GenBank accession nos. AF533701 and AF533702, can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO: 1 or to the nucleotide sequences of GenBank accession nos. AF533701 and AF533702, irrespective of whether they encode a polypeptide having Parp-e activity. This is because even where a particular nucleic acid molecule does not encode a polypeptide having Parp-e activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Parp-e activity include, for example, (1) isolating the Parp-e gene or allelic variants thereof in a cDNA library; (2) in situ hybridization to metaphase chromosomal spreads to provide precise chromosomal location of the Parp-e protein gene (Verma et al., Human Chromosomes: A Manual of Basic Techniques, Pergamon Press, New York (1988)); and Northern Blot analysis for detecting Parp-e mRNA expression in specific tissues. Preferred, however, are nucleic acid molecules having sequences at least 95%, 96%, 97%, 98% or 99% identical to a nucleic acid sequence shown in SEQ ID NO:1 or to the nucleic acid sequence of GenBank accession nos. AF533701 (SEQ ID NO: 1) and AF533702 (SEQ ID NO: 10), which do, in fact, encode a protein having Parp-e protein activity Of course, due to the degeneracy of the genetic code, one of ordinary skill in the art will immediately recognize that a large number of the nucleic acid molecules having a sequence at least 95%, 96%, 97%, 98%, or 99% identical to a nucleic acid sequence of GenBank accession nos. AF533701 (SEQ ID NO: 1) or AF533702 (SEQ ID NO: 10), or to a nucleic acid sequence shown in SEQ ID NO:1 will encode a polypeptide having Parp-e protein activity. Since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Parp-e protein activity. This is because the skilled artisan is fully aware of amino acid substitutions that are either less likely or not likely to significantly effect protein function (e.g., replacing one aliphatic amino acid with a second aliphatic amino acid).

Due to the degeneracy of nucleotide coding sequences, other DNA sequences which encode substantially the same amino acid sequence as a Parp-e gene may be used in the practice of the present invention including those comprising conservative substitutions thereof. These include but are not limited to modified allelic genes, modified homologous genes from other species, and nucleotide sequences comprising all or portions of Parp-e genes which are altered by the substitution of different codons that encode the protein.

Standard Techniques

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory Press, Plainview, N.Y.; Maniatis et al. (1982) Molecular Cloning, Cold Spring Harbor Laboratory Press, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley;

Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; and Setlow and Hollaender (1979) Genetic Engineering: Principles and Methods, Vols. 1-4, Plenum Press, New York. Abbreviations and nomenclature, where employed, are deemed standard in the field and commonly used in professional journals such as those cited herein.

EXAMPLES

Example 1

Drosophila Strains and Genetics

Genetic markers are described in Flybase (1999) (FlyBase 1999. *Nucleic Acids Res.* 27: 85-88) and stocks were obtained from the Bloomington Stock Center except as indicated. The CH(3)1 and CH(3)4 strains were generated in a single P-element mutagenesis screen (Zhang et al. 1994). CH(3)1 was found to be viable in combination with Df(3R)10-65; Southern blotting indicated that this deletion does not remove PARP coding sequences (data not shown). y $w^{67c23(2)}$ was used as the host for transformation. The driver strain for the rescue experiments was P{GAL4-arm.S} (armGAL4)} (Sanson et al. 1996. *Nature.* 383: 627-630). The 69B GAL4 driver is described by Brand (Brand et al. 1993. *Development.* 118: 401-415). Sir2$^{05237}$ was constructed by Karpen et al. (Karpen et al. 1992. *Genetics.* 132: 737-753) and is described by Rosenberg and Parkhurst (2002). Balancer chromosomes carrying Kr-GFP were used to differentiate homozygous mutant embryos and larvae: TM3, Sb, P{w$^+$, Kr-GFP} and CyO, P{w$^+$, Kr-GFP} (Casso et al 2000. *Mech. Dev.* 91: 451-454). Imprecise excision of CH(3)1 was carried out as described previously (Zhang et al. 1994). Transformation experiments were carried out as described in Tulin et al. (2002) using the y $w^{67c23(2)}$ strain as host.

Example 2

Developmental Timing Measurements

Embryos were collected on grape juice/agar plates for 2 hours at 25° C., aged 10-12 hours, and subsets were subsequently analyzed each 1-2 hours during daytime for 4-8 days. Larval stages were identified by mouth hook and/or posterior appendage morphology.

Example 3

Construction of Transgenic Drosophila

For the rescue experiments, pP{w+, UAST-PARP-I} was constructed by cloning the NotI/KpnI fragment encoding PARP-I from cDNA LD02455 into the pUAST vector. pP{w+, UAST-PARP-e} was constructed by fusing a NotI/KpnI fragment encoding PARP-e from cDNA GM 10715 into pUAST. To detect protein localization in vivo, PARP-I cDNA was fused to DsRed (Clontech Laboratories) in pP{w+, UAST-PARP-I-DsRed} and PARP-e was fused to EGFP (Clontech Laboratories) in pP{w+, UAST-PARP-e-EGFP}. To study the variegation of UAS constructs we built pP{w+, UAST-Tim17b-DsRed}, which contains a Tim17b cDNA fused in frame to DsRed (Clontech Laboratories) in pUAST. Transformation was as described (Spradling et al. 1982. *Science.* 218: 341-347), with modifications (Prokhorova et al. 1994. *Genetika (Moscow).* 30: 874-878).

Example 4

Genomic Mapping and Sequencing

A physical map of the Parp region was constructed using cDNA libraries (Rubin et al. 2000. *Science* 287: 2222-2224) and a P1 library (Kimmerly et al.1996) from the Berkeley *Drosophila* Genome Project (BDGP). Clone DS09016 was subcloned into pTZ 19R using XbaI or EcoRI digestion and sequenced. The following cDNAs were sequenced and used to express PARP isoforms: LD02455 (Parp-I) and GM10715 (Parp-e, SEQ ID NO: 1). In addition, 13 other Parp cDNAs were fully sequenced. To determine the location of transcribed exons in the Parp region (FIG. 2) we also fully sequenced the following cDNAs: SD15682 (TK), RE01394 (Tim23), CK01513 (Tim17b) and LP01513 (no ORF).

Example 5

Fluorescent In Situ Hybridization (FISH)

Mitotic chromosomes were prepared as described by Layerty (web site: fruitfly.org/mlthods/cytogenetics). Probe preparation by nick translation, pretreatment, hybridization and signal detection were performed as previously described (Dej et al. 1999. *Development* 126: 293-303). cDNA LD02455 was used to detect Parp coding sequences, and the PZ element without rosy gene sequences (Karpen and Spradling, 1992) was used to detect the PZ insertion in CH(3)1.

Example 6

Double Stranded RNA Interference (dsRNAi)

RNAi was prepared as described by Kennerdell (Kennerdell et al. 1998. *Cell* 95: 1017-1026). The following regions were targeted: 269-864 for GM10715, 1-604 for LD02455 and 485-891 for copia. DsRNAi was injected into the posterior region of precellular blastoderm embryos at a concentration 0.5 ug/ul and the embryos were allowed to develop for an appropriate period under oil in a humid chamber prior to analysis.

Example 7

RT-PCR and Northern Blot

Total RNA was isolated using Trizol reagent (Gibco BRL), precipitated twice with 3M LiCl, treated with Amplification Grade Dnase I (Gibco BRL) and poly(A)-containing RNA purified using a MessageMarker kit (Gibco BRL). The Super-Script Preamplification System (Gibco BRL) was then used to synthesize cDNA and for RT-PCR. The following primers were used to distinguish PARP-I and PARP-e transcripts: PI (5'-aaataataaatgtcttgaaattg-3') (SEQ ID NO: 3) for PARP-I, PIII (5'-gtcttgattttgtgtataccg-3') (SEQ ID NO: 4) for PARP-e and R4 (5'-ttttatgaaaccaattcg-3') (SEQ ID NO: 5) for both. Total Parp transcripts were detected using: D1 (5'-gtgtcgtggatgtgaac-3') (SEQ ID NO: 6) and R2 (5'-ttggaattctggattttg-3') (SEQ ID NO: 7) which target a common coding region within the DNA binding domain. Copia-specific transcripts were detected using: 5'-copia (5'-ccgtttgatggcgagaagtacgcgatttgg-3') (SEQ ID NO: 8) and 3'-copia (5'-ccatcgtaacacgaaggcaatgtgatc-3') (SEQ ID NO: 9) which target part of ORF1. For Northern blot analysis, at least of 2.5 ug of poly(A) RNA from second instar larvae was used per each lane. The PARP probe was from the DNA binding domain, while an rp49 probe was used as a control.

Example 8

Nuclease Sensitivity Assays

Embryos were collected on grape juice/agar plates for 2 hours at 25° C., aged for 12 hours or an appropriate period. The micrococcal nuclease sensitivity of purified nuclei was determined as described by Wu (Wu. 1989. *Methods Enzymol.* 170: 269-289) and Quivy (Quivy et al. 1997. *Methods.* 11: 171-179) with minor modifications. Controls showing the absence of endogenous nuclease activity were carried out, and the levels of micrococcal nuclease used were calibrated for each stock.

Example 9

Immunohistochemistry and Fluorescence Microscopy

Tissues were fixed and stained with primary and secondary antibodies as described previously (Grieder et al. *Development.* 127: 4253-4264) and examined by confocal microscopy using a Leica TCS-NT microscope. Primary antibodies were: mouse monoclonal (mAb) Aj 1 (1:100) and anti-fibrillarin (1:200) (from J. Gall); and mouse mAb 10H (1:20-50) from Dr. Manfred Frey (Steinbeis-Transferzentrum fur Angewandte Biologische Chemie). 10H specifically recognizes ADP-ribose polymers (Kawamitsu et al. 1984. *Biochemistry.* 23: 3771-3777). Nuclear staining by 10H such as that shown in FIG. 8F was abolished in Parp mutant larvae, further confirming the specificity of this reagent (data not shown). Mouse Alexa-568 (Molecular Probes) (1:400) was used as a secondary antibody.

Example 10 pADPr Assay

Embryos were collected and nuclei purified as for the nuclease sensitivity assay. Nuclei were incubated in nuclear buffer (Quivy 1997) containing 0.1 mCi/ml of [$^{32}$P]-NAD (Amersham) for 15 minutes at room temperature. Then nuclei were washed twice in nuclear buffer, collected by centrifugation, preheated for 3 minutes. The protein gel was processed, dried and subjected to autoradiography.

Example 11

Antibodies and Microscopy

Primary antibodies were: mouse monoclonal (mAb) Aj1 (1:100) and anti-fibrillarin (1:200) (from J. Gall); and mouse mAb 10H (1:20-50) from Dr. Manfred Frey (Steinbeis-Transferzentrum fur Angewandte Biologische Chemie). Anti-poly (ADP-ribose) antibody was obtained from Mouse Alexa-568 (Molecular Probes) (1:400). Rabbit polyclonal anti-fibrillarin antibody labels nucleoli; mouse mAb h10 (Steinbeis-Transferzentrum fur Angewandte Biologische Chemie) recognizes the branch sites of (ADP-ribose) polymers; anti-actin (Sigma) recognizes *Drosophila* actin; rabbit polyclonal anti-GFP (Promega) recognizes PARP-EGFP in fixed tissue, and Drosomycin-GFP on Western Blots (Jung et al. 2000. Biotechniques 30: 594), mouse monoclonal anti-lacZ (Promega) recognizes Diptericine-lacZ; anti-Hsp70 recognizes Hsp70 on Western blots; Biotinylated NAD (Trevigen) was detected with avidin-rhodamine (Roche). 3-AB (Sigma) was used at a concentration of 2.5 mM.

Tissues were fixed and stained with fluoresceinated antibodies as described previously (Grieder et al. 2000) and examined by confocal microscopy using a Leica TCS-NT microscope.

Example 12

Construction of PARP-I-dsRed and Construction of PARP-e-EGFP

The construction of flies expressing PARP-EGFP or PARP-DsRed was described previously and these lines gave identical pattern of fluorescence (Tulin et al. 2002). Drosomycin-GFP and Diptericine-lacZ reporter genes are described (Jung et al. 2000). Oligreen (Molecular Probes) and propidium iodide (Sigma) were used to stain DNA. Transformation of *Drosophila* embryos was as described (Spradling et al. 1982), with modifications (Prokhorova et al. 1994).

Example 13

Infection Assay

Embryos were challenged by injecting a sublethal dose of approximately 2×10$^4$ *E. coli* bacteria or a similar volume of sterile buffer. Survival of the injected animals was followed through adulthood and a fraction of the animals were removed and the presence of bacteria in the haemolymph and in tissues was studied by DAPI staining and microscopic examination.

Example 14

Polytene Chromosome Analysis

The protocol of Lavrov et al. was used to prepare polytene chromosomes for antibody staining, except that fixative included 10% trichloroacetic acid to block PARP glycohydrolase activity when the h10 antibody was to be used. Polytene chromosomes from second instar larvae were prepared as described by Paro et al. to preserve chromosomal proteins prior to antibody binding. Following binding of primary Ab, they were washed and secondary Ab was added. Finally, the chromosomal DNA was labeled with TODO3 and the preparations were examined using a Leica NTS.

Example 16

Heat Shock Protocol for Puff Experiments

PARP inhibitors: GPI 6150, 3-aminobenzamide, DPQ; PJ34=N-(6-oxo-5,6-dihydro-phenanthridin-2-yl)-N,N-dimethylacetamide (Inotek Corp)., TZM, NU 1025.

Results

Sequences Encoding a Novel PARP Isoform are Expressed in Embryos

The previously determined structure of the genomic region encoding Parp-I is shown on the right in FIG. 1A (Hanai et al. 1998; Adams et al. 2000). To search for additional Parp transcripts, clones corresponding to 14 Parp-related EST sequences (Rubin et al. 2000) were analyzed, and GM 10715, derived from an early ovarian RNA library, was found to differ from Parp-I. The complete sequence of GM10715

(SEQ ID NO: 1) was determined, revealing an additional 920 bp intron within exon 8 encoding the PARP catalytic domain as well as 287 bp of novel 5' sequence that splice into the first Parp-I exon (exon 3) about 40 bp downstream from its 5'-end but 6 bp before the AUG codon (FIG. 1A). The PARP isoform predicted by GM10715, which we name PARP-e ("embryonic") (SEQ ID NO: 2), should lack enzymatic function since the new intron removes conserved amino acids essential for catalytic activity including the NAD binding site.

Previous studies of Parp-I production showed that transcripts are abundant in late-stage ovarian follicles and embryos, but did not distinguish between transcripts encoding different isoforms (Hanai et al. 1998). We analyzed Parp expression throughout the Drosophila lifecycle using Northern blots (FIG. 1B), whole mount in situ hybridization (FIG. 1C) and RT-PCR with specific primers to distinguish Parp-e from Parp-I and II (FIG. 1D). The 3.2 kb Parp-I RNA and 2.6 kb Parp-II or Parp-e RNAs are expressed in ovaries, embryos and adults. In contrast to previous results, low levels of the 3.2 kb Parp-I mRNA remain in $2^{nd}$ instar larvae (FIG. 1B). In the ovary, nurse cells express Parp RNA beginning as early as stage 4, while male germ cells strongly express Parp until the spermatid stage (not shown). Parp-e expression is detected only in adult ovaries and embryos (FIG. 1D).

To further analyze Parp expression, we constructed and expressed epitope-tagged versions of the two major PARP isoforms in flies. When expressed using this UAS/GAL4 based system, PARP-I (FIG. 1E) and PARP-e (not shown) are both highly enriched in nucleoli, heterochromatic chromosomal regions and diverse euchromatic sites in the cells of most embryonic and adult tissues. The distribution of ADP (ribosyl)-modified proteins, as revealed by immunostaining with an antibody specific for ADP-ribose polymers (Kawamitsu et al. 1984), was very similar, strongly labeling these same regions within nuclei (FIG. 1F). These experiments provide a clearer picture of developmentally regulated Parp expression and show a correlation between PARP protein and protein ADP(ribosyl) moieties.

Parp Spans a Large Region of 3R Heterochromatin

Figure 2:
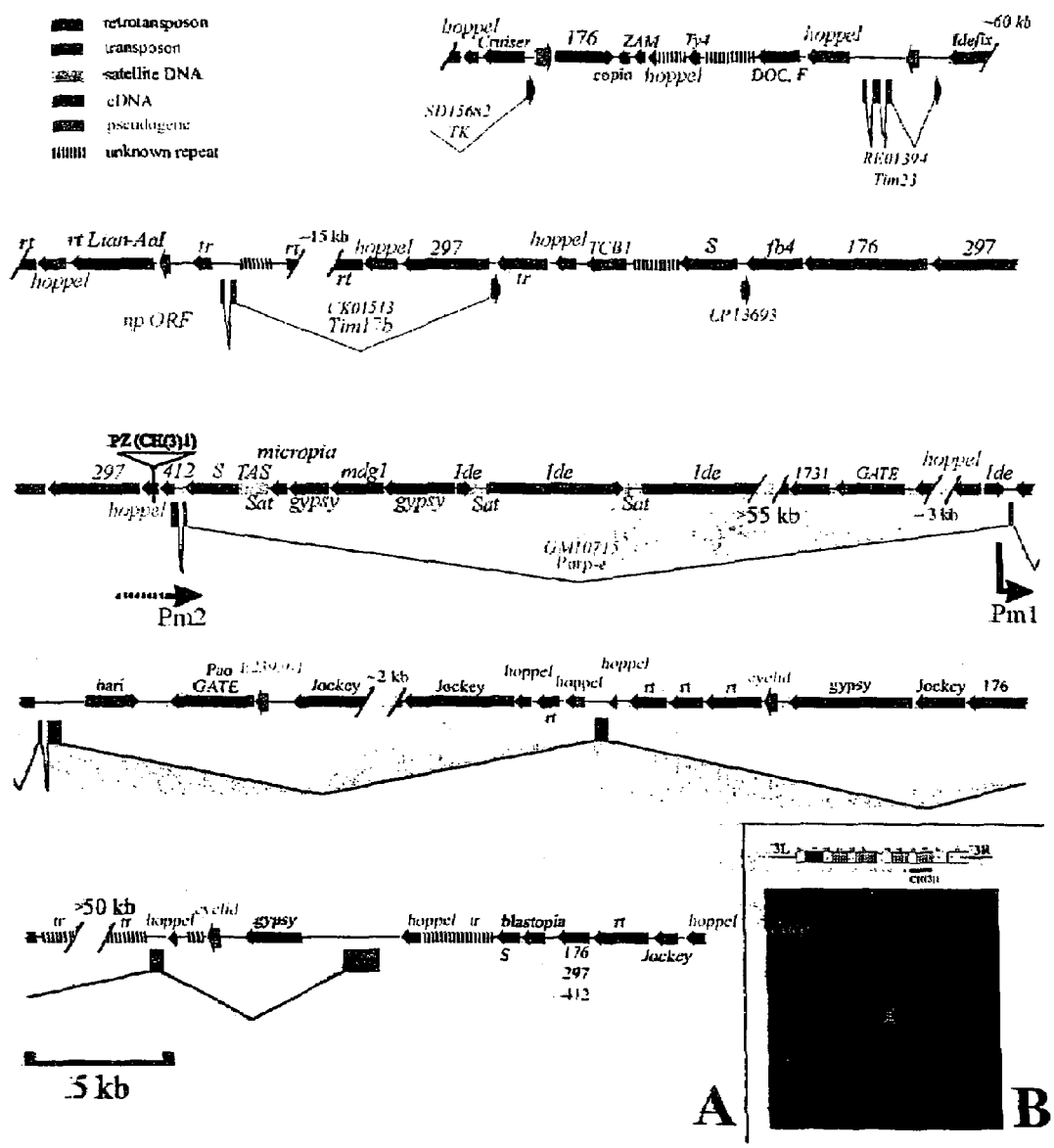
FIGS. 2A-B. DNA sequence of the heterochromatic region containing Parp. (A) A diagram summarizing the sequence organization of the region as determined from this study (see Examples) and from Adams et al. (2000) is shown. Genes defined by cDNAs sequenced as part of this study are shown in red (boxes are exons). The names of retrotransposons (black) and of transposons (blue) are given above the region of homology represented as an arrow (arrowhead-3' end). Regions containing only small sequence blocks related to a particular transposon are indicated by parallel bars. The position of the CH(3)1 insertion and the location of the putative Parp promoters Pm1 and Pm2 are indicated. Gaps in the sequence of known or estimated size are represented by hash marks. (B) An ideogram of chromosome 3 heterochromatin shows the cytological region of CH(3)1 insertion (Zhang et al. 1994). Below, a chromosome set from a CH(3)1/T3 third instar larval neuroblast is shown that has been hybridized in situ with a Parp cDNA (green) and transposon-specific sequences (red). The partial overlap of the Parp and CH(3)1 sequences indicates that Parp and CH(3)1 are located near each other in 3 R heterochromatin. (Note: the TOTO-3 used for this confocal micrograph does not reveal full morphological detail; but chromosomes were also scored using DAPI; CH(3)1 was localized previously to h55 (Zhang et al. 1994)).

The structure of GM10715 implies that some Parp transcripts originate from a novel promoter(s), which we denote Pm2, located at or upstream from the GM10715 5' end. Using the isoform-specific 5' portion of GM 10715 as a probe, six overlapping clones spanning approximately 100 kb of genomic DNA flanking the 5' region of Parp-e were isolated from a Drosophila P1 genomic library and used to map and sequence this region (FIG. 1A, FIG. 2). P1 clones were also recovered from the genomic region encoding Parp-I. At least 55 kb separates the upstream Parp-e sequence contig defined by DS09016 from the non-overlapping Parp-I 5' sequence contig AE002935. Sequence identity was also observed between the upstream region and the DNA flanking a previously described heterochromatic P element insertion, CH(3)1 (Zhang et al. 1994). To confirm that the upstream region defined by GM10715 and CH(3)1 really lies adjacent to PARP coding sequences, we showed that probes specific for PARP coding sequences and for the CH(3)1 insertion generated overlapping in situ hybridization signals on metaphase chromosomes (FIG. 2B). The CH(3)1 P element insertion was mapped previously to region h55-h56 of 3R heterochromatin (Zhang et al. 1994). Taken together, these studies define the structure of the Parp locus and confirm its location in the heterochromatin of chromosome 3R.

Analyzing the genomic DNA sequence surrounding the Parp transcription unit revealed several striking features of this 300 kb heterochromatic chromosome region (FIG. 2A). About 210 kb (70%) lies within Parp and 4 other genes, including a thiamine kinase ortholog (TK) and two apparent mitochrondrial translocase subunits (Tim17b and Tim23). Most of the DNA within and surrounding the genes consists of transposons (blue) and retrotransposons (black) that are strikingly organized over the entire region studied. Nearly all are oriented in the same direction on the chromosome and opposite to the genes. These transposons have lost LTR homologies, and the gypsy elements lack insulator sequences that can disrupt enhancer-promoter interactions. Because unselected genomic sequences diverge rapidly during Drosophila evolution, our observations suggest that in recent evolutionary time the Parp region underwent extensive transposon invasion subject to some large-scale selective or mechanistic constraint On insertional orientation.

CH(3)1 Defines a Complementation Group that Disrupts Parp Expression

Figure 3:
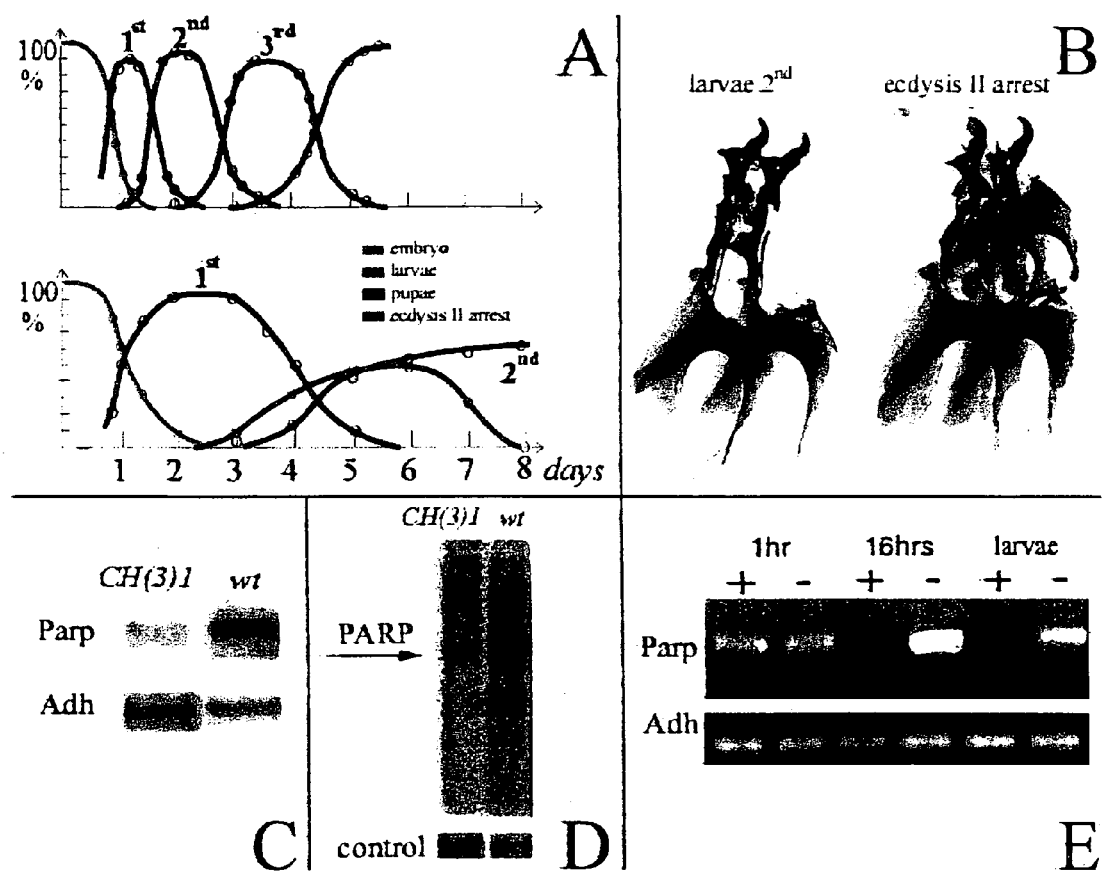
FIGS. 3A-E. The CH(3)1 complementation group disrupts Parp expression and activity. (A) Timelines of development of wild type (above) and CH(3)1 homozygotes (below) are shown. The fraction of animals at each developmental stage are plotted as a function of time, revealing the strong developmental delay caused by CH(3)1. (B) Preparation of larval mouth hooks, which distinguish larval instars, are illustrated showing the characteristic appearance of the normal 12 mouthhooks (left) and of mouthhooks from CH(3)1 mutants arrested at the onset of ecdysis 2 (right). (C) Northern blot of poly(A)-containing RNA from wild type larvae and four days old CH(3)1 larvae showing reduced levels of Parp 3.2 kb mRNA. (D) Proteins labeled by ADP-ribosylation in wild type (wt) and CH(3)1 mutant larvae. An autoradioagram of a gel of $^{32}$P-labeled protein is shown (see Examples). The prominent band at 117 kd in the wild type has the expected molecular weight of PARP itself. Stained protein in a segment of the same gel is shown as a loading control. (E) RNAi treatment of embryos eliminates detectable Parp mRNA in 16 hr embryos and larvae. An RT-PCR assay recognizing all forms of the Parp transcripts is shown; primers specific for the alcohol dehydrogenase gene (Adh) gene serve as a loading control.

We characterized the CH(3)1 strain to learn whether its recessive lethality (Zhang et al. 1994) is caused by disrupting Parp gene function. A second allele of the CH(3)1 locus was found within another P element insertion strain, CH(3)4, but the CH(3)4 P element cannot be responsible for the allelism as it is located on the opposite chromosome arm (3L) and mutates a different gene. However, both CH(3)1 and CH(3) 1/CH(3)4 animals display a similar phenotype. Mutant CH(3)1 homozygotes develop slowly and usually die during the second larval instar after 6-9 days (FIG. 3A). Evidence of mitotic cell cycle defects was not seen; predominantly diploid larval tissues such as the brain are of normal size. However, examination of larval mouth hooks shows that up to 50% of the mutant larvae are arrested at the onset of ecdysis II (FIG. 3B). When the CH(3)1 element was imprecisely excised, about 7% of the derived chromosomes were homozygous viable and complemented CH(3)4, arguing strongly that the CH(3)1 P element was responsible for the original lethality.

If CH(3)1 alleles mutate Parp, then its gene transcripts should be reduced in the affected larvae. As predicted, we found that Parp expression is severely affected in both CH(3)1 and CH(3)1/CH(3)4 animals. 3.2 kb Parp-I mRNA levels are strongly reduced on Northern blots of RNA from mutant larvae (FIG. 3C) and using quantitative RT-PCR (not shown). ADP-ribosylation of proteins is also dramatically decreased in mutants (FIG. 3D). However, the effects observed on all forms of Parp were surprising since mutation of Pm2-initiated transcripts by the CH(3)1 insertion might have been expected to only disrupt production of the 2.6 kb Parp-e mRNA and the enzymatically inactive PARP-e protein isoform. The small amount of Parp mRNA and enzymatic activity that does remain in the mutant larvae might come from transcripts initiated at Pm1 or from remaining maternal stores of Parp transcripts. To try and remove all Parp mRNA, we injected a 587 bp dsRNA specific for Parp into early embryos and observed that all traces of Parp mRNA detectable by RT-PCR were lost after 16 hours of embryonic development (FIG. 3E). More than 70% of the animals receiving Parp RNAi injections, unlike buffer-injected controls, arrested after hatching into first instar larvae, i.e., at an earlier point than in the mutants that retain low levels of residual Parp RNA. These observations further strengthen the connection between the CH(3)1 locus and Parp.

Loss of PARP Derepresses the Copia Retrotransposon

Figure 4:
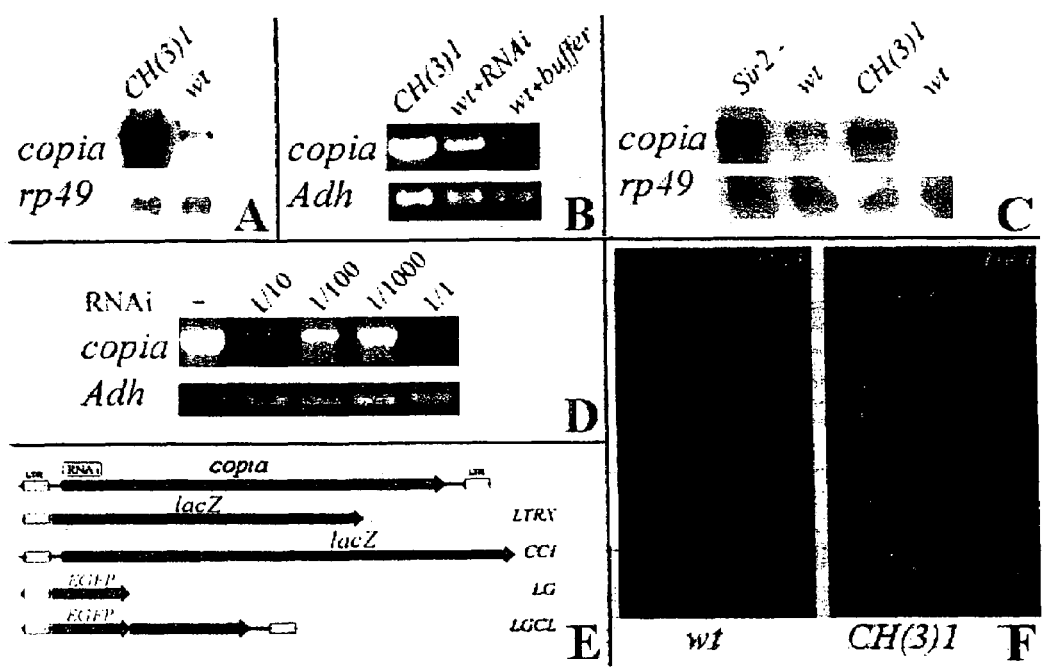
FIGS. 4A-C. Parp mutations or Parp (RNAi) elevate copia transcript levels. (A) A Northern blot of total RNA from $2^{nd}$ instar larvae of the indicated genotypes was probed with copia sequences. The 5.5 kb copia transcript is overproduced up to 50-fold in CH(3)1 or CH(3)4 homozygotes, and in CH(3)1/CH(3)4 trans-heterozygotes compared to wild type. An rp49 probe was used as a loading control. (B) Quantitative RT-PCR shows that injection of Parp-specific RNAi, but not buffer, causes copia RNA to be overproduced. Primers specific to Adh served as a loading control. (C) copia RNA accumulation does not cause lethality. Injection of mutant CH(3)1 embryos with RNAi specific to copia suppressed the accumulation of excess copia RNA and resulted in the elimination of all copia transcripts detectable by RT-PCR within 16 hours. Sequential dilutions of the RNAi gave a graded response. However, the treatment did not rescue larval lethality.

Because Parp is located in transposon-rich heterochromatin, we looked for effects of the mutation on transposon activity. We found that CH(3)1, CH(3)4 and CH(3)1/CH(3)4 animals dramatically overproduce the 5.5 kb transcript of the copia retrotransposon (FIG. 4A). A similar large accumulation of copia-specific RNA was observed in embryos and larvae following injection of Parp-specific RNAi (FIG. 4B), providing further support that the CH(3)1 mutation acts directly on Parp. Tests using several other retrotransposable elements showed no increase in transcripts in CH(3)1 mutant animals, so the increased expression appeared to be specific for copia. Copia hyper-expression in CH(3)1 mutants and normal copia expression in their wild type sibs could be abolished by injecting copia-specific dsRNA into preblastoderm embryos (FIG. 4C) but CH(3)1 lethality was not rescued. Thus, disrupting Parp expression causes copia hyper-expression, but this effect is not responsible for the lethal effects of CH(3)1.

Disrupting Parp Expression Alters Heterochromatin Structure

Figure 5:
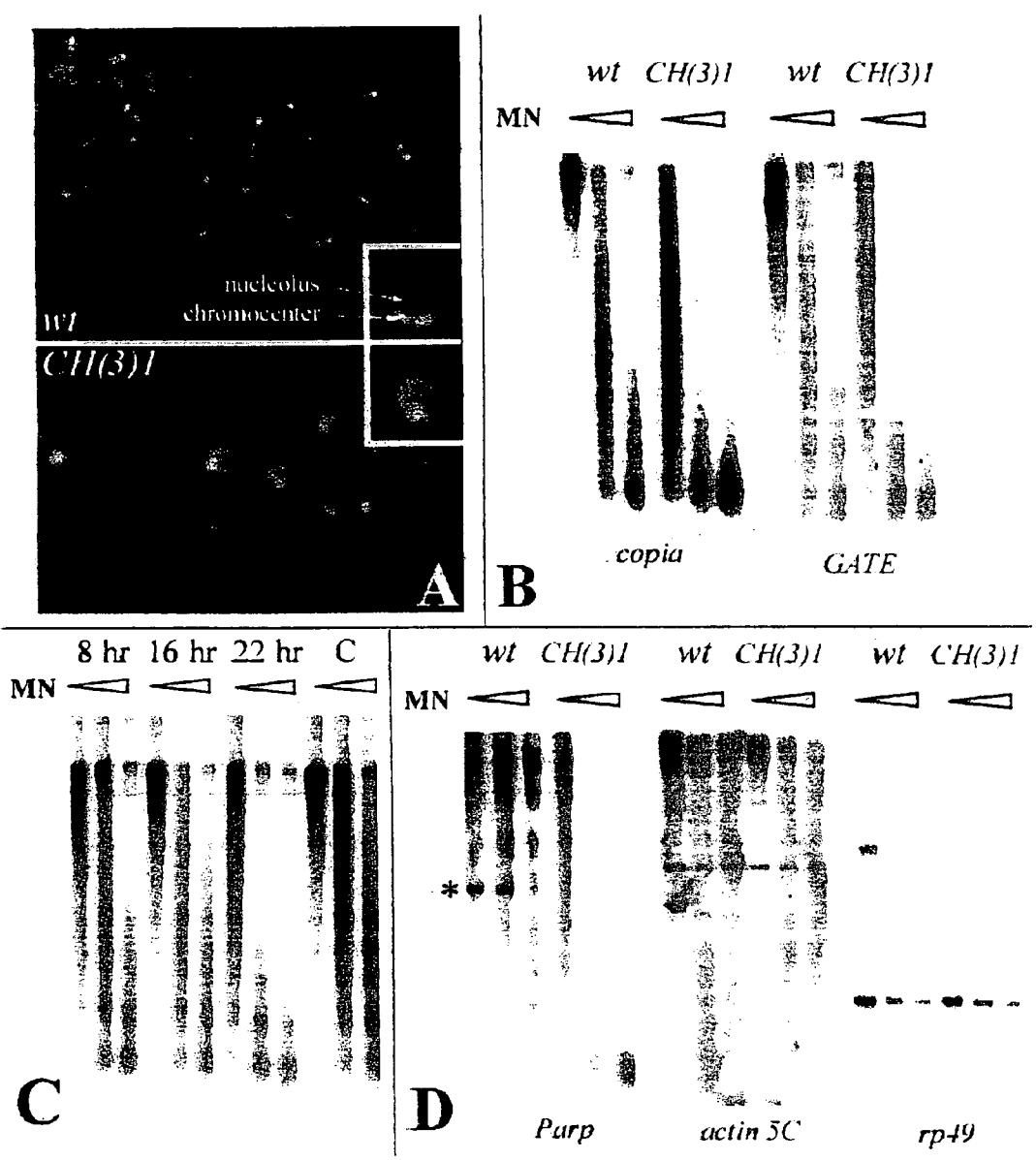
FIGS. 5A-D. Parp mutations alter nuclear morphology and chromatin accessibility to nuclease. (A) DAPI stained nuclei from $2^{nd}$ instar larval salivary glands of wild type (upper) or CH(3)1 mutants (lower). A single nucleus is presented at higher magnification in the insets. Nuclei in the mutant appear more diffuse, have a less distinct chromocenter and lack the region of low DNA density caused by the presence of a normal nucleolus. (B) Nuclei from CH(3)1 mutant larvae were treated with increasing concentrations of micrococcal nuclease (triangles) prior to DNA extraction, digestion with PstI and analysis on Southern blots probed with a copia or GATE probe. Pst digestion produces no small internal fragment of copia or GATE resolvable within the molecular weight range of the gel. At all concentrations, retrotransposon specific sequences were far more sensitive to digestion in the mutant. (C) The same analysis as in (B) was carried out using nuclei at the indicated times after injection of Parp-specific RNAi. copia sequences from RNAi-injected animals become increasingly sensitive to micrococcal nuclease digestion at increasing time after RNAi injection, compared to buffer injected controls (C). (D) Micrococcal nuclease assays were carried out as in (B) and analyzed with a probe from the Parp gene region encoding exons 3, 4 and 5, and with probes specific for the single copy euchromatic genes actin 5C and rp49. Parp sequences are much more accessible to digestion in the mutant, including a band containing exon 3 and Pm1 (asterisk). To ensure that experiments with heterochromatic and single copy probes were comparable, the same blot was used for copia, GATE, actin 5C and rp49. The blot assayed with Parp in (D) was re-probed with copia as a control and showed the same differential digestion as in (B).

The CH(3)1 mutation might affect a transcription factor that negatively regulates copia transcription or it might disrupt a protein that acts at the level of chromatin. We looked for global effects on chromatin by examining DAPI-stained nuclei from various tissues of CH(3)1 homozygotes, and by carrying out nuclease sensitivity experiments. CH(3)1 alleles dramatically alter nuclear morphology (FIG. 5A). DAPI-stained DNA from all mutant tissues examined appears more uniform than wild type, shows a less distinct chromocenter and lacks a nucleolar region of low DNA density. Copia chromatin is specifically affected, because copia-homologous sequences are much more sensitive to micrococcal nuclease digestion within CH(3)1 mutant compared to wild type nuclei (FIG. 5B). Even the lowest levels of nuclease, which digested very little copia-specific DNA in wild type, cleaved it extensively in CH(3)1 homozygotes. Elevated sensitivity could also be induced by injecting Parp-specific RNAi (FIG. 5C).

Many additional nuclease sensitivity tests were carried out to develop a picture of which genomic sequences and regions become nuclease sensitive in the mutant. All the repetitive sequences tested were strongly affected (FIG. 5B, data not shown). These include the transposons GATE, gypsy, mdg1, hoppel, the S element, 297, Idefix, the rDNA-specific R1 element, and the Stellate repeats. In contrast, no changes in micrococcal nuclease sensitivity of the unique euchromatic genes actin 5C and rp49 were observed (FIG. 5D). The single-copy Parp gene resides within a region of highly repetitive sequences including many of the transposons shown to be affected in deficient animals. We tested three Parp exons, including exon 3 which lies adjacent to Pm1, and found that they became much more accessible to nuclease digestion in CH(3)1 homozygotes (FIG. 5C). Taken together, these observations suggest that reducing PARP activity selectively alters the chromatin structure of heterochromatic and repetitive sequences but not of euchromatic, single-copy DNAs.

Expression of PARP-e But Not PARP-I Rescues CH(3)1 Mutations

Despite strongly reduced Parp expression in CH(3)1 mutant animals and the correlation between the mutant phenotype and the effects of removing PARP activity using RNAi, we sought to verify that CH(3)1 mutates Parp by rescue. Because of its size and unclonable structure, it is impractical to attempt rescuing CH(3)1 using genomic Parp DNA. Consequently, we generated constructs that express Parp-I or Parp-e cDNAs under the control of a UAS promoter. Following transformation we studied the effects expressing these cDNAs throughout many tissues using the Armadillo-GAL4 driver. Ectopic expression of Parp-I cDNA, but not Parp-e cDNA, in wild type flies causes rough eyes and abdominal cuticle defects (data not shown). Parp-I expressing animals arrest at the pupal stage if two doses of the driver are present. Thus, as in mammals, excess PARP-I levels cause deleterious effects.

Expressing Parp-e cDNA in a CH(3)1 mutant background revealed that the PARP-e isoform can completely suppress larval lethality and give rise to a small number of viable, fertile adults. Mutant flies bearing two copies of the Parp-e cDNA and driver can be readily maintained as a homozygous stock. In contrast, mutant animals expressing Parp-I cDNA die as third instar larvae but still develop significantly farther than in the absence of the construct. Nonetheless, the ability of Parp cDNAs to partially or wholly rescue CH(3)1 animals demonstrates that the CH(3)1 lesion directly disrupts Parp gene expression. We have therefore renamed the CH(3)1 and CH(3)4 alleles as Parp$^{CH1}$ and Parp$^{CH4}$ respectively.

Figure 6:
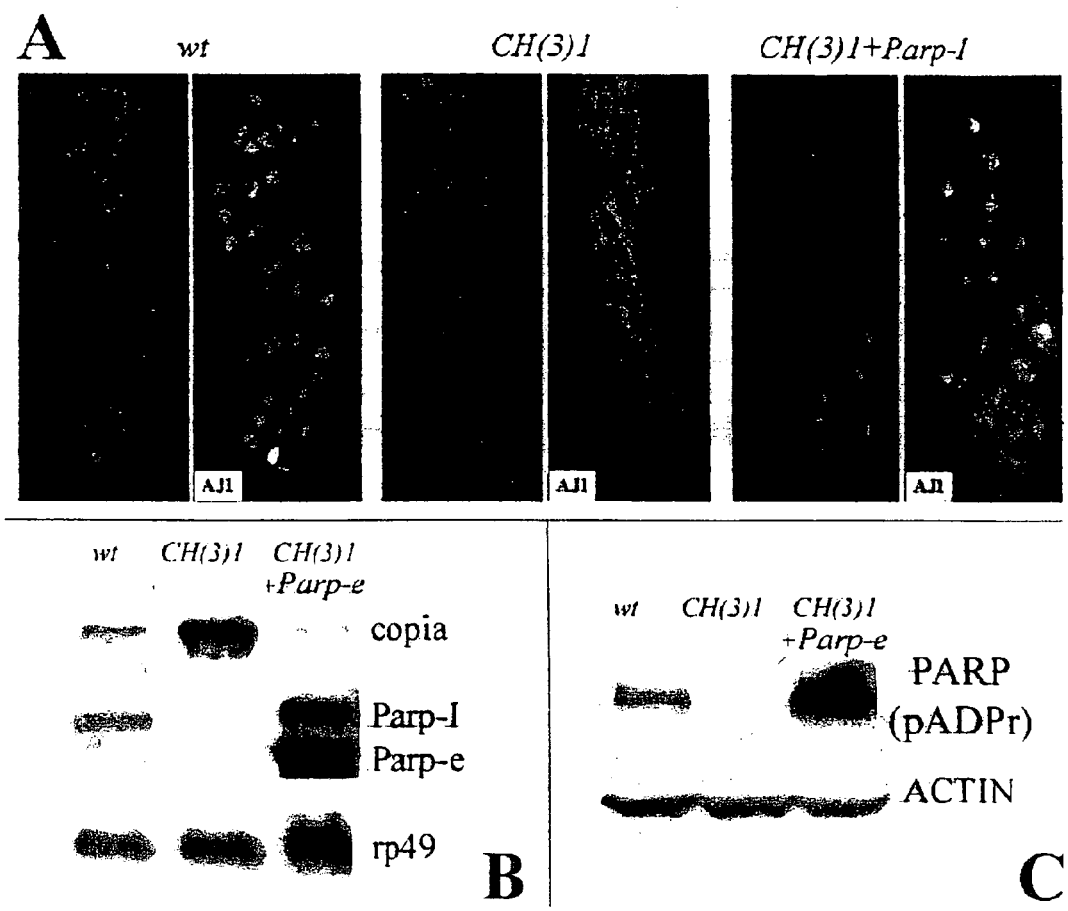
FIGS. 6A-C. Expression of Parp-I or Parp-e cDNA rescues defects in CH(3)1 mutants. (A) Partial restoration of normal nuclear morphology by expression of Parp-I. Immunofluorescent detection of the nucleolar antigen AJ1 (red) and DNA (green) is shown in larval salivary glands of the indicated genotypes. AJ1 staining alone is shown on the right. In CH(3)1 mutants (center), AJ1 is cytoplasmic rather than in nucleoli as in wild type (left). Expression of Parp-I cDNA (right) restores nucleoli and nuclear AJ1 staining in a mosaic manner; note cells at the top of the figure with normal localization, but cells near the bottom still show a mostly cytoplasmic distribution of AJ1 reactivity. (B) A Northern blot of RNA from larvae of the indicated genotypes shows that Parp-e cDNA expression greatly elevates the level of 2.6 kb Parp-e mRNA and also of the 3.2 kb Parp-I mRNA. Note that copia-specific RNA accumulation is greatly reduced in CH(3)1 mutant larvae that express Parp-e cDNA. rp49 hybridization serves as a loading control. (C) A Western blot of proteins isolated from larvae of the same genotypes as in (C), and probed with an antibody specific for poly(ADP-ribosyl) moieties. Expression of Parp-e cDNA in a CH(3)1 homozygous background increases the amount of poly(ADP)-ribose-modified proteins to levels greater than in wild type. As in the wild type, diverse protein areas are affected, the most prominent of which is the size of PARP-I itself (shown). An actin antibody is used as a loading control.

Expressing Parp transcripts dramatically restores the nuclear morphology and the Parp expression of the mutant larvae. Parp-I expression causes a nucleolus to form that can be visualized with the specific antibody AJ1 in many but not all nuclei (FIG. 6A). The mosaic nature of the response, which may result from cell to cell variation in either the production or effects of ectopic PARP-I, is likely to explain the failure of this construct to rescue fully. All nuclei in the Parp-e expressing animals appear wild type in morphology. Surprisingly, larvae rescued by Parp-e contain higher than wild type levels of both the 2.6 kb Parp-e and the 3.2 kb Parp-I mRNA species (FIG. 6B). Thus, the enzymatically inactive PARP-e isoform may rescue CH(3)1 by inducing production of Parp-I mRNA. Consistent with this model, ADP-ribosyl transferase enzymatic activity is also restored, because the amount of poly(ADP-ribose)-containing protein detectable by anti-poly(ADP-ribose)-specific antibody increases to well above wild type levels (FIG. 6C, 117 kd PARP-I band). PARP-e may induce a more physiological pattern of Parp-I expression, leading to fewer deleterious effects than when Parp-I is mis-expressed globally. How expression of an enzymatically inactive protein rescues Parp-I expression and ADP-ribosyl transferase activity is discussed below.

PARP and SIR2 Modify GAL4/UAS Variegation

Figure 7:
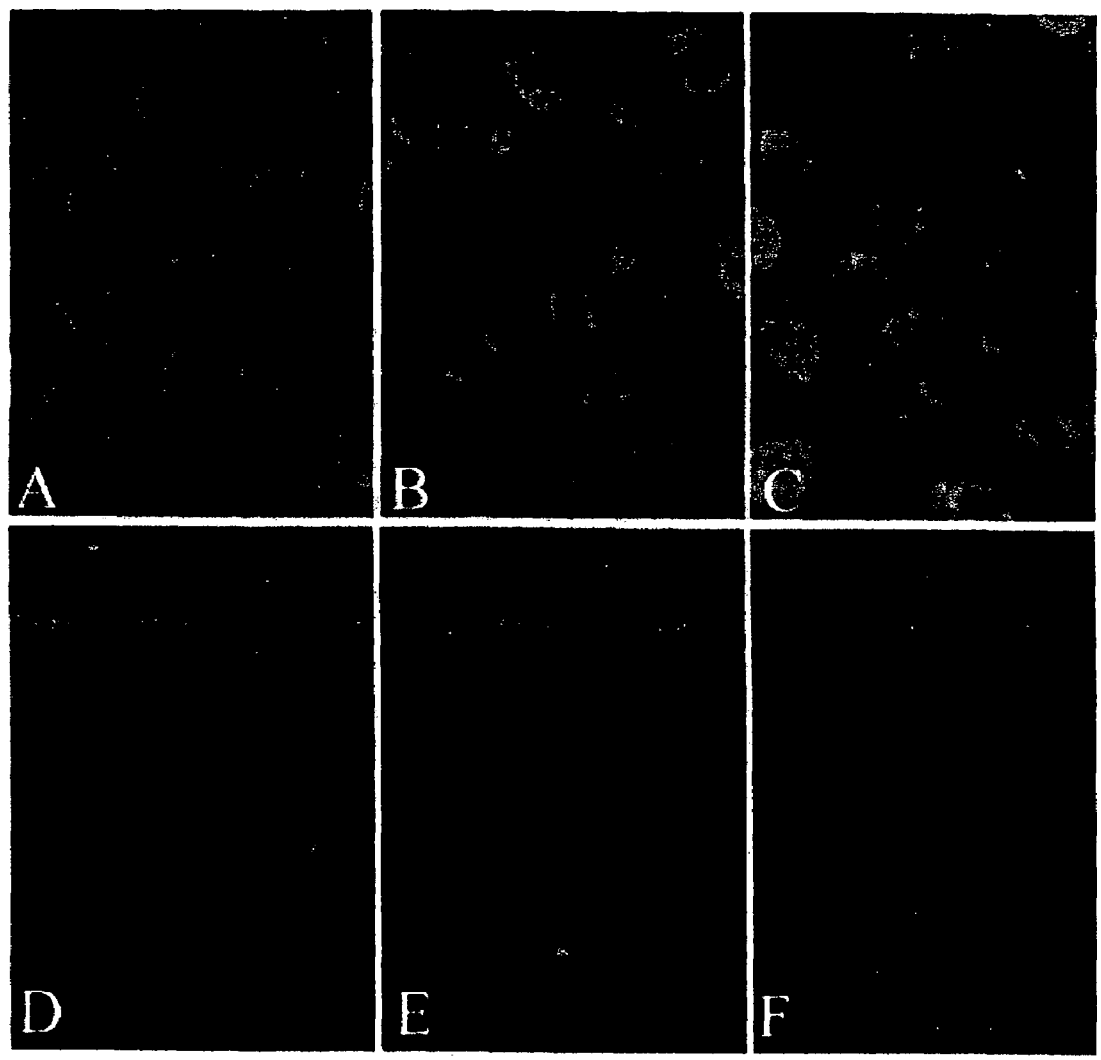

Since the Parp gene is located in heterochromatin and acts on the chromatin structure of repetitive DNA sequences, we investigated whether it functions as an enhancer or suppressor of variegated position effects. Neither Parp$^{CH1}$ nor Parp$^{CH4}$ altered the level of w$^{m4}$ variegation, a standard test for modifiers of classical position-effect variegation (data not shown). However, we did notice that Parp strongly effects the variegated expression commonly exhibited by many UAS/GAL4 constructs (Brand and Perrimon, 1993). For example, in the presence of only one wild type dose of Parp+, the variegation of an epitope-tagged mitochondrial protein (Tim17B-DsRed) driven from a UAS promoter is strongly enhanced (FIGS. 7A-B). At six different tested sites of integration, DsRed expression is virtually silenced in a Parp$^{CH1/+}$ background, while at the seventh site, non-variegated expression becomes variegated. Altering the dose of Sir2 was found to have the opposite effect and dominantly suppress UAS-Tim17B-DsRed variegation (FIG. 7C). Similar reciprocal effects were observed with two other tested constructs, UAS-Parp-1-DsRed (not shown) and UAS-Sir2-DsRed (FIGS. 7D-F), suggesting that the dosage of Parp and Sir2 may affect the expression of UAS/GAL4 constructs generally. PARP and SIR2 levels may alter the chromatin structure of sequences such as those in UAS and GAL4 constructs that are prone to silencing during development.

PARP Regulates Chromatin Structure During Development

PARP is a conserved protein known to play critical roles that help restore and maintain genomic integrity (reviewed by de Murica and Shall, 2000). By identifying lethal Parp mutations, we showed that *Drosophila* Parp also plays an essential role during the lifecycle in the absence of external stresses. Many genes have been identified previously that act in both DNA repair and during development (Baker et al. 1976. *Proc. Natl. Acad. Sci. USA*. 73: 4140-4144; Gatti et al. 1989. *Genes Dev.* 3: 438-53). However, the phenotype of Parp mutants differs from those of other genes in this class, which typically produce third instar larvae deficient in diploid tissue as a result of defects in the mitotic cell cycle.

Our experiments suggest that *Drosophila* Parp plays a special and fundamental role in organizing chromatin on a global scale. Parp mutant cells lack nucleoli and contain unusually nuclease-accessible repetitive sequences. Both the heavy expression of Parp-e and Parp-I in oocytes and early embryos and the early onset of these defects suggest that a major role for PARP occurs as development begins. At fertilization, the zygote genome is quiescent and unregionalized, but during the final cleavage divisions heterochromatin becomes distinguishable from euchromatin, nucleoli form, and specific gene transcription begins. Zygotic PARP activity may be needed to carry out these changes, which are reminiscent of the amphibian "mid-blastula transition." The strong enrichment of epitope-tagged PARP in nucleoli and on heterochromatin is consistent with such a role. When Parp function is limited by a declining maternal pool, chromatin may not regionalize normally, stunting further development.

Our observations argue that the role of Parp is not limited to the initial stages of development, however. Programmed changes in chromatin organization continue after blastoderm formation in concert with cell differentiation (reviewed in Hagstrom et al. 1997. *Curr. Opin. Genet. Dev.* 7: 814-821). The effects of reducing Parp expression later in embryonic development using RNAi, and the influence of Parp dosage on GAL4/UAS variegation, indicate that it also participates in organizing chromatin domains during later embryonic and larval growth. PARP plays a positive role in expressing euchromatic UAS constructs since reduced Parp dosage enhances the variegation of these transgenes. Furthermore, Parp function is likely to be specially required for larval metamorphosis, since up to 50% of mutant larvae were arrested at precisely this stage. Thus, PARP influences both the expression and silencing of particular euchromatic and heterochromatic sequences at diverse times during *Drosophila* development.

PARP may Act by Modifying Chromosomal Proteins

Enzymes that add or remove phosphoryl, acetyl or methyl gbe has been reported to associate with polynucleosomes in vivo (Leduc et al. 1986). We observed a strong reduction in the levels of protein ADP-ribosylation in PARP mutants. Many of the modified proteins detectable with antibodies that recognize protein-ADP(ribosyl) groups are located along chromosomes, and are particularly enriched in nucleoli and in the heterochromatic chromocenter, regions strongly affected by Parp mutations. These observations support the idea that PARP acts on *Drosophila* chromatin by ADP-ribosylating chromatin proteins.

PARP-e Autoregulates the Activity of a Complex Parp Gene Located Within Heterochromatin Our structural characterization of the Parp gene reveals that both the gene itself and its surrounding chromosomal region are complex. The Parp locus is localized in 3R heterochromatin near band h55, where it spans at least 150 kb. At least two promoters are utilized and the upstream promoter, Pm2, produces a transcript encoding a novel protein isoform, PARP-e, primarily during oogenesis and early larval development. Four other genes reside nearby and are transcribed in the same direction. In contrast, most of the DNA located outside gene exons consists of diverse transposable elements that are oriented opposite to the genes, perhaps as a result of selection to minimize the disruptive effects of transposon-encoded transcription and splicing signals. Much remains to be learned about the number, structure, regulation and evolution of heterochromatic genes (reviewed by Weiler et al. 1995. *Annu. Rev. Genet.* 29: 577-605; Cook et al. 1994. *Proc. Natl. Acad. Sci. USA*. 91: 5219-5221). The Parp region may now serve as a valuable model for detailed studies of these issues.

Our experiments suggest that Parp itself is subject to novel regulatory mechanisms. $Parp^{CH1}$ likely disrupts Parp-e transcription from Pm2, but homozygotes also have greatly reduced levels of Parp-I mRNA and of PARP activity, despite the fact that Pm1 is located at least 75 kb downstream from the $Parp^{CH1}$ insertion site. Thus, Parp-e production appears to be essential for transcription of Parp-I from Pm1. It is difficult to rule out the existence of additional promoters or splice forms of PARP transcripts. However, the fact that expression of a cDNA encoding PARP-e rescues lethality, Parp-I mRNA production and ADP ribosyl-transferase activity argues strongly that PARP-e autoregulates Parp transcription. Indeed, Parp-e expression may be rate-limiting for Parp-I transcription because overproduced Parp-e from the rescue construct was associated with elevated levels of Parp-I mRNA (FIG. 6C).

There are two basic ways in which Parp-e might control Parp-I transcription. PARP-e may simply function as a factor that activates transcription from Pm1. Alternatively, it may function by a novel mechanism related to its action on heterochromatin. The Pm1 promoter and surrounding sequences may need to acquire a compact, heterochromatic chromatin state for activity. Zygotic PARP-e produced near the onset of development would facilitate heterochromatin formation, thereby activating Pm1 and Parp-I production. Simultaneously, this chromatin transition might shut off or limit Parp-e production from Pm2. Such a feedback switch would link PARP production to the chromatin state and might represent a mechanism utilized by other heterochromatic genes. Two other such genes were shown recently to require the heterochromatin-specific HP-1 protein to be efficiently expressed (Lu et al. 2000. *Genetics*. 155: 699-708).

PARP may Remodel and Maintain Chromatin Domains

Previous studies of the role played by PARP during DNA repair have led to a model of how it acts on chromatin (reviewed in Zeigler et al. 2001). Following DNA damage, inactive PARP-I protein located near the damaged region binds to DNA breaks, activating the catalytic site, and begins to transfer ADP-ribose groups to the chromatin proteins located in the immediate vicinity and to the PARP automodification domain. The modified proteins are released from the DNA, allowing repair enzymes to access the damaged region. When repair is complete, the ADP-ribosyl groups are removed by a specific glycosylase and the disrupted chromatin reassembles. During this time, automodified PARP may serve as a local storage site for the dissociated chromatin proteins preventing them from diffusing away and mixing with general pools (Althaus, 1992). The local nature of the disruption may help to ensure that repair does not inadvertently lead to alterations in the pre-existing state of chromatin programming.

We propose that the role played by PARP in DNA repair, as described above, represents just one instance of a general function PARP carries out to re-program chromatin at multiple points during the life cycle. Inactive PARP molecules located in many chromosome regions may be subject to activation by particular developmental and environmental stimuli in addition to DNA damage. Following such stimulation, activated PARP would catalyze the dissociation of chromosomal proteins in the affected domain. Introducing new or differentially modified chromosomal proteins to the affected site in conjunction with PARP activation would cause the local chromatin state to be specifically altered when ADP-ribosyl residues are subsequently cleaved and the dissociated proteins re-assembled. Such a mechanism would allow chromatin re-modeling to be precisely limited to particular chromosome regions by spatially controlling the sites of PARP activation and protein delivery. It might also explain many previous observations concerning the transcriptional role of PARP and its interaction with transcription factors.

Our results suggest that PARP acts to maintain certain chromatin domains as well as to remodel them. For example, copia sequences in animals that had already formed heterochromatin became nuclease sensitive when PARP levels were gradually reduced in developing embryos using RNAi. Even when enzymatically inactive, PARP molecules remain associated with many chromosome regions and may play essential structural roles. Disruption of these roles may be responsible for some of the effects caused by loss of the enzymatically inactive PARP-e isoform, and for some of the deleterious effects of PARP-I over-expression. Our findings emphasize the importance of learning more about the properties of PARP molecules within specific chromosome regions and how they change during chromatin re-programming. Finally, they suggest ways in which manipulating PARP molecules might allow chromatin re-programming to be experimentally controlled.

Figure 8:
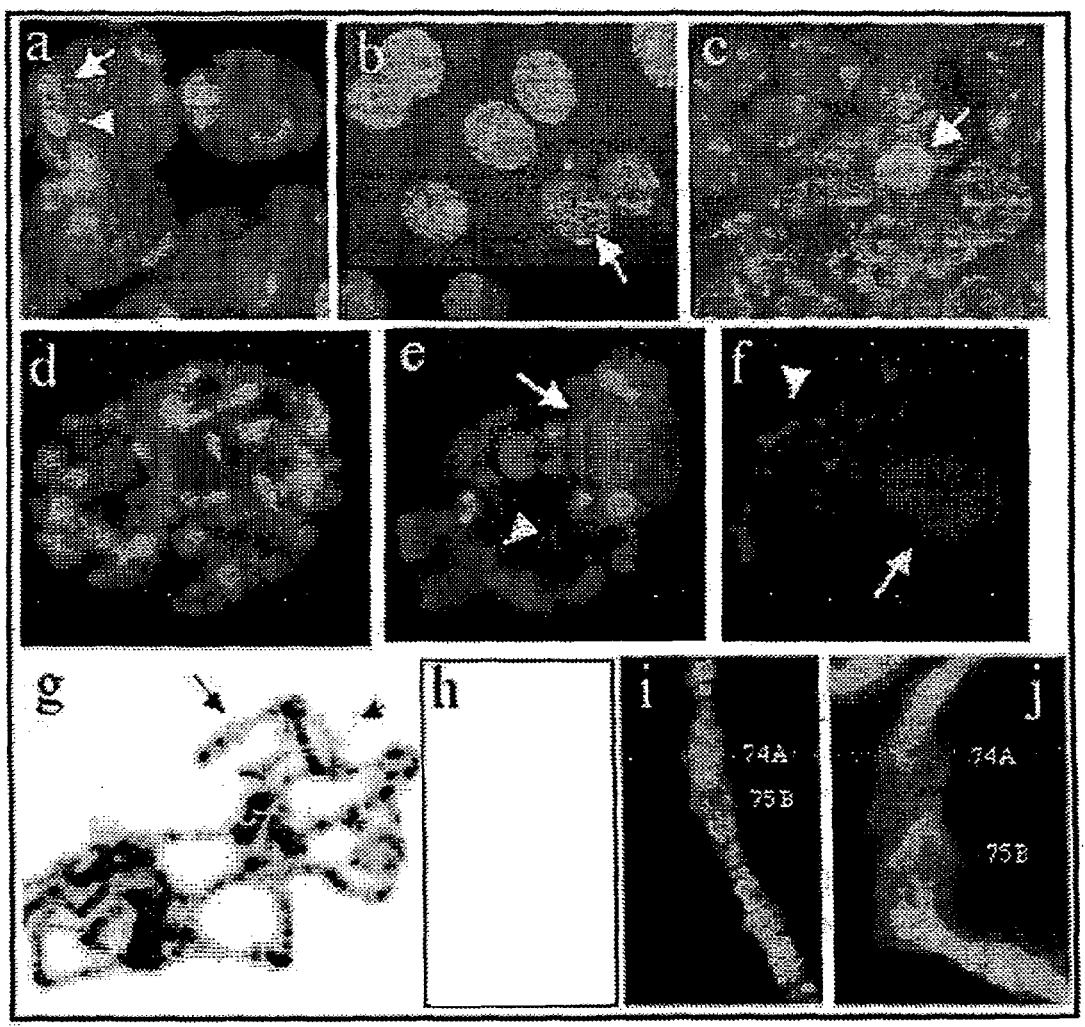

PARP is Distributed Widely Along Chromosome but ADP-Ribose Modified Proteins are Enriched in Polytene Chromosome Puffs We used flies bearing PARP-DsRed- or PARP-EGFP-transgenes (Tulin et al. 2002) to further investigate the distribution of PARP protein on chromosomes (FIG. 8). PARP associates with the chromatin of diploid cells although at lower levels than in nucleoli (FIG. 5A). The incorporation pattern of biotinylated-NAD into protein could be visualized in polytene larval cells, and was very similar to the pattern of PARP-DsRed (FIGS. 8D, 8E). This suggests that PARP molecules with a low level of enzymatic activity coat chromosomes. In contrast, the pattern of staining with an antibody that specifically recognizes large clusters of protein-bound NAD-ribose moieties is discontinuous and strongly enriched at a limited number of euchromatic sites (FIG. 8F). When chromosomes were squashed under appropriate conditions (Examples), many of these sites could be seen to correspond to polytene chromosome puffs (FIG. 8G).

Interestingly, we observed that high levels of modified proteins were not observed prior to puffing (FIGS. 8H, 8I) and that the actual level of PARP protein in puffs was similar to other regions (FIG. 8J). These observations suggested that PARP protein becomes strongly activated within puffs and modifies local proteins by adding ADP-ribose moieties. In the course of these studies, we noticed that while the average level of PARP expression is greatly reduced in the Parp$^{CH1}$ mutant animals (Tulin et al 2002) a low level of variegated expression continues in this P-element induced mutation, as scattered nuclei still contained nucleoli (FIG. 8C, arrow).

Heat Shock Induced Expression of hsp70 is Greatly Reduced in PARP-larvae

Figure 9:
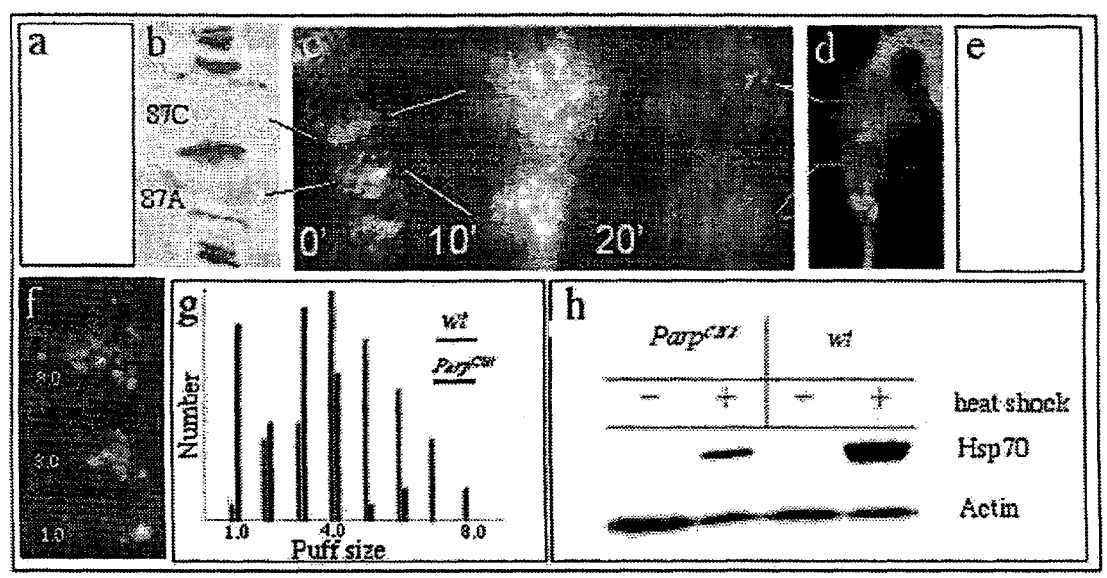
Figure 10:
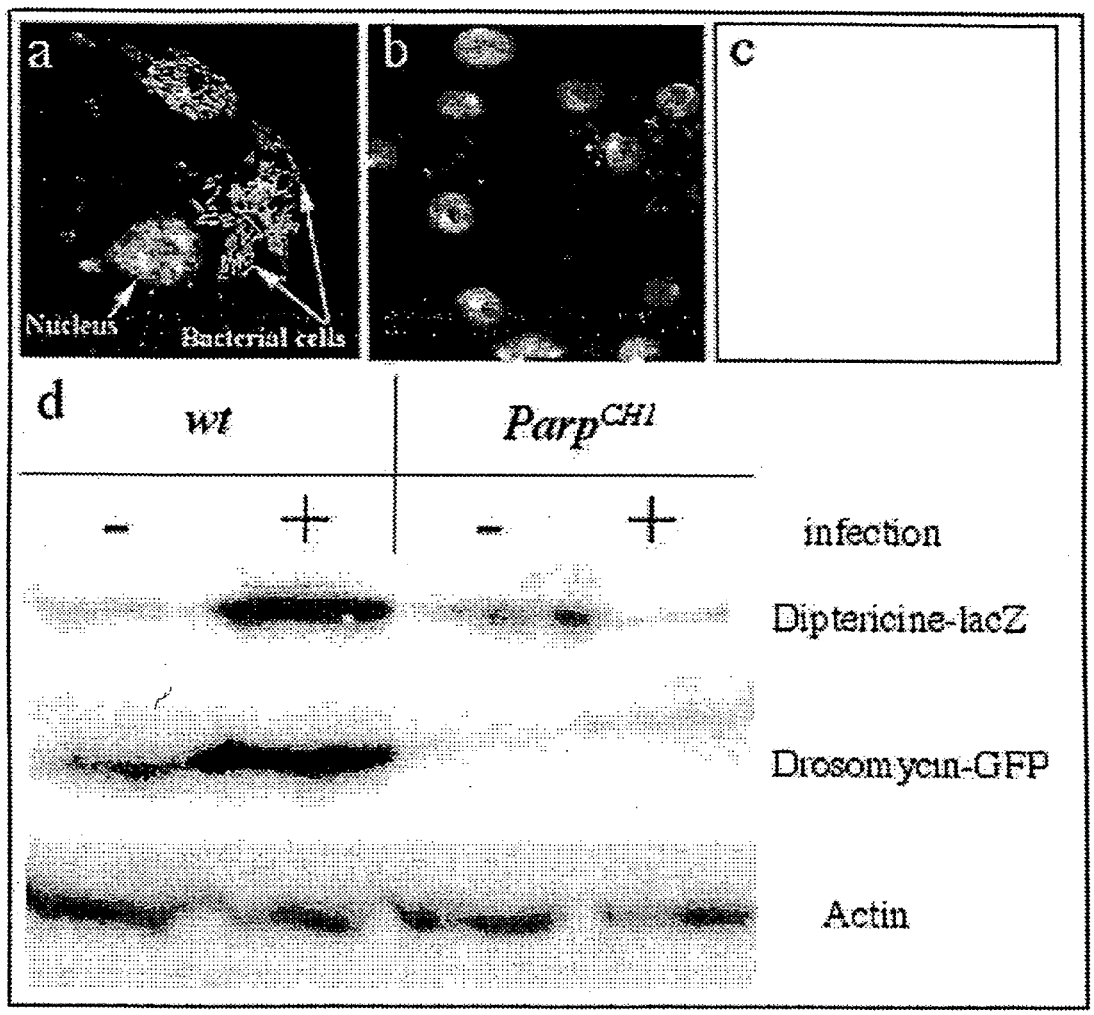

A short heat shock strongly induces puffing at a small number of specific loci containing stress response genes (reviewed in Lindquist S. 1986. Ann. Rev. Biochem. 55:1151-91) including the 87A and 87C puffs containing clustered genes encoding the Hsp70 chaperone (FIGS. 9A, 9B). Prior to heat shock, only normal background amounts of poly(ADP-ribose)-modified proteins are present at the 87A and 87C loci (FIG. 9C, 0 minutes). Within just 10 minutes after shifting to 37° C., ADP-ribose modified proteins accumulate throughout the newly forming puffs (FIG. 2C, 10 minutes). The amount of these modified proteins begins to fall sometime thereafter, and the puff itself will soon regress (Ashburner. 1970. Adv. Ins. Phys. 7, 1-95). These observations raise the question of whether the increase in protein ADP-ribosylation is a cause or effect of the process of heat shock induced puffing.

To determine if the Parp gene encodes the enzyme responsible for this increase, and if it is required for puffing, we wanted to determine if heat shock induced puffs formed normally in Parp mutant larvae. Unfortunately, Parp-defective animals die as second instar larvae, before salivary gland polytene chromosomes grow large enough to recognize banding patterns or specific puffs. However, the small puffs that form in wild type 12 chromosomes can be visualized using anti-RNA polymerase antibodies, which recognize the large accumulation of this enzyme at puff loci (FIGS. 9F, G). Moreover, it was possible to recognize the 87A 87C "double" puff specifically. These studies showed that the average size of the 87A and 87C puffs was reduced at least 3-fold in Parp$^{CH1}$ larvae. We suspected those cells within Parp$^{CH1}$ larvae that still were able to form small heat shock puffs, might retain a small amount of maternal or leaky Parp expression. Consequently, we double stained for puffs and for AJ1 nucleolar antigen. Cells that formed substantial puffs (3.0-4.0) still had nucleoli, whereas cells with very small puffs showed only cytoplasmic staining (data not shown). We concluded that PARP was required to form normal heat shock puffs, most likely by modifying proteins at the puff site. A similar blockage of puff formation was observed in third instar larvae within 30 minutes of injecting the specific PARP inhibitor, 3-aminobenzamide.

If the chromatin alterations that give rise to a puff are important for gene activity, then Hsp70 production should be reduced following heat shock in Parp$^{CH}$ compared to wild type larvae. Western blots showed that the amount of Hsp70 protein recognized by specific antibodies was reduced 5-10-fold in the mutant. Thus, Parp is needed to form normal heat shock puffs and to express normal levels of puff encoded proteins.

PARP is Required for Anti-bacterial Immunity

Heat shock genes all utilize a common transcription factor called HSF (Wu, Methods Enzymol. 170: 269 (1989)). Mice deficient in Parp1 display immune defects and are unable to normally induce immune responses that require the NF-κB family of transcription factors (see deMurica et al. 2000). A major mechanism of resistance to extracellular microbes in insects such as Drosophila is provided by innate immunity genes (reviewed by Hoffman et al. 2002. Nat Immunol. 3: 121-6). These genes encode antimicrobial peptides and their rapid induction following infection is controlled by NFκB-related transcription factors (Han et al. 1999. J Biol. Chem. 274: 21355-61).

Consequently, to look for other gene families that might require PARP, we tested the resistance of wild type and Parp$^{CH1}$ larvae to the injection of approximately $2 \times 10^4$ E. coli bacteria injected into their haemolymph. More than 95% of wild type but less than 7% of Parp$^{CH1}$ larvae survive such a challenge. Even normal, unchallenged mutant animals frequently acquired spontaneous intracellular bacterial infections (FIG. 10A). In tissues showing variegated Parp activity we noticed that bacteria were found preferentially in cells that lacked Parp activity (FIG. 10B).

We compared the ability of wild type animals to induce two innate immunity genes, Diptericine and Drosomycin, using Diptericine-lacZ and Drosomycin-GFP reporter genes that can be recognized by specific anti-sera (FIG. 10D). Both genes were strongly induced in wild types following bacterial challenge, but under the same conditions their levels increased little if at all in Parp$^{CH1}$ animals. To determine if Parp might be required at the level of chromatin, we injected bacteria along with biotinylated-NAD into 13 larvae and analyzed polytene chromsomes using avidin staining three hours later (FIG. 10C). Evidence that NAD was heavily incorporated at one or more specific loci was observed, suggesting that some loci do form puffs in response to bacterial infection.

PARP may Facilitate Diverse Types of Chromatin Remodeling

Previously, we reported that PARP is required to form and/or maintain normal heterochromatin, to repress copia retrotransposon transcription, and to form and/or maintain nucleoli (Tulin et al. 2002). The experiments reported here extend the chromosomal processes that require Parp function to include the induction of specific genes—those encoding Drosophila heat shock proteins, and at least some innate immunity genes. PARP's proposed mechanism of action during DNA repair suggests a model (FIG. 11) that can unify many or all of these functions. Canonical PARP proteins such as mouse PARP1 are thought to act as a reversible chromatin removal device at sites of DNA damage. First, PARP senses lesions and activates its catalytic domain, causing it to modify nucleosomal histones, transcription factors and other chromosomal proteins so that they dissociate from DNA. At the same time, activated PARP turns off its own catalytic activity by automodification. While present, the ADP-ribosyl chains may bind the removed chromatin proteins and tether them near their original location. Following repair of the lesions and removal of poly(ADP)-ribose groups by glycosylase, the chromatin proteins are freed and reassemble onto the DNA.

For a similar model to explain developmentally or environmentally controlled chromatin re-modeling, this general sequence of events must change in two ways. First, signals other than DNA lesions must be able to activate PARP. PARP interacts specifically with many other proteins, some of which may activate the COOH terminal catalytic domain. PARP contains potential target sites for casein kinase 2, and may itself be subject to covalent modifications that might facilitate activation. Whatever the mechanism, it would be important that it take place only with appropriate chromosome domains and at the appropriate time. This suggests that specific transcription factors with which PARP interacts are strong candidates as co-activators of PARP activity.

The second requirement is that new co-factors or modifications occur while the chromatin proteins have been removed so that they reassemble into a different state than before. Many sites of PARP activation, such as nucleoli and puff loci, may reassemble in their original state, like sites following DNA repair. However, in certain cases, as during heterochromatin formation, or some hormonally induced puffs, a new chromatin state may arise. For this end, new chromatin proteins may be added, and existing proteins may be modified while dissociated and bound to ADP-ribose polymers. The disassembly of protein complexes is likely to facilitate re-assembly into new patterns. The same environmental or developmental signals that activate PARP might induce the relevant new proteins and modifying activities to program the outcome.

Puffs may be a Visual Manifestation of PARP-mediated Chromatin Remodeling

The direct visualization of the chromatin changes during puffing is one of the strongest arguments for the model of FIG. 11. However, the mechanism and function of these dramatic chromatin alterations have remained enigmatic. While the promoter strength and length of the underlying transcription unit can affect the size of puffs induced by heat shock transgenes (Simon et al. 1985. *Cell.* 40: 805-17), puffing and transcription are separable (Simon et al. 1985. *Chromosoma* 93:26-30); Meyerowitz et al. 1988). The chromatin surrounding the hsp70 genes is profoundly altered by puffing. Nuclosomes lose their regular association with DNA (Cartwright et al. 1986. *Mol. Cell. Biol.* 6, 779-791) and the DNA becomes as extended as naked DNA (Simon et al., 1985). Our experiments provide a plausible mechanism for these extensive changes. The question of why genes such as hsp70 and ecdysone response genes, but not many other highly transcribed genes, undergo these major chromatin changes upon activation remains less clear. Loosening and removal of nucleosomes may allow an increased polymerase elongation rate and hence higher rates of protein production. If so, then puff loci must have evolved transcriptional mechanisms that are resistant to disruption by PARP activation. During repair Poly(ADP-ribose) addition is thought to inhibit transcription. Poly(ADP-ribose) addition to TATA binding protein (TBP) and to transcription factors such as YY1, p53 (Mendoza-Alvarez et al. 2001) and CREB blocks their ability to bind DNA in vitro. However, TBP and transcription factors that are already bound to DNA resist modification and are not released (Oei et al. 1998). The preformed transcription complexes found on heat shock genes (reviewed in Lis et al. 1995. In: Elgin, S. C. R. (Ed.), Chromatin Structure and Gene Expression. IRL Press, Oxford, pp. 71-88) might therefore provide an initial resistance to inhibition. Large amounts of poly(ADP-ribose) polymer might have functions completely separate from transcriptional activation, such as providing temporary storage sites for chaperone complexes containing nuclear proteins. Regardless of the exact mechanisms, our findings indicate that PARP activation does not inevitably lead to the dissociation of all chromatin proteins, and that high levels of PARP activation are compatible with some ongoing chromosomal functions.

Parp function is likely to be required to form puffs generally, and not just for heat shock puffs we studied. All the puffs we observed had high levels of ADP-ribose modified proteins, including the ecdysone induced puffs such as 74A and 75B (FIG. 9). We previously reported that Parp$^{CH1}$ mutant larvae frequently arrest development precisely at the moult between the second (12) and third (13) larval instars (Tulin et al. 2002). Such molts are induced by a rise in the titer of juvenile hormone, and induce a series ecdysone response genes (Thummel 2000). Our results suggest that the developmental arrest of Parp larvae results from a failure to express ecdysone response genes.

Parp may act by other mechanisms that do not involve chromatin removal

In some instances, PARP has been proposed to act directly as a transcription factor or chromatin modulator. In mammals, NF-κB and PARP-1 form dimers (Hassa et al. 1999; Chang et al. 2001. *J Biol. Chem.* 276: 47664-70). These complexes may activate NF-κB dependent gene transcription, a function requiring neither PARP DNA binding nor catalytic activity (Hassa et al. 2001. *J Biol. Chem.* 276:

45588-97). Alternatively, the complex may be inactive, but PARP automodification would disrupt its association with NF-κB, releasing NF-κB for activation (Chang et al. 2001). The nature of the PARP1 requirement in vivo has not been resolved, however. Parp-deficient *Drosophila* were found to have also have defects in immune function and in NF-κB-dependent gene transcription. Further study immune gene induction in normal and mutant flies is likely to reveal if Parp is required at the level of transcriptional initiation or chromatin structure.

PARP forms stable protein-protein complexes with numerous other chromosomal proteins. These interactions might in some cases modulate chromatin structure by mechanisms that do not require catalytic activity. For example, PARP associates with the mammalian YY1 transcription factor. In *Drosophila*, the YY1 homologue Pleiohomeotic is likely determinant for repression complexes mediated by the Polycomb protein.

There are additional reasons to believe that not all actions mediated by PARP take place via chromatin changes. Both mammalian cells and *Drosophila* produce multiple PARP isoforms as well as related proteins sharing some protein domains. A number of these proteins contain the PARP catalytic domain consensus without the DNA binding or automodification domains In addition, molecules such as PARP-e (Tulin et al. 2002), lack the catalytic domain, and PARP-e is required for the production of all Parp isoforms. These PARP-e related molecules may act directly as transcription factors or chromatin proteins. Thus, PARP-e related proteins are abundant and versatile proteins that likely play diverse roles.

Use of Parp for Gene Re-programming

These studies suggest that PARP could be used to experimentally reprogram chromatin, a capability that would have many useful applications. For example, a specific gene could be activated in a differentiated cell type where it is normally inactive and in a suppressed chromatin state. First, endogenous chromosomal PARP molecules would be activated at the site of such a gene by engineering local DNA damage, or through the binding of PARP-activating factors that act at normal puff sites. The activated PARP molecules will then modify local chromatin proteins, including histones, causing some to dissociate and the chromatin structure to loosen. If the transcription factors needed for gene transcription are present or are simultaneously provided, the desired gene should begin to be transcribed. In some cases this may be sufficient for the desired effect, however, it would likely be possible by further actions to make the reprogrammed gene remain active. If appropriate chromatin and chromatin-modifying proteins are expressed prior to the downregulation of PARP activity, the chromatin surrounding the gene is likely to re-assemble in an active state. A better understanding of the role of PARP in normal chromatin re-programming will likely facilitate the development of such methods.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. An isolated nucleic acid molecule encoding a poly (ADP-ribose) polymerase (PARP) comprising SEQ ID NO: 2.

2. The isolated nucleic acid molecule of claim 1, wherein the nucleic acid molecule comprises SEQ ID NO: 1.

3. The isolated nucleic acid molecule of claim 2, wherein the nucleic acid molecule consists of SEQ ID NO: 1.

4. An isolated nucleic acid comprising SEQ ID NO: 10.

* * * * *

SEQUENCE LISTING

<160> NUMBER OF SEQ ID NOS: 10

<210> SEQ ID NO 1
<211> LENGTH: 2427
<212> TYPE: DNA
<213> ORGANISM: Drosophila melanogaster
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: CDS
<222> LOCATION: (282)..(2123)
<223> OTHER INFORMATION: PARP-e cDNA sequence

<400> SEQUENCE: 1

```
cctcatcatg ntgtgtagac gttatagctt cttttcctat tttggtcacc gggctgagta      60
gcgctactct taatacgttt aattgttaat tttaatttta atttttcatt gcccacattt     120
ttgaaagtct atcgaaatat tttcaaagtt attttcccac ggtgccattt taactgtctt     180
gattttgtgt ataccggcct ggttttcaag cctttggaaa aactgatcta aatcgagatt     240
tccaatagga attttgtcta cattgatatc tggtatgtaa t atg gat att gaa tta     296
                                             Met Asp Ile Glu Leu
                                               1               5 cct tat ctt gct gag tat gca aga act gga cga gcc act tgc aaa gga     344
Pro Tyr Leu Ala Glu Tyr Ala Arg Thr Gly Arg Ala Thr Cys Lys Gly
             10                  15                  20 tgt aaa agt act ata tct aaa gat act ctt cgg att gct gtc atg gtt     392
Cys Lys Ser Thr Ile Ser Lys Asp Thr Leu Arg Ile Ala Val Met Val
         25                  30                  35
```

```
                                                   -continued caa tct gca ttt cat gat gcc aaa gtt ccg aat tgg ttt cat aaa acc        440
Gln Ser Ala Phe His Asp Ala Lys Val Pro Asn Trp Phe His Lys Thr
         40                  45                  50 tgc ttt ttt aaa aac cag cgt ccc agc tca gta gga gac ata caa aac        488
Cys Phe Phe Lys Asn Gln Arg Pro Ser Ser Val Gly Asp Ile Gln Asn
 55                  60                  65 att gga aat ctc cga ttt gcc gat caa aag gaa tta acg gat ctt gtg        536
Ile Gly Asn Leu Arg Phe Ala Asp Gln Lys Glu Leu Thr Asp Leu Val
 70                  75                  80                  85 gaa aat ata caa gaa gtt ata agc gca caa tta gga aaa aag cga tcg        584
Glu Asn Ile Gln Glu Val Ile Ser Ala Gln Leu Gly Lys Lys Arg Ser
                 90                  95                 100 aag gct ttt aac tta gca tta aaa gac ttt ggg att gaa tat gca aaa        632
Lys Ala Phe Asn Leu Ala Leu Lys Asp Phe Gly Ile Glu Tyr Ala Lys
                105                 110                 115 tct agt cga tcg acg tgt cgt gga tgt gaa caa aaa ata aac aag gat        680
Ser Ser Arg Ser Thr Cys Arg Gly Cys Glu Gln Lys Ile Asn Lys Asp
        120                 125                 130 cta gtt cgc tta cgt aaa act gtt tat gat act gaa gtt ggt atg aag        728
Leu Val Arg Leu Arg Lys Thr Val Tyr Asp Thr Glu Val Gly Met Lys
135                 140                 145 tac gga ggc caa cct ttg tgg cat cat ttg gaa tgc ttc gcc caa ttg        776
Tyr Gly Gly Gln Pro Leu Trp His His Leu Glu Cys Phe Ala Gln Leu
150                 155                 160                 165 cgc tct gag ctt ggc tgg ttt gcg tca ggt gaa gat atg cca gga ttt        824
Arg Ser Glu Leu Gly Trp Phe Ala Ser Gly Glu Asp Met Pro Gly Phe
                170                 175                 180 cag agc tta gca gat gat gat caa gcg aaa gtt aaa aac gcc ata cca        872
Gln Ser Leu Ala Asp Asp Asp Gln Ala Lys Val Lys Asn Ala Ile Pro
                185                 190                 195 cca ata aaa tct gaa gaa cta cca gat aca aaa aga gct aag atg gaa        920
Pro Ile Lys Ser Glu Glu Leu Pro Asp Thr Lys Arg Ala Lys Met Glu
        200                 205                 210 tta tca gat aca aat gaa gaa gga gaa aag aaa caa cgc tta aaa gat        968
Leu Ser Asp Thr Asn Glu Glu Gly Glu Lys Lys Gln Arg Leu Lys Asp
215                 220                 225 caa aat gat gcc tac ttc agg ttt cgc gat gac att aaa aat aaa atg       1016
Gln Asn Asp Ala Tyr Phe Arg Phe Arg Asp Asp Ile Lys Asn Lys Met
230                 235                 240                 245 aag aag aaa gac att gat ata ctt ctt aag ttt aat aat caa caa cct       1064
Lys Lys Lys Asp Ile Asp Ile Leu Leu Lys Phe Asn Asn Gln Gln Pro
                250                 255                 260 gta act ggt gac aca gaa aag tta ttt gat caa act gcc gat tta ctg       1112
Val Thr Gly Asp Thr Glu Lys Leu Phe Asp Gln Thr Ala Asp Leu Leu
                265                 270                 275 aca ttc gga gct att gaa tca tgt tct gaa tgc aac agc tgt cag ttt       1160
Thr Phe Gly Ala Ile Glu Ser Cys Ser Glu Cys Asn Ser Cys Gln Phe
        280                 285                 290 att gtt aat aaa tct gga tat ata tgt aat gga aat cat tct gag tgg       1208
Ile Val Asn Lys Ser Gly Tyr Ile Cys Asn Gly Asn His Ser Glu Trp
295                 300                 305 acc aaa tgt aac aag ctg cta aaa gag cca aca aga tcg gca tgc ata       1256
Thr Lys Cys Asn Lys Leu Leu Lys Glu Pro Thr Arg Ser Ala Cys Ile
310                 315                 320                 325 gtg cca aaa gaa ctt aaa gca tta tat aat ttt ttg aat acc gtg aaa       1304
Val Pro Lys Glu Leu Lys Ala Leu Tyr Asn Phe Leu Asn Thr Val Lys
                330                 335                 340 gaa att cca tct aca cgg atc ttt aat aac ttt cct ccc aat aaa agt       1352
Glu Ile Pro Ser Thr Arg Ile Phe Asn Asn Phe Pro Pro Asn Lys Ser
```

|   |   |
|---|---|
| acc ttt tct aga agt ctt ttg aaa acg aat aaa aac aat gat gtt ttg<br>Thr Phe Ser Arg Ser Leu Leu Lys Thr Asn Lys Asn Asn Asp Val Leu<br>            360                        365                        370 | 1400 |
| gtt agg cca aca ata cct cgt ata agt ccg cca tta tac aat tta aag<br>Val Arg Pro Thr Ile Pro Arg Ile Ser Pro Pro Leu Tyr Asn Leu Lys<br>375                        380                        385 | 1448 |
| ttt tca att ata ggc tta aag aac cag cat aaa gag cta aga aag cga<br>Phe Ser Ile Ile Gly Leu Lys Asn Gln His Lys Glu Leu Arg Lys Arg<br>390                        395                        400                        405 | 1496 |
| ata gaa aat ttg ggc ggt aaa ttt gaa gtt aaa ata tcg gaa aac acg<br>Ile Glu Asn Leu Gly Gly Lys Phe Glu Val Lys Ile Ser Glu Asn Thr<br>                      410                        415                        420 | 1544 |
| ata gca ata ata tca aca gaa tta gaa ata caa aaa aaa tcc acc cgt<br>Ile Ala Ile Ile Ser Thr Glu Leu Glu Ile Gln Lys Lys Ser Thr Arg<br>425                        430                        435 | 1592 |
| atg aag ttt gca gaa gag ctc gga att cat att gtg ccc att gaa ttt<br>Met Lys Phe Ala Glu Glu Leu Gly Ile His Ile Val Pro Ile Glu Phe<br>                      440                        445                        450 | 1640 |
| tta gat ttt gtt gaa gcc gat aca gaa gga gct att aaa tat ata aat<br>Leu Asp Phe Val Glu Ala Asp Thr Glu Gly Ala Ile Lys Tyr Ile Asn<br>455                        460                        465 | 1688 |
| agc aca tgt att tgt agt tgg gga aca gat cca aaa tcc aga att cca<br>Ser Thr Cys Ile Cys Ser Trp Gly Thr Asp Pro Lys Ser Arg Ile Pro<br>470                        475                        480                        485 | 1736 |
| aag gaa aca aca aaa agt tta aat tcg aac agt ata tat aca aaa tcc<br>Lys Glu Thr Thr Lys Ser Leu Asn Ser Asn Ser Ile Tyr Thr Lys Ser<br>                      490                        495                        500 | 1784 |
| atg cca gta tca cgg aca ttt aaa gta aaa gat ggc cta gct gtt gat<br>Met Pro Val Ser Arg Thr Phe Lys Val Lys Asp Gly Leu Ala Val Asp<br>            505                        510                        515 | 1832 |
| ccg gac agt ggg ctc gag gac atc gcc cat gtt tac gtg gac agt aac<br>Pro Asp Ser Gly Leu Glu Asp Ile Ala His Val Tyr Val Asp Ser Asn<br>        520                        525                        530 | 1880 |
| aat aaa tac agt gtt gtt ctt ggc tta act gac att cag aga aat aag<br>Asn Lys Tyr Ser Val Val Leu Gly Leu Thr Asp Ile Gln Arg Asn Lys<br>535                        540                        545 | 1928 |
| aac tcc tac tac aaa gtt cag ctt tta aaa gcg gat aaa aag gag aaa<br>Asn Ser Tyr Tyr Lys Val Gln Leu Leu Lys Ala Asp Lys Lys Glu Lys<br>550                        555                        560                        565 | 1976 |
| tat tgg att ttt cgt tca tgg ggt cga att gga aca aat att gga aac<br>Tyr Trp Ile Phe Arg Ser Trp Gly Arg Ile Gly Thr Asn Ile Gly Asn<br>                      570                        575                        580 | 2024 |
| tca aaa ctt gaa gag ttc gac acg agc gag tct gca aaa aga aat ttt<br>Ser Lys Leu Glu Glu Phe Asp Thr Ser Glu Ser Ala Lys Arg Asn Phe<br>585                        590                        595 | 2072 |
| aaa gaa ata tat gca gat aaa act gga atg cac ttc agc gaa ata cat<br>Lys Glu Ile Tyr Ala Asp Lys Thr Gly Met His Phe Ser Glu Ile His<br>                      600                        605                        610 | 2120 |
| taa taaactatca aataataaac atagttgttt cggtcgtggt cgcaccatgc | 2173 |
| cagatcctac taagagctat ataagaagtg atggggttga aattccttac ggagaaacca | 2233 |
| ttactgacga acatttaaag tcatcgttat tatataacga gtatatagta tatgatgttg | 2293 |
| cgcaggtcaa tattcaatat ttgtttcgta tggaattcaa gtattcttat taaatgcctt | 2353 |
| aaattatatt gagtgatatt gatattaata aattggaatt attttaaaaa attaaaaaaa | 2413 |
| aaaaaaaaaa aaaa | 2427 |

-continued

```
<210> SEQ ID NO 2
<211> LENGTH: 613
<212> TYPE: PRT
<213> ORGANISM: Drosophila melanogaster

<400> SEQUENCE: 2

Met Asp Ile Glu Leu Pro Tyr Leu Ala Glu Tyr Ala Arg Thr Gly Arg
1               5                   10                  15

Ala Thr Cys Lys Gly Cys Lys Ser Thr Ile Ser Lys Asp Thr Leu Arg
            20                  25                  30

Ile Ala Val Met Val Gln Ser Ala Phe His Asp Ala Lys Val Pro Asn
        35                  40                  45

Trp Phe His Lys Thr Cys Phe Phe Lys Asn Gln Arg Pro Ser Ser Val
    50                  55                  60

Gly Asp Ile Gln Asn Ile Gly Asn Leu Arg Phe Ala Asp Gln Lys Glu
65                  70                  75                  80

Leu Thr Asp Leu Val Glu Asn Ile Gln Glu Val Ile Ser Ala Gln Leu
                85                  90                  95

Gly Lys Lys Arg Ser Lys Ala Phe Asn Leu Ala Leu Lys Asp Phe Gly
            100                 105                 110

Ile Glu Tyr Ala Lys Ser Ser Arg Ser Thr Cys Arg Gly Cys Glu Gln
        115                 120                 125

Lys Ile Asn Lys Asp Leu Val Arg Leu Arg Lys Thr Val Tyr Asp Thr
130                 135                 140

Glu Val Gly Met Lys Tyr Gly Gly Gln Pro Leu Trp His His Leu Glu
145                 150                 155                 160

Cys Phe Ala Gln Leu Arg Ser Glu Leu Gly Trp Phe Ala Ser Gly Glu
                165                 170                 175

Asp Met Pro Gly Phe Gln Ser Leu Ala Asp Asp Gln Ala Lys Val
            180                 185                 190

Lys Asn Ala Ile Pro Pro Ile Lys Ser Glu Glu Leu Pro Asp Thr Lys
        195                 200                 205

Arg Ala Lys Met Glu Leu Ser Asp Thr Asn Glu Glu Gly Glu Lys Lys
210                 215                 220

Gln Arg Leu Lys Asp Gln Asn Asp Ala Tyr Phe Arg Phe Arg Asp Asp
225                 230                 235                 240

Ile Lys Asn Lys Met Lys Lys Asp Ile Asp Ile Leu Leu Lys Phe
                245                 250                 255

Asn Asn Gln Gln Pro Val Thr Gly Asp Thr Glu Lys Leu Phe Asp Gln
            260                 265                 270

Thr Ala Asp Leu Leu Thr Phe Gly Ala Ile Glu Ser Cys Ser Glu Cys
        275                 280                 285

Asn Ser Cys Gln Phe Ile Val Asn Lys Ser Gly Tyr Ile Cys Asn Gly
    290                 295                 300

Asn His Ser Glu Trp Thr Lys Cys Asn Lys Leu Leu Lys Glu Pro Thr
305                 310                 315                 320

Arg Ser Ala Cys Ile Val Pro Lys Glu Leu Lys Ala Leu Tyr Asn Phe
                325                 330                 335

Leu Asn Thr Val Lys Glu Ile Pro Ser Thr Arg Ile Phe Asn Asn Phe
            340                 345                 350

Pro Pro Asn Lys Ser Thr Phe Ser Arg Ser Leu Leu Lys Thr Asn Lys
        355                 360                 365

Asn Asn Asp Val Leu Val Arg Pro Thr Ile Pro Arg Ile Ser Pro Pro
    370                 375                 380
```

```
Leu Tyr Asn Leu Lys Phe Ser Ile Ile Gly Leu Lys Asn Gln His Lys
385                 390                 395                 400

Glu Leu Arg Lys Arg Ile Glu Asn Leu Gly Gly Lys Phe Glu Val Lys
            405                 410                 415

Ile Ser Glu Asn Thr Ile Ala Ile Ile Ser Thr Glu Leu Glu Ile Gln
        420                 425                 430

Lys Lys Ser Thr Arg Met Lys Phe Ala Glu Glu Leu Gly Ile His Ile
    435                 440                 445

Val Pro Ile Glu Phe Leu Asp Phe Val Glu Ala Asp Thr Glu Gly Ala
450                 455                 460

Ile Lys Tyr Ile Asn Ser Thr Cys Ile Cys Ser Trp Gly Thr Asp Pro
465                 470                 475                 480

Lys Ser Arg Ile Pro Lys Glu Thr Thr Lys Ser Leu Asn Ser Asn Ser
            485                 490                 495

Ile Tyr Thr Lys Ser Met Pro Val Ser Arg Thr Phe Lys Val Lys Asp
        500                 505                 510

Gly Leu Ala Val Asp Pro Asp Ser Gly Leu Glu Asp Ile Ala His Val
    515                 520                 525

Tyr Val Asp Ser Asn Asn Lys Tyr Ser Val Val Leu Gly Leu Thr Asp
530                 535                 540

Ile Gln Arg Asn Lys Asn Ser Tyr Tyr Lys Val Gln Leu Leu Lys Ala
545                 550                 555                 560

Asp Lys Lys Glu Lys Tyr Trp Ile Phe Arg Ser Trp Gly Arg Ile Gly
            565                 570                 575

Thr Asn Ile Gly Asn Ser Lys Leu Glu Glu Phe Asp Thr Ser Glu Ser
        580                 585                 590

Ala Lys Arg Asn Phe Lys Glu Ile Tyr Ala Asp Lys Thr Gly Met His
    595                 600                 605

Phe Ser Glu Ile His
    610

<210> SEQ ID NO 3
<211> LENGTH: 23
<212> TYPE: DNA
<213> ORGANISM: Drosophila melanogaster
<220> FEATURE:
<221> NAME/KEY: misc_feature
<223> OTHER INFORMATION: primer PI for amplifying PARP-I

<400> SEQUENCE: 3
aaataataaa tgtcttgaaa ttg                                           23

<210> SEQ ID NO 4
<211> LENGTH: 21
<212> TYPE: DNA
<213> ORGANISM: Drosophila melanogaster
<220> FEATURE:
<221> NAME/KEY: misc_feature
<223> OTHER INFORMATION: primer PIII for amplifying PARP-e

<400> SEQUENCE: 4
gtcttgattt tgtgtatacc g                                             21

<210> SEQ ID NO 5
<211> LENGTH: 18
<212> TYPE: DNA
<213> ORGANISM: Drosophila melanogaster
<220> FEATURE:
<221> NAME/KEY: misc_feature
<223> OTHER INFORMATION: primer R4 for amplifying PARP-I or PARP-e
```

```
<400> SEQUENCE: 5
ttttatgaaa ccaattcg                                                      18

<210> SEQ ID NO 6
<211> LENGTH: 17
<212> TYPE: DNA
<213> ORGANISM: Drosophila melanogaster
<220> FEATURE:
<221> NAME/KEY: misc_feature
<223> OTHER INFORMATION: oligonucleotide D1 for detecting PARP-I or
      PARP-e

<400> SEQUENCE: 6
gtgtcgtgga tgtgaac                                                       17

<210> SEQ ID NO 7
<211> LENGTH: 18
<212> TYPE: DNA
<213> ORGANISM: Drosophila melanogaster
<220> FEATURE:
<221> NAME/KEY: misc_feature
<223> OTHER INFORMATION: oligonucleotide R2 for detecting PARP-I or
      PARP-e

<400> SEQUENCE: 7
ttggaattct ggattttg                                                      18

<210> SEQ ID NO 8
<211> LENGTH: 30
<212> TYPE: DNA
<213> ORGANISM: Drosophila melanogaster
<220> FEATURE:
<221> NAME/KEY: misc_feature
<223> OTHER INFORMATION: 5'-copia sequence for detecting PARP-I or
      PARP-e

<400> SEQUENCE: 8
ccgtttgatg gcgagaagta cgcgatttgg                                         30

<210> SEQ ID NO 9
<211> LENGTH: 27
<212> TYPE: DNA
<213> ORGANISM: Drosophila melanogaster
<220> FEATURE:
<221> NAME/KEY: misc_feature
<223> OTHER INFORMATION: 3'-copia sequence for detecting PARP-I and
      PARP-e

<400> SEQUENCE: 9
ccatcgtaac acgaaggcaa tgtgatc                                            27

<210> SEQ ID NO 10
<211> LENGTH: 50899
<212> TYPE: DNA
<213> ORGANISM: Drosophila melanogaster
<220> FEATURE:
<221> NAME/KEY: misc_feature
<223> OTHER INFORMATION: PARP-e genomic sequence
<220> FEATURE:
<221> NAME/KEY: misc_feature
<222> LOCATION: (1)..(50889)
<223> OTHER INFORMATION: n is a, c, g, or t

<400> SEQUENCE: 10
tctagaccac ggcaaaaaat cgtgtgccaa aaatnntatg gcgttacgca tcttgttatt        60
ctagngtctt tggatatggg gtgatcattt tgagaattta ctgcccgaag gtctaaattc       120
```

```
ctgtcatctg tggttacatt tttttcgaaa tcgggaaatt caagaatttg tttgtttatt    180
attaaagctt taagttttag aatgcgcctc tatgtattca aggttttgtg catctatctt    240
gcacctttt tttttaatt tggtcattgg ttttgctata tctgcgttat tggaataaa      300
ctcacgataa taaccggtta gtccaaggaa agctctgatt ttggaattgg atggctgttg    360
tttttagagg gtttggtttt ataccgttag ctttttttt aagaattcac atttatcaag    420
tttcaattat aattttgctt ctgcactaat tgttaaaaaa gttattatat cattcaaata    480
tactaaacag tgtttgttaa gcaaatgtcg aaggatatta tgcatgcacc tttgaaaagt    540
cccggtgcat tcctaangcc aaatggcatt cgaaggtact cgtaataccc gttttcgatg    600
gcaaatgcag ttttggatat ttcttttctg tttgataaaa tgcttttgcc agatcaatag    660
ttgtaaaata ttgacatttt cctaatgtac caaggatttc gtccatgttt gctattggat    720
ctctgtcggg aattagttat ttcataatcg ctacgctata cttgatttta ccacaagcat    780
cagtaagcaa ttactattcc taattaatcc gtgatttagc gtttccagta attggttttc    840
gactttaatt tcgtgcgttt gagcaaaagg gtaaagtggt gcgggtggca aaatgttttt    900
ttgcatatcg atagatattt acaagactga tacaaaaatc aaaaaatttt taaaaagtgt    960
tggtgttacg tgctgcctgg cttcttatat cctatttcct atatcctata tccctatatt   1020
tgtagcttct agatatatcc ttgaccaaaa ccagtgcagt ggcgaggatg acacgaaaaa   1080
cgaagttccg tgtgagtatg tgtgactgcc tccgaaattt ggacagacgt tctactttaa   1140
gttgtgcgtg atccagatga aagtcgataa agcagcgaat gaacgcacgg gtaaggcaaa   1200
cgtacggtgc taacgaaaat gtcgacaata ttttgcccca ttcgaaaaca atttcaaaga   1260
gcatcgttat tatggcatct caagagcact ttggtccagt taaagcggag attgtaanag   1320
ttcaagctgt gtcgtatgga cagaccatca tttaagattg tcttatctgt cctttaccat   1380
acattatata agagaaggca tattggtaat gaaaggagaa tcctgcacag gtaattgaat   1440
ttaaatataa atttagtgct tttcaatcac caaaaaaatg aataatgcta attatttat    1500
tattttttta gatgtaatta ttcttattaa actaatagat attaaaaaat tttggttgca   1560
accttgataa agaccagcct gtgattgtta cggatagagg ttttaacatg ataacgtcct   1620
tccaaggata cgaccatatt ttttgcacaa cattatagag gcaacggtaa aaaaaaatta   1680
tagaattttc taaaatggtt gatacatgca gtaaaatagt taagttttt aagaagtcag    1740
ggtaaatttt ttctttaaat acgacattga aaagcttgat actgatttaa ataaattggg   1800
gagttatgtg tttctagacc acggcaaaaa atcgtgtgcc aaaaatnnta tggcgttacg   1860
catcttgtta ttctagngtc tttggatatg gggtgatcat tttgagaatt tactgcccga   1920
aggtctaaat tcctgtcatc tgtggttaca ttttttttcga atcgggaaa ttcaagaatt   1980
tgtttgttta ttattaaagc tttaagtttt tgaatgcgcc tctatgtatt caaggttttg   2040
tgcatctatc ttgcaccttt tttttttaa tttggtcatt ggttttgcta tatctgcgtt   2100
atttggaata aactcacgat aataaccggt tagtccaagg aaagctctga ttttggaatt   2160
ggatggctgt tgtttttaga gggtttggtt ttataccgtt agcttttttt ttaagaattc   2220
acatttatca gtttcaatt ataattttgc ttctgcacta attgttaaaa agttattat    2280
atcattcaaa tatactaaac agtgtttgtt aagcaaatgt cgaaggatat tatgcatgca   2340
cctttgaaaa gtcccggtgc attcctaang ccaaatggca ttcgaaggta ctcgtaatga   2400
cccgttttcg atggcaaatg cagttttgga tatttctttt ctgtttgata aaatgctttt   2460
```

```
gccagatcaa tagttgtaaa atattgacat tttcctaatg taccaaggat ttcgtccatg   2520
tttgctattg gatctctgtc gggaattagt tatttcataa tcgctacgct atacttgatt   2580
ttaccacaag catcagtaag caattactat tcctaattaa tccgtgattt agcgtttcca   2640
gtaattggtt ttcgacttta atttcgtgcg tttgagcaaa agggtactga tttaaataaa   2700
ttggggagtt atgtgttgta tttagtacgt atttaatagt atttgtaaat gtttatgtat   2760
tgaagatttt taaatttatt taataaacct ttcacctttta aattttcctc ctgatttagg   2820
tgatgaaata gatttgagtt ttctattggt tctggtgtct tttggatata tatatactaa   2880
taagttgaaa ttgtttgaat tcatgcgcgt cttgaagtct catttcgtca atagacattt   2940
tggttcgttc actgtccgaa ggtcttagcc gtatttttag atgtggccaa ccctccaacc   3000
ctcgttgagg gtacgcattt cctctgaaat gtgctgtttg atgattttga gttttattgg   3060
gatgttgtgg aaaaggattt tttttaataa ttcgttatgt gttcatgtat tggattggtc   3120
tgaaataatt aggtaccggt cacataggtt ggttattagt catctgctgt gtataggtgg   3180
gtctaaatgg tggttattaa ttaggttgga agggttgaga atattgtggg taacttggtc   3240
gatattgagt ttggtcaagt ttattgaata tgtgtgattt agaatgttga ttaagattta   3300
agtttttatc tggattttta tttaatttaa aattaatatg ttcatcatat attgcaatag   3360
aaattaaaga tcttacgtca taatgtgtta aaatagtgaa taattgtatt ggtagttttc   3420
taatcagcat tttaatagac ttaataaata ataaatttat taaataagaa attccaattt   3480
acgtcgcgtt tctgcttctt cgcagaattc tcttcgattt ccttttttag ttgtctccct   3540
gaagttcacc agtagttcgg tgcttggggc ttaaattctg agattatttt ggatttcagg   3600
gttggccaat cttcgatgtt cggaagtccc atagatcgtg ttacttgtcc gtccaagttt   3660
cttttgatgg ctccaagtaa aatcctctgt tgtcgcacat cattcgtttg gtagattgaa   3720
attacgtagt ccaacctgct tatgaagggg tcctggatca cccttaaatg gcattatgtt   3780
ttttagctga cgacggtatt tagcgaggtt gttgtcgctt ggcgcaacta tttggggtgc   3840
ggcaataatt ggatgtgccg tttttattgt agattttttat tttgtattgt tttcgaatac   3900
tttttgtatc ctactaatta ttccagtaaa atgtttgtat attattgagt cgtccagcca   3960
gttgactgag gacaacgtta agaaatgaaa aaaattatcg gagagatagt tttgacgtct   4020
ttattctttt gatctcagct taaaaataaa tgttagttac aaaaatcttt cttatactgc   4080
catttctttt aaattatttc gaaagcgagg tcccccgctt gggatattgg ttgtatacag   4140
ctaccagatg tggattgttt acattgcgtg ggattcgcca ctctgcatat tcttatttct   4200
tccgaaagtg ctgattatgt gaatatgtaa tatgctcact ctttgttcgc atattttaac   4260
gctgcctgtg tgcatacata atttgccctc ccactagcca catgcatctc ctaatcggga   4320
gactggaatt tatcgttctc ttagttttaa ctactactaa ataaaagctt aagtaatttt   4380
gtagtaaaat tcaatatccc ttataaatat atgtcgtgga ttttttttacg gtatatgtag   4440 tttttaaaaa tcgtcttaca aacattaaaa atctacctttt tttaatctaa ctagattttt   4500
ttaattaaaa tttttctgtc tatttatagg cgttccagct atggcaggta gcgcaataat   4560
cgggggcgta ctcttagctc ttatcgaagg tgttggaata ctgtttacaa gaatttctgc   4620
tgaccagttt aaaaatccga taccacctgc agaagacccc gtagcccttg gagatcctgg   4680 aagaaaatttt tcatttgaat ccgcttctaa ccgaacacaa tatcaataaa ctagtaacca   4740
tgtgaaaaca aaaaacaata acctttagaat aaggtgataa atatgtattg attattctta   4800
ttcatgatcg ctcagctgta gtcgagttcc ccgactataa gatacattat taagctagtg   4860
```

```
gaagtgatac cgctaaattt catcattgtt ccggcatatt gatacatatt ggataatata    4920
atcaaaaaga attggaggtt tgtttgtgta agtaaggcaa atcgtttgaa atttacaaga    4980
ctaataaata tataaaaaag atcaatatat ttttcaaaag tgtgtggtta gggggcgata    5040
aagtggtgcg ggtggcaaaa tgttttttg catatcgata gatatttaca agactgatac     5100
aaaaatcaaa aaattttaa aaagtgttgg tgttacgtgc tgcctggctt ctaaatatat     5160
cctatttcct atatcctata tccctatatt tgtagcttct agatatatcc ttgaccaaaa    5220
ccagtgcagt ggcgaggatg acacgaaaaa cgaagttccg tgtgagtatg tgtgactgcc    5280
tccgaaattt ggacagacgt tctactttaa gttgtgcgtg atccagatga aagtcgataa    5340
agcagcgaat gaacgcacgg gtaaggcaaa cgtacggtgc taacgaaaat gtcgacaata    5400
ttttgcccca ttcgaaaaca atttcaaaga gcatcgttat atggcatctc aagagcactt    5460
tggtccagtt aaagcggaga ttgtaaagtt caagctgtgt cgtatggaca gaccatcatt    5520
taagattgtc ttatctgtcc tttaccatac attatataag agaaggcata ttggtaatga    5580
aaggagaatc ctgcacaggt aattgaattt aaatataaat ttagtgcttt tcaatcacca    5640
aaaaaatgaa taatgctaat tattttatta ttttttttaga tgtaattatt cttattaaac    5700
taatagatat taaaaaaaat tttggttgca accttgataa agaccagcct gtgattgtta    5760
cggatagagg ttttaacatg ataacgtcct tccaaggata cgaccatatt ttttgcacaa    5820
cattatagag gcaacggtaa aaaaaaatta tagaattttc taaaatggtt gatacatgca    5880
gtaaaatagt taagtttttt aagaagtcag ggtaaatttt ttctttaaat acgacattga    5940
aaagcttgaa aaccaaagac actagaataa caagatgcgt aaggccatac tattttttgg    6000
cacacgattt tttcgccgtg gctctagagg tggctccagg ctctctcgaa ttttgttaca    6060
gagcggagag cgctacagcg aacagctctt ttctacgcat acagtgatgg cagacaactg    6120
tatgtgtgcc catgtatgct catgcattgt aaatttgaca aaacatgccc ttcaagttct    6180
tggactttaa atctatatta ttttttgatca attggcacca tgcgaaaaat tcttgttttt    6240
cattgcctta acgttattat aatttgaaaa tagattagaa atagccaaat ctatgtacat    6300
attatcacaa aataaaattc aaaactgact ttatatatat atacagttgc ggtaacaata    6360
atagcaccat aagcacattt cgtgtttgtc ccagcgtttc tctattttct gacactttt     6420 tcatcatttt actcactaaa cttaaatact acaatgattt tcaatcgaaa taaaaaaatt    6480
agtaacagta acagtaacaa aaaaaactgt taaaaaaaac aaaaaaatag cactgtttct    6540
cgtagtttgc taagactaac caaagaaata aaaaaataat tcaacaaatg ggattatatc    6600
ttaagaacta tgtttaaaga atcttaatat ttagtttgcg tggaccttt gggttggcaat    6660 aacagccgcg catcgtcctg gcatggagtc caccaagtcc cggcacagtt tttgaggaat    6720
ttaccgttat tattgggttn ggcttcaaaa accttttttt caggncttnc caagggtttc    6780
gatgggatca gtcggtgatt gagnaggcca gtnttcctgg acaatctgnt ctaacccttt    6840
cactttctgg tcggnggttg ggncgtatcc gtcgaaagtc aaaccacggt tcatcccgg    6900 atatgggaga tacatttccg gaaattgngc tatcgccttg gcatggagtc caccaagtcc    6960
tgtcaccgtt tttgagaaat tttggtccat gaatccttga caacacccca agatcctcg     7020 ttattattgg gtttggcttc agaaatcttt ttttcacttc cgcccaaagg ttttcgattg    7080
gattcaagtc gggtgactga gcaggcgatc gcattactcg gatcgatttc tgctcaaacc    7140
actttctagc tttcttgctc gtgtgttttg ggtcgttatc ctgttgaaat gtccaagcca    7200
```

```
acggcatatc atcctcggca tatggcagca tcacattttc caggagatct gtgtaaatgt    7260
gctgatccat gatgccttga atctaatgga tcggacctac tccatagtat gaaaatcacg    7320
cccataccat gatgtttgat cccccgtgct ttaccgcctt aaaggtgaag cgaggattat    7380
attcagttcg tggtggacgc cgaacataag accgagagcc tttcccacca aacaacacaa    7440
ttttgctctc atctgaccac aaaatgttgc gccacttctc cacaggccag tccttgtgta    7500
tcttggcata ttcgagtcgc tttgccacat gcttaacagt caaaagcggg acttttctgg    7560
gactgcacgc attaaggttg ttttgtctta agcgtttgcg aactgtttcc acgcttgcag    7620
ctatctgaag ctccttcttc agttccgtcg ccggcttaaa aggctccttc ttgctttgcc    7680
gaaccaagcg cttgatctcc acgttggaca ttgagggctt tcttccacgt gtttcgtcct    7740
tttcgacaaa cagcattgtg gatcattttg tttgaacacc cgacaattcg accaatttca    7800
gcgtaggttt tacattcaga gatcatgttt ttaatcaaat ttcttttttc gacggtacaa    7860
tgcttttcgc gacccataac tagagaattt ttggtcttcg tttggaacaa attcaattaa    7920
aacctttaat acaactcctt ttttcaaaat ttgtcgaaaa aatcccaaa tcactcctat     7980 taattttatt caacaaatac gtggtcagtg ctattttgt taccgtctca tttcgcgcgc     8040
ttttgcagca agtgcccaaa aacaaaaaga accgttacat tgagagagta aaaatttctt    8100
gctcagagag gcgcgtatgt tttagggatg caagaaaagg gcctatcgat agtgcgggtg    8160
ggggttgatg gcttttggag ctatcggtgc ggtcgtgcgt ggcctatcgt tttatcgatg    8220
taaaaccggt ggctagcgtt agttaatcaa atactattca aatttgaata tgtcggagat    8280
gccaagcgcg acttttcatt tacttcagcg tccatattgt ccagcacatc aagtcgcctg    8340
cgtgttgttt cttctgtcgt tctaagcaga ctaatttact caagcgtcgc cttcgcgatg    8400
cttttcttct attcctcacc ttcactcaat tatttcatcc ttacttcgtt tccagaaact    8460
atacaacaac aacaacagcc acacaaatga tgcccactca ataacggaac gctttccgtg    8520
aatttcattg ctcgctgctc attcttaaca taacggatca ataacaaaat gtcggttaca    8580
ttctactact caatcttgct tgtgaaattt tgctgatcaa acgtgcttaa agcgaattat    8640
taaatttaat aaaatgcctg gaaagagata aactttgaag ttacccaatt aataaactat    8700
aaccaccagt tgggaaaatc ttttccagaa taagtataaa tgttttctgt atcccgtaag    8760
accgtctact attttttaaa aggctcggaa aaagaggaca ggcttgaacc taagagtggt    8820
ggtgggcgga aaattaaaat taaaagcgt gtagaccgct ttattatgcg aatagagatt     8880
gcgaaccccc ggtcagatca cttgctctgg atatcaggca agagtgtcac ctaactgtgt    8940
cacacgaaac tgtgcgccaa gtcatcctac gccatagata ctcttcaaga gttgcgagga    9000
aaaatccttt gctatcagat gccaatatgg aaaagcgtca ttaattcgct gtgaacaagg    9060 tgatcatcc agaagagtac tgggatgacg tcatatttgg tgacgaaaca aaaattatgc      9120
tcttttataa cgacgggcca agcagagtat ggcgcaaacc gctgagtgcg ctagaaaaac    9180
aaaatatcat tccaacgata aaatttggaa aaatgtcact gatggtttgt ggctgtatca    9240
ccagccatgg agtgggaaaa ctagccttaa tttagagcac aataaatgcc gtgcaatatc    9300
taggaatctt aaaaaacaaa tttgaaggcc ggtgcagaaa aatttggtct agttagcaac    9360
aacaagccaa attttatatt ttaagaggac atgatcagaa acataaagag tgcaatgtac    9420
gcacctggcg cccttataac tgtggtaaag tgatcgatac gccccctta gagtcctgat      9480 ctgaacccca ttgaaaattt gtggacctac ttaaagaaga aggtggcaaa aagggcccta    9540
aaacacgaca acagcttatg actgcaatag tcgaatggtg tgaaaagatc ctgcttgaat    9600
```

```
atgacctaca aaaacttatc cattccatga aaaaaaggc ttcaacttgt agcgtaagcc    9660
aacggggaac atactacata ctaaaacttt taaaatttta atgaaataat ttaaaaattt    9720
aggagtaaac ttcgattaag tgttttgtgt aaagagtttc ttgaagtgtg taaacttgga    9780
atttcttgtt tatttcttg tatatttaat attttaatt tgttttttga tttatactta    9840
aaataaatgt tgtttaatta tattgaataa agaattgcg tttaattaag caaagaaccc    9900 ttcatttta cctttaaaat caaaaattca acttatttca cagtttcttg acaaactgta    9960
attagtttct tagctttgaa gcgtagaagc cagtttgcaa aaggaaggac aggagggcat    10020
ggttatattg acttggctat tcgtacttat taagaatgta gtgttttat acagccgtaa    10080 atgtcttctt taatgcctcg caacttttt aaagatatta aatattctc tgcgaggtta    10140 taatatgaat ccgtgtttct ctctccatag tttcttaatt gttggcaact tatcgacgtt    10200
atcttgacgc acatcgaaat ttacaaagta ctggtattac ccattggcca gtgcgcgttt    10260
gactactaat aattttacgt taataatttt ttaagtcctt ttaacgttgt tttggcaata    10320
aaaatgactt ctcgcgataa tattttcgag gaaaaaatat gcaatagatt agatcattgc    10380
gtttctgatg tattaattaa aggatgtgag tacgaacatt tacgtaacat ttttaaaccg    10440
tggtatttgc atattgaaat atcaattttt aaaagcaaaa tcaaacggt attttaaatg    10500 gcatttatta ccatttttaa taacccagca tatgatgtat gaaaaattat aatttggcta    10560
ggctaagttg tataaagttg tatggcatga gtagacaagt gtattgttta aatcttgcaa    10620
actaaaaata atttttataat taaatggtt tgcttaagct aaacattcag aaacgtaatc    10680
atacctcgca gatttccaaa aaacatcaaa atatgccgaa gttcgggata taaaataatt    10740
ttttatttga attgttgata gaattatgca ataacaatt ttaatatttc gttgcaaatc    10800
cttgctgtct atgaaaattt gcaggctatt aggaaacgag ttggcttagt aagaggcaaa    10860
gttgtttgcg attttcactt tctcagcatt ttgttttaaa acggtttggt atccaaattt    10920
gcaactttct tcaatcttac tctactcatt gttcttgagg cttttaaagc taacttttt    10980 gtgaaaatct ttggtatgcg gtgtattaca cgttttcct agttcggcct tgcgaaaaac    11040
ttttaagatc ggaatctttt gaataattc gtgcacattg gacttcctcc atcccaccaa    11100
ttctgtaatt ttcaaactga tgtttcttca taaatcaatc agctgtggaa tttccaagga    11160
cgattgctac ccttttggag tcattccaaa gcccacaagc cagctcacag aagctggggt    11220
cggaaaaatc gaattttaga tatttgaaag ctaaatcgt ttgcccacca attagttttt    11280
atgcccacgt ccagatttcg agatctgtat tttcgaaaaa gaaaattcgc gaaaataaaa    11340
acgttgactt tttctatcgt tttttttta tacctaattt attttgtaa ccttaaaaaa    11400 tacctgttta aaaatattta tcgtttgccc aacccttaa agtaactaat tttgttaagc    11460
cacctctcga atattattt ttttcaatta ataacatttc attaccattt gataaaacgg    11520 ttttaagaa tcgatatcat cctttaaaat tagattgcc catactttaa cattagtttt    11580
catcatttgt ctatccttta aaatttttt tatttgcact tccatttttc tatcgtttta    11640
tttaatactt aatttatttt tgtaacatta aaaaatacct gttcaaaaat atttatagtt    11700
tgcccaccct taaagtaac taatttcgtt agcccacctc tcgaaatatt ttttttttca    11760
attgcaaaaa aaactaatt tgtcggcaac catgggcaaa caattccatt tatcaaattt    11820
cgattttccg accccagctt ctttgggatc caccgaccac ccaatactgc cacaaccaca    11880 attttaaaa atgtgttgaa aatgttgatt ttactatttg tcttgccaaa catatctaaa    11940
```

```
aaaatcgtac caagctcact ctaatattag ctcaattaaa taatttaact aattaaatta   12000
aattggataa ataaaatacc acttttttc aggtggaggc gtaattattg gatctgctgt    12060
atctttctta attttaaaga gacgagcatg gcctgtatgg ctcggcgctg gatttggaat   12120
gggcatcgct tataggacgt gtgaaaagga tttaaattct ttaaaataaa gattattacc   12180 tttaattca aataaaatat ttaattgagt aatgaaaata atatacttat ttagtgctta    12240
ttaatactga ggccttaaga gtgttgaatt atgtgatttt ccaaaaatat tccaaaaaag   12300
acaatttaat attataatcc atttgtgatc accattatcc gtcttgaaga gaaatctatt   12360
ttgcatgtta tacaccatgt caggatacga ttatttttaag aagctctcgg agagctctag  12420
agaaagcagc tcttttgtac gctaaggctg acgacagagt gtgttcgaga agcgataata   12480
ttgcgcgaaa acgagcgata aaccactgca tgcatttta agtggaatcg ctcgaaagat    12540
gtcagagtga gagcgaagcg gacgactacg atataatgga acaaaacgca agtacaagta   12600
tgcaagccca aatcaacgga acttaaggag atggtggcaa acttggcaac gatggtccaa   12660
acggcatgct tgcaacaaca aagtcaagca caagggactg tggaacaaga aacgacacgc   12720
ttacgtcaga cgctggaatg atcgagacac acacatgcgc caaacgggat gcaaccggaa   12780
aatgtgctct catcgccaca cgctagaagc tcaaggtcaa ggttttacaa gcatcaaaga   12840
aatgatagga attctgccgg attttgatcc aatcaaggga tctatcacat cggagcaatt   12900
catcgcaaag gtagagcaac tacaaagcgt atacatgtgg acaagtgacg ctgtgctgtt   12960
tgcagtgcag cataagatct tgattttcca tgtttagtga gtacggccga tgtgcacagg   13020
gaattgatgc gtcgcaagcg acgcaatagc gagtcattaa ttgaatactt ttatgcgatg   13080
gtagctattg gacggcgtgc gagtgtcgat gaaccatcaa taaattcgta tatcatcaac   13140
gggcttaatt caaaagaact cacggaatca ttattagcga tgaacatacg cacttgttca   13200
gagctgctaa agtcgttgga aaatttgaga ttttcacaag agatacatca acaacaatac   13260
aacgcaatac aacgatgctg atggcaagat gaaagcagtt aaatgttata attgcaataa   13320
tttcgggcac tttgcagcaa aatgcacagt gccacagcga aaggaaagat gttccaaatg   13380
ctctaagatt gggcataatg aaaaggattg caagttctca ttggaggcca acagtttgaa   13440
gcattcatcg acacgggcag tgataacacc ctaatgaaag aagcagcagt gccagatgga   13500
gcaatacggc agcccgagaa tcaaacgtct gaaaggcttt ggaggatctg tggtcgaatc   13560
gaaggagtgc attctttcag agtttgcata tggcaaactg agactcctca cgcaaattca   13620
ggtggtacca aacgaagtcc taccatatgt attgtatgta tatatatgtc ctcgtgggca   13680
gagatatcat ctgccacgat caggaaatgc tggttgcccg aaaattcagg atcaaccgtt   13740
gacagcagcg gagcaggtcg ggtttaatgt taacacggac attgaccccg accaccagga   13800
acaggtgagc gatctattaa agagctataa agagtgtttt gccgaagatt tgtcaaatat   13860
tggcaggtgc aaaaccacga agatggatat agaggtatcc tttacgaaag ccatcttggg   13920
gcggcgatat caagtgccgt ttgcccaaag ggagatgatg actaccataa taggtgactt   13980
actgaagtac gggataattg aaaggagcaa gtcaacgcat gcagcatcag caatattggt   14040
gccaaaggca aatggagaac ggaggctttg cgtggactat cgggctctaa acgcagtcac   14100
tataaagaag cgatatccga tgccgattgt agaggagcaa ttgcaaagc tatccggaaa    14160 tgtatacttc acgacgctgg atatgacatc cggttattac caggttccga tggacaagaa   14220
aagcaaaaat ttgacggcat ttatggcacc agatggactg tacgaattta atgtcatgcc   14280
ctttggtctg gtgaatgcac cgatggtctt ccaagaagtc attactgaga tcataatatt   14340
```

```
aaaggaattc ctggatgctg ttaagttggc gggcttaacg ctgcgcccat ccaaatgcgc   14400
attttatgaa aacgaaggtg acctttttgg gtcatgtgat cacgggcaac gggattcagc   14460
caggcaatga aagactaac  tgcatcaatg aatatcaaag gccatgtaac gaaacagaag   14520
tacgcagatt cctgggagtt acaggattct tcagaaaatt tgtcaaagag tacagtatga   14580
ttgcgtatcc attgagcaaa ttattgaaaa aggatgtgga cggtatatgg tggaagatct   14640
gccagaccac aatgttactc agcgacgcta ttgtaacgtg atgtcaagcg accatatgag   14700
gccaatgtgt gccttaattc caaacctgga tatagatgag ccgatatatg aatataacga   14760
cgacgcagga atgtcaggag aggccggatg ttaagaggaa gagcatgaga gaggggagt    14820 tgcttgcgag atgccaggga gtgcggacgt gtgctcgctg ggtgaacgat gaaggcagat   14880
gtatactgaa gacttataac tattgtaaca cattaataaa agaaaagaat aaacatgaag   14940
gatcaacctg acacatttt  atggtcacaa ctgtcatata atactttat  atttaattac   15000 taaaatcta  gttttcacag ttgtcgactt cacaaaaatc gtccccatat acgtacaaga   15060
cacgctttga ggaatccata aaacaacctc aattcttgtc aagtgattcc aaaaactgta   15120
actgtgcaat atttcagaaa atatcagtgg agaatgggca caagaagtcg aattaatttg   15180
aaatgctgta tagtctttct agagtggctc caggctctct cgaattttgt tagagagcga   15240
gagagcgaag agcgctcagc gaacagctct tttcaacgca caaagtgata gcagacaact   15300
gtatgtgtgc acacgtatgc tcatgcattg taaatttgac aaaaatcttc aaagttcttt   15360
gactttaaat ctatattatt tttgatcaat tggcaccatg cgaaaaattc ttgttttgca   15420
ttgccttaac gttattatta tttgaaaata aatagaaat  agccaaatct ttgtacatat   15480
tatcacaaaa ataaatttca aaaatgactt tatgtaagaa tatttgtcat tagagtattc   15540
atcttgaggc gtgtgaaaaa ttaataaggc aatgattgtt gagtgcttgt gtccgcactt   15600
cgtgcctgaa gatatgaaca aagcaaagac actagaataa ttctagttat catatttta   15660 tgaaatttat gaaattacag tagttataat aatttctatt gnttttcctt taattaatta   15720
gtatatttat taagtcattt gacttaaaat gatgtaacat taatattaaa agtgtttcaa   15780
aaaaatattt ctcttttaaa aaattggtca gatgagagac aaattagaat taaacataac   15840
aaatttaaca aacaaattta aaaaacttta aaaatataat agtcaggggc gcgaattttn   15900
aaaatttttt atttatcata ttgntaggaa attggcaaaa ctccctaata tgtcaatgna   15960
aatcgttctt catcagaatg attcggccga aaatcgcttn tagccaccac gcacacatta   16020
cgcgttctcg ctctggttta ctcagacaag caagcaaatc tattttaga  ttttatgctc   16080 tnacgggagc gacggaaanag nccatttgg  ccgtccntna aaattgggtg cntngcccat   16140
cccattgtcg gtttgcccng ttcggcttct tggtatttct agtgtctttg gtagccttt    16200 gttccaatgt ggctttncca gtccggtcca agtgcnagcg taacccgagc atccanttna   16260
atccccngca tcncatnatt ggcatagtcc ancgttctca cgctggtcaa agcngctgcc   16320
cgcnatccca tgtgtgccta tagcntatgn atanatngta gcatnatatg cttcncatat   16380
tacggnttnc gcaagcattg ntacatncca ttcttggcac atgcatntcc gccatnnatc   16440
cnatttacct tttttgctta cgcttcagcg catgatttgt tgtgcatccc atnccgttct   16500
tttttcgttc ttttttgtac acatatnctg attagacatt cccgtttctc gcgactcact   16560
tcaagccgat caaatactct gtagtcagtc ttcagctgnc agttttngna tanagacgct   16620
ctctgaaatt attcgtgttt caatttataa ttggcttcag cgttgatctt tgtcttcgtc   16680
```

-continued

```
ataggcggat cctttattcc gactcgcant agtnnctacg taagtggcgc agtcggtagg   16740
atgatcctag ttgatgcgat attacaccta ttcanttctc tgtgtgtcat ccgctaaagc   16800
tcgtacaact tcaatatctc gcgtcggtaa atcggnaccn ttggttcann accaaaaaac   16860
ccccccccct tttganacca tctacntanc cnaaaccnca gagtgattgt gnaagtnccc   16920
nacttannat tgtatngatg gcnttcccgc atangggctt cgtgaattcg ctgagtagta   16980
aatccacaaa aggttactca aaannaagcg aaatagcaaa gtgtgcaaca catgaaaaca   17040
gctaaactaa gtgaaaacta ataaaagta attacgacta agtgaactac aataacaaca   17100
gttaacctaa gcgataaaaa taaataaact taaccagaaa taaacgaaga ataataataa   17160
cagtgtaact aagtgaaaac taaataaagt taattacaac taagtgaacc ataataaaac   17220
agctaaacta agtgaaaatt gaataaaagt aattacaact aagtgaacta caataacaac   17280
agttaaccta agcgaaaaat aaataaactt aaccagaaat aaacgaacaa taataataac   17340
agtgtaacca agtgaaaact aaataaactt aattacaact aattgaacca taatattaac   17400
agctaaatta agtgaaaatt aaataaaagt aactacaact aagtgaacta caataacaac   17460
agttaaccta agcgaaaata aataaactta gctagaaata aacgaacaat aacaataaca   17520
gtgtaaccaa gtaaaaacta aataaactta attacaacta attgaaccat aataataaca   17580
gctaaattaa gtaaagactt aataaactca actacaacta aaatgaatta aatgcaacta   17640
agtgaaacat tataataata ataagtgagc gaacaacaag aaacccatca aacacataaa   17700
cttaaaacga agacacaaac caatagtgag aactcaaacc ctatcccaaa tcgcgaacca   17760
aattaaacca caaaccttat ctaagctacg aacaaacatt atcaaantaa tacgactnnc   17820
tatagggaga ggatctattg ttgtaaagta ttggcatcta cctaatttgn ccaatatctc   17880
acccattcgg ggaatgggaa atttgtcgtt aacagttatc tcatttagat tcctgtaatc   17940
gactaccaac ctgcattttt tttcccagag gcgtctgcct tcttggggac cacccaaata   18000
ggagaacaat aaggggactt cgattttcga acaatcccct gttctatcat ttctttaatt   18060
tgtttgttga cttcttggtc aacgctttga gggtacttgt anggtttacg gtatactggg   18120
tcttcgtgtt gagtttggat gacatgttta atagtactgg tgaaggtcaa attttcgccc   18180
tctttgtact gaatgtctct ttattcgtat aggaccttct ttaaacattc aacttcctct   18240
gcatttaagt gttcgagtct atactcgtta cattcgcgta actcattatt aatcgcgaag   18300
ttggctatat cgntgtcaac ggacatggga tcgagatgtg ttacatcatt gtccactgtg   18360
nctttaacaa catttgaaat gaggcatttg ggtaatgcan tctccttctc ttgatgctga   18420
tgctttggnt taaggcactt angtgggnnc ntaaccttt gcattnnngc tttgattctg     18480
ccactaaagc ggaatcatnc tcttggtttg ngtcaangcg tntggatacg gcnccccttt   18540
ttnttcatan agaaacttaa atctntngac cctagtctta ctgaattcnn nnnnnnnnn    18600 nnnagacgaa actcnactt attttgatng ccgagtcccg agctcgaatt cacatttatc     18660
aagcttcaat tttaaaattt gcttctgtag ctttgaaaaa actaattgta tgggatgttg   18720
aaaaaattat tatatcattc aaatatacta aacagtgttt gttaggcaaa tgtcaaagga   18780
tattattcat gcacctttga aaagtagcgg gtgcattcct aaggccaaac agcattcgaa   18840
ggtattcgta atgaccgttt ttgatggaaa atgcagcttt ggatattgat tctaggtcca   18900
tttctatttg atgaaatcct tttgccaggt caatagttgt aaaatattga catttttccta  18960 atgtaccaag gatttcgtcc attgtttgct attggatatc tgtcgggaat agttatttca   19020
ttgagttttc tataatcaat tactacgcta tactttattt taccacaagc atcagttttt   19080
```

```
tttttggtac tatccaagta gtactattgt atggtgaatt actatcccta attaatccgt    19140
aatttagccg tttccagtac ttggttttct actttaattt cgtgccgttt gagcaaaagg    19200
ggtactgatt tgaataaatt ggggagttat gtgttgtatt tngtacgtat ttaaatggna    19260
tttggaaatg gtnaatttgg ctttcttaat atatatatnn atatattata tattataagg    19320
catttggtat gtgcaacctt tgtatgctat ttctatggat tcgtgttgtc cggggctgtt    19380
gaccgaataa ttttcgcttg gttcagagtt attttgattt tcttggtcat taattttggc    19440
gggttgaacc tgttgttgct cttcattaat gaacccatga ttttggtata gattgtattg    19500
attgtggtta taatactggt gttcataata attaagttaa aattgttcga agttttgaag    19560
tcaaatttcg tcaatagaca ttttggtttg ttcactgtcc gatggtctta gtcgtatttt    19620
tagatgtttg gatgtttaga tgttgttttc gttgagggta ggtatatcct ctgaaatgtg    19680
ctatttgagg attttgggtt ttgttgggat atcgtgggaa aggatttttt ttaataattg    19740
gttatgtgtt catgtattgg acgggtctga aataattagg tgccggtcac ataggttggt    19800
tgttagtcat ctgtcgtgta ttggtgggtc taaatggtgg ttgcatgcat tgtaaaattt    19860
ggttggaagg gttgagaata ttgtggataa cttggtcgat attgagtttg ggtattgcta    19920
ttgaatttgt gtgatttaga attttgatta agattaaagt ttttatatcg attttttattt    19980 aatttaaaat taatatgttc gtcataaatt ccctcatttt ttgcaataga aattaaagat    20040
cttacgtcat gataagttaa aatagtgaag aatagtattg gtagttttat atttatttat    20100
ttaataaata ataaatgtaa caaataagaa attncggttt gttacccttc aggtgtaatt    20160
tcgaaatcaa catttgacgt cgatttccgc aaaaagattg ggnnnnnnnn ngaattccag    20220
gaaacnctan ntganttcaa gtccnggccc gaattctcct agatttcctt tgttaggtgt    20280
ctccatgaag ttcacnagta gtttgtagtt cggtgattgg agcttaaatg ctgagataag    20340
tctggatttc agggttggcc aatcttcgat gttcggaagt cccatagatg gtgctacttg    20400
tccgtccaag tttctttcga tggctccaag taaaatcctc tgttgtcgca catcattcgt    20460
ttggtagagc gaaattacgt agtccaatct gctgacgaag gtgtgggagg gtttctggat    20520
cacgcttgaa tggcatgatg ttttttagcta acgacggtct tcagggaggt tgttgtcgct    20580
tagcgcaacg atttggggtg cggcaataat tggttgtgcc actgtaattn tttatttttt    20640
tattatactt tcttctttgt ttttatttat taaagttttc cgacagtttt caggttataa    20700
tctcttataa ttttaaaact aatatttaaa atttggaaat tgcaaaaatt atattttgga    20760 attttttagtt tattttaact tgttttaact tcttgtagtt tttatttcga ataataattc    20820
acttatgttt gtattgttta ttttaacttg tttcacgtat tagttttat ttcgaataat    20880 aattcacgta tgtttgtatc cttaaaatgt tattggtctt ataggattgt ttaattttct    20940
tcttttttct tctgtgttgg acaaccgaat tggatttata acccaagttg aagttaaata    21000
agagtcagtt gcgtaattaa ctgcgagaat tacggattat acaatttaat ttattttcca    21060
ctcgtggttc tgatactttt tgtatccttt tgcgccagta agatatttgt tatatttttg    21120
agtcgaacta atgtcccgtc agttgaactt ccttattcgg atatcagctt aagactaaat    21180
gatagtgaca aaaatctttc ttccccttttt ccatttttcct tgctcttttta tatgctactt    21240 ccaatgtgaa tttactttcc ttagcatagt caatggtttt ttagcataaa atgattcttt    21300
gttgatggtt gtaagaaaaa atgttggtaa attgttctac caaatactat ttcgtatgga    21360
caatatttat gtgccatagg aggggtcaaa gacactataa taacaagatg cgtaacggcc    21420
```

```
atacattggt ttggccaaag accctagaat aacaagatgc gtaacgccat acgattttt     21480 ggcacacgat tttttcgccg tggctctaga attatttcat ctaaggaaat tatttttgttt    21540 tatnaggant cgaaagctgc aaatcgcagt ttattattgg cggtctgaat ttttttaagtt   21600 tcaattagca tgtatgatat cgtaagaaat ttgtttgtgc taatatactt ttttttaaaaa   21660 tgttttgaaa gcccgagccg cggttagcgg ccaaaaggtg ccattcagga tgacaactgt    21720
ttgtaatttt tggtaaagaa tggccaaggt agggcgggca ttacacgatc ctccaccaca    21780
cctgaggatc gagcggaagc ttgtagggta aaagaatcgt tctctccgtt gtaagtgtcg    21840
ttgatggcga tttgccgccc ttttcttaat tggaaatctt aattgttcca ggacaaggac    21900
caccaccccc acataacccg acaaggagct gctgaacttt cgccgcgtgc gtactggaat    21960
atctcacaac aattaaataa tttataattg atattgataa tttctctgtg tgctctttca    22020
ataatttcaa aatctaaatc gctatcaaaa taaatgctaa tgnttctatg aataaaatga    22080
tcttgtaaaa tttgtgtggc cttttcaagt ggcattaaat catattgaat tgtggtaatg    22140
gagctccgaa tattattgga atgctctaca ttatttttat tgcttctgca aatgttgagt    22200
atctacactt aagaaggat ttcttcaatt ttactgaat tttcattggt tttgatataa     22260 tcgatttaa attgttattc gtttaatcta gttctccatc ctttgtaact tatagcattc    22320
ggttcccttc tccatctttg taacttatag cattcggttc cttaaagta tgaagtcatc    22380 taagagggtg atggtcacca gcaatgacaa actgtcgttt tagtaaataa agccgaaaag    22440
cttttgttgg cgagtaattc ttttcgata tctgtaattt aattcgtgtt cattaagtgt     22500
tctgctaata aaggatatgg gatggccatt ttgagaattt actgctcaaa gggttaattt    22560
actatcacct gtggtacgt tttttgaatg cgcctctatg tagtcaaggt tatgtgcatc     22620
tatctttgca ccttttttta aacatttggt cattggtttt ggtatgtctg cggtaatttg    22680
aaataaattc accataataa ccggttaatc caaggcaagg tctgatttgg aattggatgg    22740
ctgtcgttta aaggnagttt agttttatac cgttaggggt tacgacggac aaganggtat    22800
gccctaaaag gaaacggagt tnnnnnnnnn nnngaattca catttatcaa gcttcaattt    22860
taaaatttgc ttctgtagct tgaaaaaac taattgtatg ggatgttgaa aaaattatta    22920
tatcattcaa atatactaaa cagtgtttgt taggcaaatg tcaaaggata ttattcatgc    22980
acctttgaaa agtagcgggt gcattcctaa ggccaaacag cattcgaagg tattcgtaat    23040
gaccgttttt gatggaaaat gcagcttggg atattgattc taggtccatt tctatttgat    23100
gaaatccttt tgccaggtca atagttgtaa aatattgaca ttttcctaat gtaccaagga    23160
tttcgtccat tgtttgctat tggatatctg tcgggaatag ttatttcatt gagttttcta    23220
taatcaatta ctacgctata ctttatttta ccacaagcat cagttttttt tttggtacta    23280
tccaagtagt actattgtat ggtgaattac tatccctaat taatccgtaa tttagccgtt    23340
tccagtactt ggttttctac tttaatttcg tgccgtttga gcaaagggg tactgatttg    23400 aataaattgg ggagttatgt gttgtattn gtacgtattt aaatggnatt tggaaatggt    23460
naatttggct ttcttaatat atatatnnat atattatata ttataaggca tttggtatgt    23520
gcaacctttg tatgctattt ctatggattc gtgttgtccg gggctgttga ccgataatt    23580 ttcgcttggt tcagagttat tttgattttc ttggtcatta atttttggcgg ttgaacctg    23640 tgttgctct tcattaatga acccatgatt ttggtataga ttgtattgat tgtggttata    23700
atactggtgt tcataataat taagttaaaa ttgttcgaag ttttgaagtc aaatttcgtc    23760
aatagacatt ttggtttgtt cactgtccga tggtcttagt cgtattttta gatgtttgga    23820
```

```
tgtttagatg ttgttttcgt tgagggtagg tatatcctct gaaatgtgct atttgaggat   23880
tttgggtttt gttgggatat cgtgggaaag gattttttt aataattggt tatgtgttca   23940
tgtattggac gggtctgaaa taattaggtg ccggtcacat aggttggttg ttagtcatct   24000
gtcgtgtatt ggtgggtcta aatggtggtt gcatgcattg taaaatttgg ttggaagggt   24060
tgagaatatt gtggataact tggtcgatat tgagtttggg tattgctatt gaatttgtgt   24120
gatttagaat tttgattaag attaaagttt ttatatcgat ttttatttaa tttaaaatta   24180
atatgttcgt cataaattcc ctcattttt gcaatagaaa ttaaagatct tacgtcatga   24240
taagttaaaa tagtgaagaa tagtattggt agttttatat ttatttattt aataaataat   24300
aaatgtaaca aataagaaat tncggtttgt tacctttcag gtgtaatttc gaaatcaaca   24360
tttgacgtcg atttccgcaa aaagattggg nnnnnnnnng aattctccta gatttccttt   24420
gttaggtgtc tccatgaagt tcacnagtag tttgtagttc ggtgattgga gcttaaatgc   24480
tgagataagt ctggatttca gggttggcca atcttcgatg ttcggaagtc ccatagatgg   24540
tgctacttgt ccgtccaagt ttctttcgat ggctccaagt aaaatcctct gttgtcgcac   24600
atcattcgtt tggtagagcg aaattacgta gtccaatctg ctgacgaagg tgtgggaggg   24660
tttctggatc acgcttgaat ggcatgatgt ttttagctaa cgacggtctt cagggaggtt   24720
gttgtcgctt agcgcaacga tttggggtgc ggcaataatt ggttgtgcca ctgtaatnt   24780 ttatttttt attatacttt cttctttgtt tttatttatt aaagttttcc gacagtttc   24840 aggttataat ctcttataat tttaaaacta atatttaaaa tttggaaatt gcaaaaatta   24900
tattttggaa ttttagtttt attttaactt gttttaactt cttgtagttt ttatttcgaa   24960
taataattca cttatgtttg tattgtttat tttaacttgt ttcacgtatt agttttatt   25020 tcgaataata attcacgtat gtttgtatcc ttaaatgtt attggtctta taggattgtt   25080
taattttctt ctttttcttt ctgtgttgga caaccgaatt ggattataa cccaagttga   25140 agttaaataa gagtcagttg cgtaattaac tgcgagaatt acggattata caatttaatt   25200
tattttccac tcgtggttct gatactttt gtatcctttt gcgccagtaa gatatttgtt   25260
atatttttga gtcgaactaa tgtcccgtca gttgaacttc cttattcgga tatcagctta   25320
agactaaatg atagtgacaa aaatctttct tcccctttc catttccctt gctctttat   25380 atgctacttc caatgtgaat ttactttcct tagcatagtc aatggttttt tagcataaaa   25440
tgattctttg ttgatggttg taagaaaaaa tgttggtaaa ttgttctacc aaatactatt   25500
tcgtatggac aatatttatg tgccatagga ggggtcaaag acactataat aacaagatgc   25560
gtaacggcca tacattggtt tggccaaaga ccctagaata acaagatgcg taacgccata   25620
cgattttttg gcacacgatt ttttcgccgt ggctctagag gtggctccag gctctctcga   25680 attttgtta gagagcgaga gagcggagag cgctacagcg aacagaccaa aattgctctc   25740
tttccgctcg ctcccgctga gagcataaga aatctaaaaa tagaatttgc ttgcttgggt   25800
gagtnaarwm aasagancga gaacnaaagt catatcaaag acactagaat tattctagtg   25860
ccgcaagatg aatactctaa tgacaaatat tcttatataa agtcatttt gaaatttatt   25920 tttgtgataa tatgtncata gttttggcta tttcaaatct attatcaaat aataataacg   25980
wwnwggcaat gcaaaacaag aatttttcgc atggtgccaa ttgatcnaaa ataatataga   26040
tttaaagtcn aagaacttct aaggtgaagg gcatatttg tcaaatttac aatgcatgag   26100
cntacgtctg caccgtctgc acacatacag ttgtctgcta gcactttatg cgttgaaacg   26160
```

```
agctgttcgc tgtagcgctc tccgctctct cgctctctac caaaaattcg agagagcctg    26220
gagccacggc gaaaaaatcg tgtgccaaaa aatcgtatgg cgttacgcat cttgttattc    26280
taaggtcttt ggaggggtag tgttgaagca gtattcaaag tattgaagcc aaatgtccca    26340
atcagttttg gatcgtatat atttactaag agttctatgc cttctttcaa ctactccaac    26400
tgtctggtaa tgatntgtta taatttttaa tgatatattt tttatttaa agtgttttat     26460 tcacagatca gatattacta aattcttatg tctgttccca tgtccgtaat gaacgttttt    26520
attggaccgt acttcagaat aaaagattca aatatcgctt tggctacggt atttgcattt    26580
ttgtttggta tggtatggct actaagtatt ttgtcatgtc acatatgaga gtgactgcat    26640
atatgtacat taccattttc cgattttggt agtgggccaa ttgtatctac aaccctatca    26700
tatgcctgtt ctagtgtttc atttatcgtc attggtgttt tgatatgtgt aattattttt    26760 gttttttggaa cgatggaatt tttttgtgta ctcttttatg tacttagaca tattttccca   26820
aaaatacaat aatatctttg caccttgacc aaggttttg aaatgccagt atgtcctcct     26880
catcatgttg tgtagacgtt atagcttctt tttctatttt ggtcaccggg ctgagtagcg    26940
ctactcttaa tacgttaat tgttaatttt aattttaatt tttcattgcc cacatttttg     27000
aaagtctatc gaaatatttt caaagttatt ttcccacggt gccatttaa ctgtcttgat     27060 tttgtgtata ccggcctggt tttcaagcct ttggaaaaac tgatctaaat cgagatttcc    27120
aataggtaca aatcaccaat tttataactt gcaatgtttt tctttccatg tttgaaaaaa    27180
catatcatat ttttcagatt gctaatgaat gtaaatacgt tgggctttga ggtttttatt    27240
gattactttg gcaattctat ttttcatt tcttctcttt cgcaggaatt ttgtctacat      27300
tgatatctgg tagtgagtat aggtattttt cggtttttat tttttttctca ttgaaactag   27360 gtatgttaaa ggtctctgtg gtcactttga actaaaaaat gcctaccata tacagtttgt    27420
caagaaactg tttacacact gtgaaataag ttgaattttt gactttaaag ctaaaaataa    27480
agggtntttt gcttaattaa acgcaattt tttataaaat ataattaaac aatatttatt     27540
ntacttataa atnaaaacac aaattaaaaa tattaaatat acnagaaaat aaacaacana    27600
ttccaagttt acacactttt gagactgtca agaaactctt tacacaaaac actaaatcga    27660
agtttaatcc taaattttt aattatytta ttaaaatttt aaaagttttng gtatgtarya    27720 tgtttccccm ttkgctttag ctacaagttg aagccttttt ttcatggatt ggacaagttt    27780
ttgcaggtca tattcaaacg ggatctttc acactcttcg actattacag tcataagctg     27840
ttgttgtgtt ttaggtccct ttttgccacc ttcttcttta agtaggtcca caaattttca    27900
atggggttca gatcaggact ctgagggggc gtatcgatca ctttaccaca gttattaagg    27960
cgccaggtgc gtacattgca ctctttatgt ttctgatcat gtcctggtaa aacttaagat    28020
ntggcttgtt gttgctaact agaccgaatt tttntgcact ggccttcaca tttgtttttt    28080 aacattcta gatattgcac ggcagttatt gtgctctcaa ttaaggctag ttttcccact     28140
ccacggctgg tgatacagcc ccaaaccatc agtgacattt ttccaaattt tatcgttgga    28200
atgatatttt gttttctag cgcactcaac ggtttgcgcc atactctgct ggcccgtcg      28260 ttataaaga gcatcatttt tgtttcgtca caaaatatga cgtcatccca gtactcttcc     28320
gcatgatcca tcatgctcac agcgaattaa tgaccgcttt tccatattgg catctgatag    28380
caaagggttt ttccttgcaa atcttgaaga gtacctatgg cgtaggatga cttggcgcac    28440
agtttcgtgt gacacagtta ggtggcattc ttgcctgata tccagagcaa gtgatctgac    28500
cgagattggg gggtcgcaat cactattcgc ataataaagc ggtctacacg ctttttaatt    28560
```

```
ttaattttcc gcccaccacc actcttaggt tcaagcctgc cctctttttc cgagccttt   28620
aaaacattgt agacggtctt acgggataca ggaaacattt atactaattc tggaaaagat  28680
tttcccaact ggtggttata gtttattaat tgggtaactt caaaagttaa tctctttcca  28740
ngcattttat taaattaata attcgcttta agcacgtttg gatcaagcaa aatttcacaa  28800
gcaaaagtna caaaatttna atagaagcgt tgtaaaaagc aatgcaaagc caaaataacc  28860
gaaaaatcga gttcgttcta agaaaaagaa cnaacaaagt aggaaaacaa atgtggtaag  28920
agtttcttga cagtctcaaa agtgtgtaaa cttggaattt gttgtttatt tcttgtata   28980
tttaatattt ttaatttgtt ttttgattta taagtaaaat aaatattgtt taattatatt  29040
ttataaaaaa attgcgttta attaagcaaa aaaccctta tttttagctt taaagtcaaa   29100
aattcaactt atttcacagt gtgtaaacag tttcttgaca aactgtatat gtgtcggcga  29160
gacagcagtt tcagccattt catttattca cttcgcgatt ttgtgcgtca gcgcagcaag  29220
ttccgatcga cgtcagcagt aaaacttcac tgaagggatc ttcttacatg tcccttcttc  29280
atcatattct ctaatgtcta tacacactgg cgtgtgccac attgtcatct cgttctaaca  29340
cactatttat gaccactcga tcggacctca ctcagctgca gaggctgttc gtgcctctgc  29400
cgcagcgctc gacagaattt taccgcaata ttacaattcc atcagaatat gaaatcacag  29460
aaggaatttc tggaatgcga aaagtcgcgc tccgacacgg ccttcctgac ctttcacacg  29520
tcctcgtgtg cctaatccac caatcaagtc caagtcacac aacttcgtca acttaagaac  29580
aattaatgac nacnagtaat aatcagtaat tatttaattg gcaattcatc tcatgactgg  29640
ttttcttttc caaggacat ttccatttac atatcaaaac tttnaactat ttaccatttc   29700
catgacttta atttctcata ataacattgg cgtggcttct ttnacaccaa tcttttttgcc 29760
ccggcataac acttttggcc ctgcgagtta gctggtatag tgcagtcatc atctcttgan  29820
tnccgccata acacttctcg tccnggcgng ggagctgtta tagtgcagnc atcatctctt  29880
gaccccccgcc ataacacttc tcgtccctgc gagttagctg ttatagtgcg gtcacacgcc  29940
attctattca tgacgttcgc caaatgttnc ctttcttggg cacgatcact agtgccatct  30000
ttaaactctt ttccctcttg gacacagat gtacgatcac tagtgccatc cctcaactgt   30060
tntctctgnt gggagtcacc attacattca tgcgaatatt natatgtncg cttgataact  30120
aacgacttca aattgngtcg atgaccatct agtacattaa tcactcgatg atactcctca  30180
cttaacacat gaactcatac cgaactacta catccttcg cttggcnncc ttgcttgtac   30240
gctcattngn tnncaacctg cccattngct ctgctggcat ctgnagctat tgaaaacaac  30300
tcaatcctgg nnggngaaca aaactcacgg aactngntgc tgacaaagct nctgccttga  30360
tccactatga tgcgactggg agctctaagg aaagacatac tngactcttc tatagaatcc  30420
gctggccatg ttaaaccaaa ngaaaaaaaa tntttcccnc nccgcaaacg ntcntttgat  30480
ccaaaatcca ggaancaatg gaaantgagt cgatatgggg cgcccttgac cacttttnatt 30540
tttaattact ttaaacgaat ttccaatgcg cnttatttgg tatcccagtt acgaaactat  30600
cggcatactt ttccaatata tttcttaatt acatttatca ttatcgctta cttctgtatt  30660
gatgtcaaaa agttttttcca aactattctc atgtgcatta ttttgaacgg cattgataac  30720
tttggatttg tacatgctaa atttattaga tttaatcaat aaaacgaaac caagctctaa  30780
tatgtcttgg ccaatcatta tgtcgtactt taaatagttg tccactacaa catgaaacaa  30840
aatatctaaa ttcaattgag acatttggac tgtttatagt atttgcaagt ggctcttaac  30900
```

-continued

```
tacattgtca ccaattcctc ttaaaacaac taggttatta attctcttgc cagccaattt    30960
gttacttaat ttatccttta ttaaagaaca ttcggcgtcc gaatcgaaaa aaaaatgaaa    31020
agggctcacc caattgaaaa agtggactgt tttttcaatt gggtgagccc tttccatttt    31080
ggaaggaggc aggcaccaca atgtcattaa cgtctgtgaa gtttacacta gggcagctga    31140
aatagtgaag cttttacaa acgccctgat actccagaga gtcctcagct aggttcaact    31200
tgactccggc ctgtgttaac aggtctaggc ctataatagt gtcgaacgag ttgagcgaat    31260
tcaataggaa gaatggggag gtgtgcttga ataccttcat aaagcacttt tgcttgattt    31320
cggtggagcc atgtattgag ctcaccgaga acggactggc gaccggcatt atattttta    31380 gctcttttac ggacttaatg taattatttg ccgcgccggc gtcaattaac atctttaaag    31440
ttctcccagc caaccgtcgt cgcttgaagc gttctcattg tcactgtcga tatcctcgac    31500
tgcagccttt gctgcattct catattcctg cttggggtct tttgcgttag ggtctttagg    31560
cttgggattt tcttgacaa cattattgat gcgctggcgt ctgggacctg tcgaacggtc    31620
tgaggaattt ctcccttat aagtattggg cccattttgg ttattcctat tgtattcggt    31680
ccgctgtctg aacctggatg acgcgtagac ctccatgggc tgangtgctt gcgcctggtt    31740
gtcattatta ttctgcggaa tggtattacc ttttggtcgc cagacaaagt gcgtgcttct    31800
ctcctggcgt tggtctctcg ntgtcttcc cttgtctacc ctggaaacng ctcttgccgt    31860
tgcgctcgtt cctctatacc ttggcgtana aactcgcgaa catgctcctt tcaatgcttg    31920
cttncgcttn tttggccaaa ccnaggcana tgcaagtccc tgggtttagc cgggaagacc    31980
acagctctaa gggacttttt gaggcccgnt ntggnggcat gcagggcatc ggctcttant    32040
tcagcgttca gtaagtcagc gccctcttgc tcgtgtgtca tcacaattt gttggtgacg    32100 agcgtcaatt ttttttcgac ttcgtcgtag tattgcatca atggcatgtc cccttgcctg    32160
accatctcta atacctgcct cagtaggcgt acggatgtct tgtctgagta cgtgcagtct    32220
aacctagcca aaatggcatc gaaattcaac ccagtattgt gagatagtag tagggctcca    32280
gctgcgcctc gaattttgtt tcgtaggatg gctacggctt ggtaatgagc actggtaccg    32340
ttacagggct tgaataggc gtaagcgtat atggcccgct tgcctncagg cttngccaag    32400
acaattgggc aacagttaaa actcttcatt taaggtccct aattactat ttatttta    32460 tagtgtttgg taattcctaa gaatatttct ccaccctgtg atgttaagat acaaatatga    32520
tgtacggatt cttcacttaa taaataataa ttttaaaaaa aacttgtttt ttgcttttcg    32580 ttttatttt tttttagag acacttgatg ggcagccgag taaatagctt gtcaaactta    32640
catgttctgt agcgtaacta ccttgttgac tatttgcggt ccttgatgaa gttgggcgtt    32700
atgtagatat gcatttctct gctgtgtcca gagttatgta agatatgtat ttctcttctg    32760
tgtccagagt tatttctctc ctgtgtccaa gagtcttcct tctcacactc caaatgggac    32820
acgtcggact tctacaatcg aacggtctca gcatagagcg ctgaactcca ttatggcgcg    32880
tcagcattac tttgcgtggc tacttagttg ctaagggaat gtgaacttga tggtttgtta    32940
acttgtatgc aaaattcttt gctaaaatct gggtactgaa gaagtatagg tttcattaat    33000
tcccttttaa tatacttaaa tgcgtggcgt gattttctc taacattttg atttaatctt    33060
ctataatgat tataaaatgc aacgaatcgt ctagcttcgt ctgcatttgc tggtttggga    33120
tagtttttga ttacgtcgtg acctaaatat gtaaccttt ttataaggga agtacatttt    33180
tctggatgga gttttagctt atgctgtatg cataatttga atacatcggt taagttcttt    33240
accatatgcg tctcagaaca accgattact acttaatctt ccatttataa aacgcttgca    33300
```

```
aaatttgtaa gcatgcgaac gcaagtgtca tcattctttg taaggaattt ggtgctattt   33360
ttaaaccaaa tggcaatcac gtgtagcggt attcacctgt tgaagctgag aatgatgtta   33420
tattacttga cctttcttct aattcgattg aatgatcaag aatatcttct attcttggaa   33480
gatggaattt atctgctagc aatttcttgt ttacttggcg atagtcaact actagtctcc   33540
atcgcttttc cgccgactta ggcattgact tctgggtac taagagaggt gggcttttat    33600
attctgatac agatggtgct acaataccct cttctatcaa ttggttaact tgcctttgta   33660
ttcctggctt acgactttct ggcttttat  agtttttat  gtgcttctgc aaagctttgc    33720
cttctttgtc ttgtgtgtcc gtgacaacgg acaacgtgcc ggctcgaatg gaattatgat   33780
gttatcgtcc ccgggttaag acaacgctcg gcctgggacc acctttgccg accactgact   33840
ccactgtccc tttcaaacac tacaggtccg tgtcgtgtcc tccgcaggac cacctgtggg   33900
ctgaaatggg ttcaggatgt tatgtggcag ggtgtgtcgt ctacgggtta aggtaacccg   33960
taccacctca gcctgggacc acctttgctg acactgactc cactgaccct ttcaaccacg   34020
ccaggtcctt gttcttccac tgcaaggatc gatctccacc tcgaattgct cgtccttatg   34080
tgtgctttcc gacactttct gctgtccaac gctttcacag ttcgctcttc actgactcct   34140
cctcgcgttc taactcattt tctccttcgg acgtttagc  atccacctttt agactgcgtt    34200 cctttcgtc  cggtactctt ctcgactgtc cttctcgctt gttgggactg gctgcccga    34260 gctgcacttg cgtcgtccct ttataggccg cgggatcccg ttatttcccc ttttgcgcaa   34320
gtctcgattc caacgcggta ccggtagttc acgttctctc ctcaatgccg gggttcaagg   34380
tccattaatt accgttcaac ctgaccgacc ttgactcttc ttgcattcca gccgtcttca   34440
ctgctgctag gccgctcccc tgcaccggaa tttgtgggga gttttaagac tctttacaaa   34500
acatcgatct ttcatatgac ttcagatctt gcaggcagaa ttaatttatt ttcaaaagaa   34560
tttatacgtg tatacgtgtt tatgttcctg atgttattgg gccctactgt gaaccaatca   34620
tcctggtctt ggaatttcaa aatacaagtg tacttcttta taaagcccaa gccaaatata   34680
ccatcacctg gtgtatttta ttgattattt ctgcacttta ggagtaaaat atcaacacct   34740
ttatctatta atgtcaacat gaataatttg tccggggtat tttggctagg gggtttcttt   34800
tatttctgga tgcgtggaat gtctgtcata cttagcagtc ttacacacca aacactgact   34860
cgcgatagct aaaactttt  cctcatttta ggaatgtata ctctttcgga caactgagct   34920
ttattttcca cagcatttct gtgtgctctg ttatgtgtcc taagtatttc ttcctcttgt   34980
tcggcttcgt taacaaggtc tttaacttta gtttgacaga atctaatctt gaaaccctga   35040
aaatggatgg ggtagagaat ttgtatttc  cccattacat cctcagatgt gaaaattcca    35100
ttaatcacgg atgggttaag atattccttc aaatctgaca agagactatc aggtgtgaac   35160
aatttacgat ctactaaata cctatcgaat gtagggaatg gaatgctaaa tgagtaattc   35220
tctgactcgg acttcctgaa gaaaatttga tttttaaatg catttatcgg gatttgaacg   35280
ctacgtatca acccatggct cgaactgtcg gagctgtgca ttggtaaaag ctactgtgtt   35340
aatctgttcg actgtcggtc ctttggacaa aacgtcgggt acagtatttt ctttgcctgg   35400
cttatagaaa atctcgtagt catattcctc aaggtatgct ttccatcttt taatcctcgc   35460
attctcaatc caactactga gagaatggtt cagaggctga tggtctgtaa agattttacc   35520
tttgctttac cggaaaggta agttttagc  ttttttagag cccagataag aagaatctga    35580
tgaaacccac ttttcagatc gagcactgag aaaatcttgg tgctccaatt gtgccaacac   35640
```

```
ttcattaatg cagggatatg gtatctgtac gctactggta ccatattaag tttccgggag   35700
tcaattacca ccctggaatt tttctctttg ccaaaaggag tcgagttttt tttggggaca   35760
atccacactg gtgaatgatg ggacctgagg tcgaatgatt ccatcgggta aaagggtcg    35820 aatgatcgca tccgtgtaaa agttcggaaa tttgtttgtg tacctcgtct ttaagagaca   35880
ttgggtactg atagaatttt gagtatattt ggcgtatccg atatagttcg gattgctgcc   35940
cttacacttg ttgtgtaggt tagttttga ttcgggtctg cgaagagacc tgaatacgat    36000
atcaattatt ttattcaata tcattctctg ttccacctct aagtgtttta ttctcggact   36060
aattgtgcta acagcctcga actgttttc tttgagaaca actctttcc cgttttccag     36120 tgtcatggtt aggttcttca atcaatttg cgctcccatt ccttcattg tgtctttgcc     36180 aagtatggcg tcaaaagtct tcagcgttgg taacaaaaaa aattttattt cgaaatcgaa   36240
aaaaaactct tttgtaatgc gatattttta catcaccgcc tggagtatca gctatgtaag   36300
gcttgttatt tggtatcgcg ttcgtcacca aattgggctg gatgtaattt ttattagagc   36360
ctgtgtcaat caacacccctt aaaacctttc cactccccac tctacattcg aagtatggta  36420
gtgaggagtc ttcctactcta aaaaatgcaa cacgtggtct cgttgttcgc tgtccaaatt  36480
gtctatttgt ccatcacagt attcatttag tgtgccgttt atattgttct gggtttcata   36540
atcttgcatc gaccgttgat agcctgtcat gcttgaactg gacccagtta cttcaatact   36600
tggctgtctc atgttcactg tttggatgtt gtagttcttt tgtcgtttgt ttatgtccga   36660
gtgtggtcta ttcatataat taatgtttcg cgtctgtaca ctgccgtcca cgtcccattg   36720
gttctggtct tggttgtggt ttggtcgcaa agggacgggg tggggcattg tattgttgcc   36780
attgctgttg atagttttgt cggggtggaa tgaacggtgc attaccgaag ttagacacgt   36840
gttgccttgg cgccgggaat ggctggccta aatattgtgg aggtctcctc atgggatgtc   36900
gtggagggac cggtggaggc tgtcgatnnc caaaggcatt cgacggctga aaattgcggg   36960
gtgccggaat gggttttcg tttcctctga aactcgactg ttgacccctta tcgccgcat    37020 gggttggtga cctgaanagt ttgattttca agtttaaggc aataatgtaa agctgagggg   37080
agatcagctg gctcttttat tgccaaannn cgaggtaaat ctcctcgaag gcctctgata   37140
aaagtatcca gagcttttc tctgtacatt tttgtaacaa agtgctcgga ttctcggctc    37200
atttgcatgc agccgacttt atttagaata agcgacagat ttttgtagac gtcttggtgg   37260
aagtcttcca ccgactgctg gtggccttga accaaagttg acatttggta ttccaaggta   37320
gttatgtccc gtttatctgc gtaatgcaga gtgagacatc tcgacatggc cttccagtcc   37380
agcggaatgc tgtaggactc gagtgccaca tcagcacttc caacaatttt atttcttatg   37440
gtatgaagta taccataata ttttggagta cccacaaatg gggtataagt ctccatgatt   37500
ctatcaacgc tctttttcca agacccgaat tctgctggat ttccagagaa ttccctgatc   37560
gattttacga tatcaggcac cctgtcaaag tccgctaaat tatttctgta ttcgggctcg   37620
ccgacctggt cgcaccttga tgctcacgta cagaaagtca agagtatcgt tantcattgt   37680
tttatcagcc cnggtaaact tggcccncng tttgccaatt aatgctgtct actgtnngac   37740
actcatgtct acgcgatgct gttcagncca ggtcgggtct tttctgaggg taaaggtctt   37800
ctcatttgaa ctgaaagctg agggtcttat tatattatta gggtttncca tgtgggcttt   37860
aaattcgggc ccaaaacntg cataaaacaa gcntaaacct aaacaaattt gaacttaaca   37920
aaagttgtgg gcagaaaata tggaatgcat ttgcttactt ttctttcgtt ttttttttta   37980
attttgcgtg caataataat ttagcttgcc gcggcaattt tgctttcaga gcattgtacg   38040
```

```
agaaaagaat tgtttctttc agaagatctc taggaactgg gttgaaaata taataaaata    38100
atattaccaa taataataat ataataataa taatataata ataaaaatat aaaaataata    38160
atagaataat aataatataa tataattata tatatatata tagtgacata tccataagtc    38220
cctaagactt aagcatatgc ctacatacta atacacttac aacatataca ccccaataca    38280
acatacacta ctccggatgt acccaacaga tccagaaaga ataagattgt taaaaaaacc    38340
ccattctaga taagtcaccc tggtagacta acatccgcc cctaatttaa acaattcctt    38400
gcttaagcct caccccatcg tcacattccc acgttcaatg ctcggacccg aaatcccgaa    38460
aaacaaaagt atcgatttca ataaacaaat tataagaatc taagagcact tgtatccaag    38520
agcaaatgca cttgaatcca agagaaacgc aaagctttt ctcttcacga tcagaatcct    38580
aaagtctaaa gtccatatta gaaaagctcg ataccgaggc ttgaacgtca atcaaatcag    38640
aataattatc agagttcagt ttgagaccta attgtaaaag gtcggtgttc ttctcaaata    38700
aaaagattgt aatcatttag tgaaataaaa attatatttt tttcacttat aaatattgca    38760
agtatttaat tatatataat atatataata tatataataa tatataatat aatatatata    38820
tataatatat ataataataa tataaaaata ataatataat aataataata ctataataat    38880
aacaatataa taataataat atagtaataa taatataata ataataatat actntatttt    38940
tttgntatac ttatttttta tcatgggtgg atgccagaat attaaattgc tgttgntgnt    39000
gntgatgata atgtcgctgt ggtggttttg gtactattgg nttcttctga ttcggagttg    39060
tcgctagctc acttttgtct cccgacttcg agcgtgttta aattttaata ttttttcctgn    39120 gtacttttca ggttcntggc ggctctcccc ttcttcttct gntctttctc tggcttctct    39180
tcggtggggt caagcttcag cttctctaca cacagcctac tganctagaa taacannact    39240
ctccgcagat ggaatttaaa gcaatacaag nggtaaatgg ggattaatat cctagaggna    39300
tgctatgaat aaccaaaaaa tcaccncact acaattttgt caaatcgata gttccgcaag    39360
tttccaagcc cagactaaca agttaaaaga agtgctttgg aattatcaat cacaaagaat    39420
ctaaacatcc taggagcaca tccaagaggg ggcgaanntt cacttgaagt tccgagacaa    39480
ctggaagttc cataaagctc aatttacaac ggccttcaaa agctcattag actaaagtnc    39540
caaagttgat attcaaaagc tagagaacga tacttgaacg tcaatcaatc tgatcaataa    39600
gttaagttca gtttgagacc taaataatgg ttttaaaaaa aagtgatatt tttatgaaag    39660
attgcaaatt gcatatatat atatatatat atatatatat ttagatgcaa actcantgca    39720
tttgggaatg caataaaaat aactaagtta attttttaaat ttgtcaatac gaaacacttt    39780
taccagtata tatatatata tatattttac tattaacaaa ttaagcaaac acgatatttt    39840
ctacagtgga ttgcaaatgc atgaaggaag gaacttaacg gttaaacggg aaacaaccga    39900
aattttgccg cgcgtgccaa aagagtgtcc atatttttaa gatactaatt taaaaaaaat    39960
tacatggaga tatatatatc aaacgtggac gattcggcgt gatccataac gactttttaaa    40020 aaattcttaa ataattggaa atcaatatat atatattctg acgtatttgg tccaaccacc    40080
ggcacttaaa attatttcag gagaccctat aaaaaacagt ataataaagt aatcggagct    40140
gcggcagctc cgtttaaaac tcgtttgaat gtgcagcgcg gcctcagccg ttgttaaaca    40200
tttatccctc gggggactttg ttanctctgt ttcanaagtt cctattcaat ttcggnaatt    40260
cttttaccng ttggnattgt tagatccngn aatcttttc tttgaaatcc tctggtaatt    40320
catttgggtc attattaaga tagtattaga ctatcaaaat tgtaggtccc gatatgtcca    40380
```

```
aataanaggg gtttattgtt tattttgtgg taatattggc gtgcttcggg taaacattct   40440
accaatatat gtataggcag gcgtgctnat ttattgtgtc tttatgtaca aacnngtctg   40500
tgtgaaacat ttgtatgacc ttatcgtttt ggtaagatct tttattaata tctgccagtc   40560
caattatatt gcttaataag acataaatca gaggtgcagg gcgggactac taatattcct   40620
cttgtcgata gtgggtattc ttcctttacc agtatatttc gttttttat tttttttttt   40680 ttattttat attttattca tgatttacaa tttaaacctc ttaatcattc atatcatatt   40740
ttactttttt taggaaaatt ttaattttta caatttctac catagtttat ggtgcctttta  40800 tttttccttt taatttccaa acgtagaatg agaccaggat gttttaactt caatctggct   40860
tactgttttt tgcctaaatc gatgagaagc gcttccggct tagcttgcag cgaatcggct   40920
tatacatatg tatagtgaca tatccataag tccctaagac ttaagcatat gcctacatac   40980
taatacactt acaacatata cacccccaata caacatacac tactccggat gnacccaaca   41040
gataccagat aagaaaaaga ctgttatacg atcctcgaga atagaaanaa ccccaattct   41100
agataagtca cccactggta gactaaacat ccgtccccta atttaaacaa ttccttgctt   41160
aagcctcacc ccatcgtcac attcccacgt tcaaagctcg gagccgcaat cccgaaaaac   41220 aaagtatcg atttcaataa acaaattata agaatctaag agcacttgta tccaagagca   41280
aatgcacttg aatccaagag aaacgcaaag cttttttctct ttacgatcag aatcctaaag  41340
tctaaagtcc atattagaaa agctcgatac cgaggcttga acgtcaacca atcagaata    41400 attatcagag ttcagtttga gacctaattg taaaaggttc ggtgttcttc tcaaataaaa   41460
agattgtaat catttagtga aataaaaatt atatttttt cacttataaa tattgcaagt    41520
atttaattgg cgcagtcggt taggatccaa taaaataaaa gagtccttttt agtacggtac  41580 tgatcaactg aaggatatgc tatacgacta gctatccaag atcagcgaat taaaatagtg   41640
attcaaaaat attttttaat ccgcaaaaga atctacgtga aagtagtatt caaaataaaa   41700
tcccgtgcgg tcggaaacaa aaattaattt aaatttttta attccgaaac ttaaaaccaa   41760
gtttaaagaa aacttaaaat caagaaaact taaaaccaag tttaaagaaa acttaaaatc   41820
aagaaaactt aaaaccaagt ttaaagaaaa cttaaaatca agaaaactta aaaccaagtt   41880
taaagaaaac tcaaaatcaa gaaaacttaa agccaaaata agctagaaaa ctaaaagaca   41940
tcatggcagt cccacaactc tcagaaacac acctaaacca actgctaaac caaatcaaag   42000
aattaaacta ctacgatggc gcacctggca aattatctgg attcgtcaac caagtggaac   42060
aactgctcag tttataccca acacaggaag caagacaggc acacgtcata tatggagcag   42120
tgaagcggtt attagtggat tcagccttag aagtcgtaac ccaggaaaga gctaacacat   42180
ggctggacat gaagaaagca ctggcaatgg cattcaaaga ccatagacct tatgtaactc   42240
tcatcagaca attagaagac atatcatacc caggaagtat ctgtaagttt atagaaaaat   42300
tagaaacaca atactggatt atgttcgata agttagaatt agaagtgac catgttgata   42360 aatcgaatta taccgaaatg ttaaacaaaa ctgttaaatc agtaatagat cgaaaactgc   42420
cggatagaat ttatatgtct ttggcacgta agatattga tacaatttat aaattaaaac    42480
aagcatcaat ggaattaggc ctttatgatg ctattccaga aaatcaccgt tctaatagaa   42540
cagaaatgaa taaacgtagg aacaggggaa actataatca aaataataat caaaatatt    42600 acaataatag aaatcacaac tacagtaatt attatcctag catgaatcag aatcataata   42660
cacaaccacc tcagaatccg actcaaccta tgacaaatca aaaccaatat tcaccgcgtt   42720
tcataccgaa taatcaaaga gggaattatt atgcatttag acgagactta acacaagctc   42780
```

```
agcagaacaa cccacttaat aacacccttg acttccaacc ttcgacatcg aataatatta   42840
acagacaagg gccagtaaaa agacaacgcg agagtcagag tgaccaaagc aggatggatg   42900
taaattttca tcaagctgcc tcggacactc aaatgataga gaaggacata caagtccctg   42960
tgtaaaaata attcatcata ataaaaatta taagggaatg atcgatacag gatcatcaat   43020
taacatcata agagaaaatt ttgagaactt agaagaaaag gaagaaaacc taatagtata   43080
cactattaaa ggaccaataa cactaaagag aagtataata ataaaaccta cttcagtatg   43140
tccgtctgct caaaaattct acattcacaa attttctgat aactatgatt tcttgttagg   43200
tcgaaagtat ttagaagata caaaagctaa aatagattat gctaacgaaa cagtaacact   43260
aggctcaaaa gtatttaagt ttctctatga agaaaagaag ggcgagaccg catccaaatg   43320
ccttgaccca caagaaaaga atgattccgc tctagtggac agaaccaaac caaaaatgca   43380
aaaggttaag accgcaccta agtgccttaa accaaagcat caacagcaga agaaagagac   43440
cgcattaccc aaatgcctca tttcaaatgt tgttaaagac acagtggaca atgatgtaac   43500
acatctcgat cccatgtccg ttgacaacga tatagtcaac ttcgcgatta caatgagtt    43560 acgcgaatgt aacgagtata gactcgaaca cttaaatgca gaggaagttg aatgtttaaa   43620
gaagttccta tacgaatata gagacattca gtacaaagag ggcgaaaatt tgaccttcac   43680
cagtactatt aaacatgtca tccagactca acacgaagac ccagtatacc gtaaacccta   43740
caagtaccct caaagcgttg accaagaagt taacaaacaa attaaagaaa tgatagaaca   43800
agggattgtt cgcaaatcga agtcccctta ttgttctcct atttgggtgg tccccaagaa   43860
ggcagacgcc tctgggaaac aaaaattcag gttggtagtc gattacagga acctaaatga   43920
gataactgtt aacgacaaat ttcccattcc ccgaatggat gagatattgg acaaactagg   43980
tagatgccaa tactttacca ctatagatct agccaagggt tttcaccaaa tccaaatgga   44040
tgaaaattct attgcaaaaa cagcttttc aactaagcat gggcattatg aatatactcg   44100
tatgcccttt ggtttaaaaa acgctccagc tacttttcag agatgcatga ataatcttct   44160
ggaagattta atctacaaag actgtttagt ctatttagac gatattattg tttattccac   44220
tccattggaa gaacacattt tatccctaaa gaaagtcttt gaaaaactga gagacgctaa   44280
tttaaagttg caactagata aatgtgaatt catgaagaaa gaaactgnca aaaactgtca   44340
caaacccgac agttgaccct tatttgccgc atggtttgac ctgaaagttt gatttcaag    44400 tttaaggcaa taatgtaaag ctgaggggag atcagctggc tctttattg ccaaaaggcg    44460 aggtaaatct cctcgaaggc ctctaataaa agtatccaga gcttttcaa cattttcta    44520 acgaagtgct cggattctcc gctcatttgc atgcagccga ccttatttag aattagaaa    44580 agattttgt agacgtcctg gtggaagtct tccaccgact gctggtggcc ttcaaccaaa   44640
gttgacattt ggtattccaa ggtagctatg tcccgtttat cgacatggcc ttccagtcca   44700
gcggaatgct gtaggactcg atgccacatc agcacttcca acaatttat ttcttatggt    44760 atgacgcata ccataatatc ttggagtacc cacaaatggg gtataagtct ccatgattct   44820
atcancgctc cttttccaag acccaaattc tgctanattt ccagagaatt ccctgataga   44880
ttttacgata tcgggcaccc tgtcaaagtc cactaaatta tttctgtatt cggntcgatn   44940
acctgatcgc tcacgtcagt aaagtcaaga gtatcgttat tcatttgttt tatcagtcca   45000
ggtaaaactt ggaccaccgt ttggccaatt aatgctgtct actgttcgac actcatgtct   45060
acgcgatgct gttcaggcag gtcgggtctt tctgagggta ccggtctctc atttgaacta   45120
```

```
aaagctgagg gtcttattat attattaggg tttgccatgt gggctttaaa ttcggacaac   45180
acctgcataa aacaagccta aacctaaaca aatttgaact taacaaaagt tgtgggcaga   45240
aaatatggaa tgcatttgct tactttttctt tcgttnttttt tttttaaatt ttgcgttgca  45300 ataataatttt aagcttgccg cggcaattttt gctttcagag cattggtacg agaaaagaat 45360 tgnttcttttt agaaganctc ttangaactg ggttggaaaa tataataaaa ataatattac  45420
caataataat aatataataa taatnatata aaaataataa tataataatn ataatataat  45480
aataaccatt ttannattat taatttnnna attatnattt attatattat aannttaata  45540
atttggnaac ctaaggntaa tatgggggg tggatgccag aatattaaat tgctgttggt   45600
ggtgnnnntg atgataatgt cgctgtggtg gttttggtac tattggttct tctgattcgg   45660
agttgtcgct agctcacttt tgtctcccga cttcgagcgt gtttaaattt taatattttt   45720
cctggtactt ttcaggttcg tggcggctct cccctcntct tcttctgtct ttctctggct   45780
tctcttcggt ggggtcaagc ttcagcttct ctacacacag cctactgatc tagaataaca   45840
ctactctccg ctgatggaat ttaaagcaat acaaggggta aatggggatt taatatccta   45900
gaggatgcta tgaataacca aaaaatcacc cactacaatt ttgtcaaatc gatagttccg   45960
caagtttcca agcccagact aacaagttaa aagaagtgct ttggaattat caatcacaaa   46020
gaatctaaac atcctaggag cacatccaag agggggcgaa attcacttga agttccgaga   46080
caactggaag ttccataaag ctcaatttac aacggccttc aaaagctcat tagactaaag   46140
tnccaaagtt gatattcaaa agctagagaa cgatacttga acgtcaatca atctgatcaa   46200
taagttaagt tcagtttgag acctaaataa tggttttnaa aaaagtgata ttttttatgaa  46260 agattgcaaa ttgcttttta taaaaaatat atatatttag atgcaaactc antgcatttg   46320
ggaatgcaat aaaaataact aagttaatttt ttaaatttgt caatacgaaa cacttttacc  46380
agtatatata tatttttttta ctgattaaca aattaagcaa acacgatatt ttctacagtg  46440
gattgcaaat gcatgaagga aggaacttaa cggttaaacg ggaaacaacc gaaatttttgc 46500 cgcgcgtgcc aaaagagtgt ccatattttt aagatactaa tttaaaaaaa attacatgga   46560
gatatatata tcaaacgtgg acgattcggc gtgatccata acgactttta aaaaattctt   46620
aaataattgg aaatcaaatt atatatattc tgacgtattn ctggtccaac caccggcact   46680
taaaattatt tcaggagacc ctataaaagt ataataaagt aatcggagct gcggcagctc   46740
cgtttaaaac tcgtttgaat gtgcagcgcg gatcctcagc cgttgttaaa catttatccc   46800
tcggggactt tgttanctct gtttcanaag ttcctattca atttcggaat tcttttaccn   46860
gttggnattg ttagatccng naatctttttt ctttgaaatc ctctggtaat tcatttgggt  46920
cattattaag atagtattag actatcaaaa ttgtaggtcc cgatatgtcc aaataanagg   46980
ggtttattgt ttattttgtg gtaatattgg cgtgcttcgg gtaaacattc taccaatata   47040
tgtataggca ggcgtgctna tttattgtgt ctttatgtac aaacnngtct gtgtgaaaca   47100
tttgtatgac cttatcgttt tggtaagatc tggtatcttt tctntgaanc ctccntgtaa   47160
ttcattttgg gttcatttac taagatagtt attggcctat caaaaattgt aggtnccgat   47220
atgtccaaat tatnnggttn antgtttatt ttgtgtagaa ttggcgtgct tcggtaaanc   47280
attctccaat atatgtatag gcaggcgtgc ttattatntg tctgtatgta catacctgtc   47340
tgtgtgaaac atttgtatga cttatcgttt tggtaagatc ttttattaat atctgcccag   47400
tccaattata ttgcttaata agacataaat cagaggtgca ggcggactac taatattcct   47460
cttgtcgata gtgggtattc ttcttttacca gtatatttcg gttttttttgt tttttttttt   47520
```

-continued

```
ttattttat attttattca tgatttacaa tttaaacctc ttaatcattc atatcatatt   47580
ttacttttt taggaaaatt ttaatttta caatttctac catagtttat ggtgccttta    47640
tttttccttt taatttccaa acgtagaatg agaccaggat gttttaactt caatctggct  47700
tactgttttt tgcctaaatc gatgagaagc gcttccggct tagcttgcag cgaatcggct  47760
tatacatatg tatagtgaca tatccataag tccctaagac ttaagcatat gcctacatac  47820
taatacactt acaacatata cacccccccn accacataca ctactccgga tgtacnnaac  47880
anataccaga taagaaaaag actgttatac gatcctcgag aatagaaana accccaattc  47940
tagatctaga taagtcaccc actggtagac taaacctccg tcccctaatt taaacaattc  48000
cttgcttaac cctcacccca tcgtcacgtt cccacgctca atgctcggac ccgaaatccc  48060
gaaaaacaaa agtatcgatt tcaataaaca aattataaga atctaagagc acttgtatcc  48120
aagagcaaat gcacttgaat ccaagagcaa atgcacttga atccaagaga aacgcaaagc  48180
tttttctctt cacgatcaga atcctaaagt ctaaagtcca tattggaaaa gctcgatacc  48240
gaggcttaaa cgtcaatcaa atcagaataa ttatcagagt tcagtttgag acctaattgt  48300
aaaaggtcgg tgttcttctc aaataaaaag ttttgtaatc atttagtgaa ataaaaatta  48360
tatttttca cttataaata ttgcaagaat ttaattggcg cagtcggtag gatccaataa   48420
aataaaagag tccttttagt acggtactga tcaactaaat gatatgctat acgtctagct  48480
atccaagatc agcgaattaa aatagtgatt cgaaatatt ttagagatcc gtaaagaat   48540
ctacgtgaaa gtagtattca aagtaaaatc ccgtgcggtc ggaaacaata atttaaattt  48600
tttaattccg aaacttaaaa ccaagtttaa agaaaactta aaaccaagtt taagaaaaac  48660
ttaaaaccaa gttaaagaa aacttaaaac cagtttaagg aaacttaaaa ccagtttaaa   48720
gaaataagt ttaaagaaaa cttaaaatca agaaaactta aaaccaagtt taagaaaaac   48780
tcaaaatcaa gaaaacttaa agccaaaata agctagaaaa ctaaaagaca tcatggcagt  48840
cccacaactc tcagaaacac acctaaacca actgctaaac caaatcaaag aattaaacta  48900
ctacgatggc gcacctggaa ttatctggat tcgtcaacca agtggaacaa ctgnctcagt  48960
ttatacccaa cacaggaagc aagacaggca cacgtcatat atggagcagt gaagcggtta  49020
ttagtggatt cagccttaga agtcgtaacc caggaaagag ctaacacatg gctgacatg   49080
aagaaagaac acggcaatgg tattcaaaga ccatagacct tatgtaactc tcatcagaca  49140
attagaagac atatcatacc caggaagtat ctgtaagttt atagaaatag aaacacaata  49200
ctggattatg ttcgataagt tagaattaga aagtgaccat gttgataaat cgaattatac  49260
cgaaatgtta aacaaaactg ttaaatcagt aatagatcga aaactgccgg atagaattta  49320
tatgttttg gcaacgtaaa gatattgata caatttattt aaaacaagca tcaatgnaat  49380
taggcctta tgatgctatt ccagaaaatc accgttctaa tagaacagaa atgaataaac  49440
gtaggaacag gggaaactat aatcaaaata ataatcaaaa atattacaat aaatagaaat  49500
cacaactaca gtaattatta tcctagcatg aatcagaatc ataatacaca accacctcag  49560
aatccgactc aacctatgac aaatcaaaac caatattcac cgcgtttcat accgaataat  49620
caaagaggga attattatgc atttagacga gacttaacac aagctcagca gaacaaccca  49680
cttaataaca cccttaactt ccaaccttcg acatcgaata atattaacag acaagggcca  49740
gtaaaaagac aacgcgagag tcagagtgac caaagcagga tggatgtaaa ttttcatcaa  49800
gctgcctcgg acactcaaat gatagagaag gacatacaag tccctatgta aaataattc   49860
```

```
atcataataa aaattataag ggaatgatcg atacaggatc atcnnttaac atcataagag    49920
aaaattttga gaacttagaa gaaaaggaag aaaacctaat agtatacact attaaaggac    49980
caataacact aaagagaagt ataataataa aacctacttc agtatgtccg tctgctcaaa    50040
aattctacat tcacaaattt tcngananna tnatttcngg tagntngaaa gttntnnaga    50100
nccaaangcc ttattgnttt angcaacggg ccagtagnta ggctcaaaat tntttagttt    50160
ctntatanaa aannaaggnn gagaccgcat ccaaacgcnt tgnccnaacc aagagaatga    50220
tncgntttag tggacanaat caaancanan atgcaaaagg ttaagacccc acctaagtgc    50280
cttaanccaa agcatnaaca tcaagagang gagactgcat tacccaaatg cgntcatttc    50340
gaatgttgtt aaagacacag tggacaatga tgtaacacat ctcgatccca tgtccgttga    50400
cnacgatata gccnacttcg cgattaataa tgagttacgc gaatgtaacg agtatagact    50460
ngaacacttn aatgcanagg aagttgaatg tttaaagaag gtcctatncg aatanagana    50520
cattcagtac aaagagggcg aanatttnnc nttcaccagt nctattaanc atgtcatccg    50580
aantcaacan gaagacccag tataccgtaa accctncang taccctcaga gcgttgacca    50640
anaagtcacc nancaaattn aananatgat aggcnaggga ttgttcnaaa atcgnagtcc    50700
ccttattgtt catcctatgt gggtggtccc caagaaggca gncgcctctg gganaaaaaa    50760
tgcaggttgg tagtcgatta cagnaatcta natganataa ctgttagcga ccaatttccc    50820
attccccgaa tgntntccct angtnagtcg tnntaanggc cgccagagnt tntcatntna    50880
nttcccgtnc cgttagcaa                                                 50899
```